(12) United States Patent
Wengel et al.

(10) Patent No.: US 7,060,809 B2
(45) Date of Patent: Jun. 13, 2006

(54) LNA COMPOSITIONS AND USES THEREOF

(75) Inventors: Jesper Wengel, Odense S (DK); Sakari Kauppinen, Smoerum (DK)

(73) Assignee: Exiqon A/S, Vedbaek (DE)

( * ) Notice: Subject to any disclaimer, the term of this patent is extended or adjusted under 35 U.S.C. 154(b) by 5 days.

(21) Appl. No.: 10/235,683

(22) Filed: Sep. 4, 2002

(65) Prior Publication Data

US 2003/0224377 A1 Dec. 4, 2003

Related U.S. Application Data

(60) Provisional application No. 60/317,034, filed on Sep. 4, 2001, provisional application No. 60/323,967, filed on Sep. 22, 2001.

(51) Int. Cl.
*C07H 21/00* (2006.01)
*C07H 21/02* (2006.01)
*C07H 21/04* (2006.01)
*C12Q 1/68* (2006.01)
*C12P 19/34* (2006.01)

(52) U.S. Cl. ............... 536/23.1; 536/24.3; 536/24.33; 435/6; 435/91.1; 435/91.2

(58) Field of Classification Search ............ 435/6, 435/91.1, 91.2; 536/23.1, 24.3, 24.33
See application file for complete search history.

(56) References Cited

U.S. PATENT DOCUMENTS

| 3,687,808 | A | 8/1972 | Merigan, Jr. et al. |
|---|---|---|---|
| 4,806,463 | A | 2/1989 | Goodchild et al. |
| 5,432,272 | A | 7/1995 | Benner |
| 6,083,482 | A | 7/2000 | Wang |
| 6,352,858 | B1 | 3/2002 | Cowsert et al. |
| 6,440,739 | B1 | 8/2002 | Bennett et al. |
| 6,841,539 | B1 | 1/2005 | Mehta et al. |
| 2003/0175728 | A1* | 9/2003 | Belousov et al. ............ 435/6 |
| 2004/0092462 | A1 | 5/2004 | Bennett et al. |
| 2005/0080246 | A1 | 4/2005 | Allerson et al. |

FOREIGN PATENT DOCUMENTS

| WO | WO 96/31557 | 10/1996 |
|---|---|---|
| WO | WO 99/14226 | 3/1999 |
| WO | WO 00/56746 | 9/2000 |
| WO | WO 00/56748 | 9/2000 |
| WO | WO 00/66604 | 11/2000 |

OTHER PUBLICATIONS

Babu et al., "Universal Hybridization Using LNA (Locked Nucleic Acid) Containing a Novel Pyrene LNA Nucleotide Monomer," *Chemical Communications* 20:2114 (2001).
Bassett et al., "Gene Expression Informatics—It's All in Your Mind," *Nature Genetics*, Suppl. 21:51 (1999).

(Continued)

*Primary Examiner*—Jezia Riley
(74) *Attorney, Agent, or Firm*—Clark & Elbing LLP; Kristina Bieker-Brady

(57) ABSTRACT

Modified LNA units are provided that comprises unique base groups. Desirable nucleobase and nucleosidic base substitutions can mediate universal hybridization when incorporated into nucleic acid strands. The novel LNA compounds may be used in a wide variety of applications, such as PCR primers, sequencing, synthesis of antisense oligonucleotides, diagnostics and the like.

41 Claims, 2 Drawing Sheets

OTHER PUBLICATIONS

Beier et al., "Chemical Etiology of Nucleic Acid Structure: Comparing Pentopyranosyl—(2'→4') Oligonucleotides with RNA" *Science* 283:699 (1999).
Bowtell et al., "Options Available—from Start to Finish—for Obtaining Expression Data By Microarray," *Nature Genetics*, Suppl. 21:25 (1999).
Brown et al., "Exploring the New World of the Genome with DNA Microarrays," *Nature Genetics*, Suppl. 21:33 (1999).
Chakravarti et al., "Population Genetics—Making Sense Out of Sequence," *Nature Genetics*, Suppl. 21:56 (1999).
Cheung et al., "Making and Reading Microarrays," *Nature Genetics*, Suppl. 21:15 (1999).
Cole et al., "The Genetics of Cancer—a 3D Model," *Nature Genetics*, Suppl. 21:38 (1999).
Cook, "Medicinal Chemistry of Antisense Oligonucleotides—Future Opportunities," *Anti-Cancer Drug Design* 6:585 (1991).
Crooke, "Therapeutic Applications of Oligonucleotides," *Ann. Rev. Pharm. Toxicol.* 32:329 (1992).
Debouck et al., "DNA Microarrays in Drug Discovery and Development," *Nature Genetics*, Suppl. 21:48 (1999).
Devereux et al., "A Comprehensive Set of Sequence Analysis Programs for the VAX," *Nucleic Acids Res.* 12:387 (1984).
Duggan et al., "Expression Profiling Using cDNA Microarrays," *Nature Genetics*, Suppl. 21:10 (1999).
Englisch et al., "Chemically Modified Oligonucleotides as Probes and Inhibitors," *Angewandte Chemie, International Edition* 30:613 (1991).
Eschenmoser, "Chemical Etiology of Nucleic Acid Structure," *Science* 284:2118 (1999).
Freier et al., "The Ups and Downs of Nucleic Acid Duplex Stability: Structure—Stability Studies on Chemically—Modified DNA: RNA Duplexes," *Nucleic Acid Research* 25:4429 (1997).
Hacia et al., "Resequencing and Mutational Analysis Using Oligonucleotide Microarrays," *Nature Genetics*, Suppl. 21:42 (1999).
Harrington et al., "Functional Domains within FEN-1 and RAD2 Define a Family of Structure-Specific Endonucleases: Implications for Nucleotide Excision Repair," *Genes Dev.* 8:1344 (1994).
Hermanson et al., Chapter 3, *Immobilized Affinity Ligand Techniques*, Academic Press, San Diego, CA, 137-279 (1992).
Koshkin et al., "LNA (Locked Nucleic Acids): Synthesis of the Adenine, Cytosine, Guanine, 5-Methylcytosine Thymine and Uracil Bicyclonucleoside Monomers, Oligomerisation, and Unprecedented Nucleic Acid Recognition," *Tetrahedron* 54:3607 (1998).
Kvaerno et al., "Investigation of Restricted Backbone Conformations as an Explanation for the Exceptional Thermal Stabilities of Duplexes Involving LNA (Locked Nucleic Acid): Synthesis and Evaluation of Abasic LNA," *Chem. Commun.* 657 (1999).
Lander et al., "Array of Hope," *Nature Genetics*, Suppl. 21:3 (1999).
Lipshutz et al., "High Density Synthetic Oligonucleotide Arrays," *Nature Genetics*, Suppl. 21:20 (1999).

Loakes, "Survey and Summary: The Applications of Universal DNA Base Analogues," *Nucleic Acids Research* 29:2437 (2001).
Matray et al., "Selective and Stable DNA Base Pairing without Hydrogen Bonds," *J. Am. Chem. Soc.* 120:6191 (1998).
Mesmaeker et al., "Backbone Modifications in Oligonucleotides and Peptide Nucleic Acid Systems," *Current Opinion in Structural Biology* 5:343 (1995).
Murante et al., "The Calf 5'—to 3'- Exonuclease Is Also an Endonuclease with Both Activities Dependent on Primers Annealed Upstream of the Point of Cleavage," *J. Biol. Chem.* 269:1191 (1994).
Nielsen et al., "Synthesis of 2'-O,3'-C-linked Bicyclic Nucleosides and Bicyclic Oligonucleotides," *J. Chem. Soc. Perkin. Trans.* 1:3423 (1997).
Obika et al., "Stability and Structural Features of the Duplexes Containing Nucleoside Analogues With A Fixed N-Type Conformation, 2'-O,4'-C-Methyleneribonucleosides," *Tetrahedron Letters* 39:5401 (1998).
Obika et al., "Synthesis of 2'-O,4'-C-Methyleneuridine and -cytidine. Novel Bicyclic Nucleosides Having a Fixed $C_3$-Endo Sugar Puckering," *Tetrahedron Letters* 38:8735 (1997).
Obika et al., "Synthesis of Conformationally Locked C-Nucleosides Having a 2,5-Dioxabicyclo[2.2.1] Heptane Ring System," *Tetrahedron Letters* 41:215 (2000).
Obika et al., "Triplex Formation by an Oligonucleotide Containing Conformationally Locked C-Nucleoside, 5-(2-O,4-C-methylene-β-D-Ribofuranosyl) Oxazole," *Tetrahedron Letters* 41:221 (2000).
Orum et al., "Locked Nucleic Acids: a Promising Molecular Family for Gene-function Analysis and Antisense Drug Development," *Current Opinion in Molecular Therapeutics* 3:239 (2001).
Sanger et al., "DNA Sequencing with Chain-Terminating Inhibitors," *Proc. Natl. Acad. Sci. USA* 74:5463 (1977).
Sanghvi, Chapter 15, Heterocyclic Base Modifications in Nucleic Acids and Their Applications in Antisense Oligonucleotides, *Antisense Research and Application*, Ed. S. T. Crooke and L. Lebleu, CRC Press (1993).
Singh et al., "LNA (Locked Nucleic Acids): Synthesis and High-Affinity Nucleic Acid Recognition," *Chem. Commun.* 455 (1998).
Singh et al., "Synthesis of Novel Bicyclo [2.2.1] Ribonucleosides: 2'-amino- and 2'-thio-LNA Monomeric Nucleosides," *J. Org. Chem.* 63:6078 (1998).
Southern et al., "Molecular Interactions on Microarrays," *Nature Genetics*, Suppl. 21:5 (1999).
Uhlmann et al., "Antisense Oligonucleotides: A New Therapeutic Principle," *Chemical Reviews* 90:543 (1990).
Yamaguchi et al., "Synthesis of 4'-C-Ethynyl-β-D-*ribo*-pentofuranosyl Pyrimidines," *Biosci. Biotechnol. Biochem.*, 63:736 (1999).
Zamecnik et al., "Inhibition of Rous Sarcoma Virus Replication and Cell Transformation by a Specific Oligodeoxynucleotide," *Proc. Natl. Acad. Sci. USA* 75:280 (1978).

* cited by examiner

Melting temperatures (Tm) of the complementary DNA-DNA and LNA-DNA duplexes.[a] Modified monomers (LNA are in CAPITALs): I = inosine; D = 2,6-diaminopurine; X = 2-aminopurine.

| Entry | Oligonucleotide structure | Tm (± 0.5 °C) of the duplexes with complementary deoxynucleotide | | | |
|---|---|---|---|---|---|
| | | 3'-ctgtatcc | 3'-ctgaatcc | 3'-ctggatcc | 3'-ctgcatcc |
| 1 | 5'-gacatagg | 23.8 | <10 | <10 | <10 |
| 2 | 5'-gacttagg | <10 | 22.6 | <10 | <10 |
| 3 | 5'-gacgtagg | <10 | <10 | <10 | 25.0 |
| 4 | 5'-gacdtagg | 23.3 | <10 | <10 | <10 |
| 5 | 5'-gdcdtdgg | 33.4 | <10 | <10 | 17.7 |
| 6 | 5'-gacitagg | <10 | <10 | <10 | 20.9 |
| 7 | 5'-gacxtagg | <10 | <10 | <10 | <10 |
| 8 | 5'-GACATAGG | 61.6 | 38.2 | 43.4 | 40.6 |
| 9 | 5'-GACTTAGG | 28.0 | 60.7 | 36.4 | 23.5 |
| 10 | 5'-GACGTAGG | 55.0 | 32[b] | 41[b] | 70.9 |
| 11 | 5'-GACDTAGG | 67.8 | 42.2 | 41.4 | 52.4 |
| 12 | 5'-GDCDTDGG | 78.3 | 55.9 | 54.7 | 63.8 |
| 13 | 5'-GACITAGG | 53.1 | 48.2 | 43.0 | 59.9 |

[a] The melting temperatures (Tm values) were obtained as a maxima of the first derivatives of the corresponding melting curves (optical density at 260 nm vesus temperature). Concentration of the duplexes: 2.5 µM. Buffer: 0.1 M NaCl; 10 mM Na-phosphate (pH 7.0); 1 mM EDTA.
[b] Low cooperativity of transitions (accuracy ± 1 °C).

Figure 2

SEQUENCE LISTING

<160> NUMBER OF SEQ ID NOS: 11

<210> SEQ ID NO 1
<211> LENGTH: 23
<212> TYPE: DNA
<213> ORGANISM: Artificial Sequence
<220> FEATURE:
<223> OTHER INFORMATION: Degenerate Primer
<220> FEATURE:
<221> NAME/KEY: misc_feature
<222> LOCATION: 3, 6
<223> OTHER INFORMATION: n = A,T,C or G

<400> SEQUENCE: 1
acncgntact gggactgctg caa                                                23

<210> SEQ ID NO 2
<211> LENGTH: 23

```
<212> TYPE: DNA
<213> ORGANISM: Artificial Sequence
<220> FEATURE:
<223> OTHER INFORMATION: Degenerate Primer
<220> FEATURE:
<221> NAME/KEY: misc_feature
<222> LOCATION: 3
<223> OTHER INFORMATION: n = A,T,C or G

<400> SEQUENCE: 2
acnagatatt gggattgttg taa                                              23

<210> SEQ ID NO 3
<211> LENGTH: 23
<212> TYPE: DNA
<213> ORGANISM: Artificial Sequence
<220> FEATURE:
<223> OTHER INFORMATION: Degenerate Primer
<220> FEATURE:
<221> NAME/KEY: misc_feature
<222> LOCATION: 3
<223> OTHER INFORMATION: n = A,T,C or G

<400> SEQUENCE: 3
acncggtact gggactgctg caa                                              23

<210> SEQ ID NO 4
<211> LENGTH: 21
<212> TYPE: DNA
<213> ORGANISM: Artificial Sequence
<220> FEATURE:
<223> OTHER INFORMATION: Degenerate Primer
<220> FEATURE:
<221> NAME/KEY: misc_feature
<222> LOCATION: 12, 15, 21
<223> OTHER INFORMATION: n = A,T,C or G

<400> SEQUENCE: 4
tgctacgaac tnacnttcca n                                                21

<210> SEQ ID NO 5
<211> LENGTH: 21
<212> TYPE: DNA
<213> ORGANISM: Artificial Sequence
<220> FEATURE:
<223> OTHER INFORMATION: Degenerate Primer
<220> FEATURE:
<221> NAME/KEY: misc_feature
<222> LOCATION: 15, 21
<223> OTHER INFORMATION: n = A,T,C or G

<400> SEQUENCE: 5
tcttatgagt taacntttca n                                                21

<210> SEQ ID NO 6
<211> LENGTH: 21
<212> TYPE: DNA
<213> ORGANISM: Artificial Sequence
<220> FEATURE:
<223> OTHER INFORMATION: Degenerate Primer
<220> FEATURE:
<221> NAME/KEY: misc_feature
<222> LOCATION: 15, 21
<223> OTHER INFORMATION: n = A,T,C or G

<400> SEQUENCE: 6
tgctacgacc tgacnttcca n                                                21

<210> SEQ ID NO 7
```

```
<211> LENGTH: 21
<212> TYPE: DNA
<213> ORGANISM: Artificial Sequence
<220> FEATURE:
<223> OTHER INFORMATION: Degenerate Primer
<220> FEATURE:
<221> NAME/KEY: misc_feature
<222> LOCATION: 12, 15, 21
<223> OTHER INFORMATION: n = A,T,C or G

<400> SEQUENCE: 7
tgctacgatc tnacnttcca n                                              21

<210> SEQ ID NO 8
<211> LENGTH: 22
<212> TYPE: DNA
<213> ORGANISM: Artificial Sequence
<220> FEATURE:
<223> OTHER INFORMATION: Degenerate Primer
<220> FEATURE:
<221> NAME/KEY: misc_feature
<222> LOCATION: 12, 15, 22
<223> OTHER INFORMATION: n = A,T,C or G

<400> SEQUENCE: 8
tgctaccaac tnacnattcc an                                             22

<210> SEQ ID NO 9
<211> LENGTH: 21
<212> TYPE: DNA
<213> ORGANISM: Artificial Sequence
<220> FEATURE:
<223> OTHER INFORMATION: Degenerate Primer
<220> FEATURE:
<221> NAME/KEY: misc_feature
<222> LOCATION: 15, 21
<223> OTHER INFORMATION: n = A,T,C or G

<400> SEQUENCE: 9
tgctacgaac tgacnttcca n                                              21

<210> SEQ ID NO 10
<211> LENGTH: 8
<212> TYPE: PRT
<213> ORGANISM: Artificial Sequence
<220> FEATURE:
<223> OTHER INFORMATION: Consensus Sequence

<400> SEQUENCE: 10

Thr Arg Tyr Trp Asp Cys Cys Lys
 1               5

<210> SEQ ID NO 11
<211> LENGTH: 7
<212> TYPE: PRT
<213> ORGANISM: Artificial Sequence
<220> FEATURE:
<223> OTHER INFORMATION: Consensus Sequence
<220> FEATURE:
<221> NAME/KEY: VARIANT
<222> LOCATION: 3
<223> OTHER INFORMATION: Xaa = Glu, Asp or Gln

<400> SEQUENCE: 11

Cys Tyr Xaa Leu Thr Phe Thr
 1               5
```

LNA COMPOSITIONS AND USES THEREOF

CROSS-REFERENCE TO RELATED APPLICATION

This application claims the benefit of the filing date of U.S. provisional application U.S. Ser. No. 60/317,034, filed Sep. 4, 2001 and U.S. provisional application U.S. Ser. No. 60/323,967, filed Sep. 22, 2001.

BACKGROUND OF THE INVENTION

1. Field of the Invention

The invention relates to modified Locked Nucleic Acid (LNA) units (e.g, individual LNA monomers and oligomers that include LNA monomers), particularly such monomers and oligomers having unique base groups. Desirable nucleobase and nucleosidic base substitutions can mediate universal hybridization when incorporated into nucleic acid strands. The novel LNA compounds may be used in a wide variety of applications, such as PCR primers, sequencing, synthesis of antisense oligonucleotides, diagnostics and the like.

2. Background

For disease states, classical therapeutics has generally focused upon interactions with proteins in an effort to moderate their disease-causing or disease-potentiating functions. In newer therapeutic approaches, modulation of the actual production of such protein is desired. By interfering with the production of proteins, the maximum therapeutic effect can be obtained with minimal side effects. It is therefore a general object of such therapeutic approaches to interfere with or otherwise modulate gene expression, which would otherwise lead to the formation of undesired protein or proteins. One method for inhibiting specific gene expression is with the use of oligonucleotides, especially oligonucleotides which are complementary to a specific target messenger RNA (mRNA) sequence.

Oligonucleotides are also widely used as research reagents. They are useful for understanding the function of many other biological molecules as well as in the preparation of other molecules. For example, the use of oligonucleotides as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies, and genetic counseling. Commercialization has led to the development of kits which assist non-molecular biology-trained personnel in applying PCR. Oligonucleotides are also employed as primers in such PCR technology.

Oligonucleotides are also used in other laboratory procedures. Several of these uses are described in common laboratory manuals such as Molecular Cloning, A Laboratory Manual, Second Ed., J. Sambrook, et al., Eds., Cold Spring Harbor Laboratory Press, 1989; and Current Protocols In Molecular Biology, F. M. Ausubel, et al., Eds., Current Publications, 1993. Such uses include i) generating synthetic labeled oligonucleotide probes for visualization after in situ hybridization, ii) generating microarray capture probes, iii) generating capture probes for nucleic acid sample preparations, iv) screening libraries with oligomeric compounds, v) DNA sequencing, vi) in vitro amplification of DNA by the polymerase chain reaction, vii) using fluorescently labeled oligonuclotides for real time vizualisation of PCR amplification efficiency (double dye probed, molecular beacons, and scorpions) and viii) site-directed mutagenesis of cloned DNA. See Book 2 of Molecular Cloning, A Laboratory Manual, supra. See Book 2 of Molecular Cloning, A Laboratory Manual, supra. See also "DNA-protein interactions and The Polymerase Chain Reaction" in Vol. 2 of Current Protocols In Molecular Biology, supra. Oligonucleotides have even been used as building blocks in nanotechnology applications to make molecular structures with a defined geometry (cubes, cylinders etc.).

Certain chemical modifications have been introduced into oligonucleotides to increase their usefulness in diagnostics, as research reagents and as therapeutic entities. Such modifications include those designed to increase binding to a target strand (i.e. increase melting temperatures, Tm), to assist in identification of an oligonucleotide or an oligonucleotide-target complex, to increase cell penetration, to stabilize against nucleases and other enzymes that degrade or interfere with the structure or activity of the oligonucleotides, to provide a mode of disruption (terminating event) once sequence-specifically bound to a target, and to improve the pharmacokinetic properties of the oligonucleotide.

It would be desirable to have new nucleic acid compounds that could provide useful properties in a variety of applications, including hybridization applications.

SUMMARY OF THE INVENTION

The present invention relates to novel Locked Nucleic Acid (LNA) compositions that can alter nucleic acid hybridization, synthesis, PCR, DNA restriction and sequencing using modified nucleic acid compounds, particularly LNA units (e.g., individual LNA monomers or oligomers that include LNA monomers) that comprise one or more unique base groups.

Modified nucleic acid monomers and oligomers of the invention contain at least one LNA unit and/or at least one modified nucleobase or nucleosidic base (often referred to herein as a universal or modified base). Modified nucleobases or nucleosidic bases contain non-natural base groups (i.e. other than adenine, guanine, cytosine, uracil or thymine) but effectively hybridize to nucleic acid units that contain adenine, guanine, cytosine, uracil or thymine moieties. Exemplary oligomers contain 2 to 100, 5 to 100, 4 to 50, 5 to 50, 5 to 30, or 8 to 15 nucleic acid units. In some embodiments, one or more LNA units with natural nucleobases are incorporated into the oligonucleotide at a distance from the LNA unit having a modified base of 1 to 6 or 1 to 4 bases. In certain embodiments, at least two LNA units with natural nucleobases are flanking a LNA unit having a modified base on both sides thereof. Desirably, at least two LNA units independently are positioned at a distance from the LNA unit having the modified base of 1 to 6 or 1 to 4 bases.

Typical modified bases of the present invention when incorporated into an oligonucleotide containing all LNA units or a mixture of LNA and DNA or RNA units will exhibit substantially constant $T_m$ values upon hybridization with a complementary oligonucleotide, irrespective of the bases (natural) present on the complementary oligonucleotide.

In particular, typically desirable modified bases of the present invention when incorporated into a 9-mer oligonucleotide (all other eight residues or units being natural DNA or RNA units with natural bases) will exhibit a $T_m$ difference equal to or less than about 15, 12, 10, 9, 8, 7, 6, 5, 4, 3 or 2° C. upon hybridizing to the four complementary oligonucleotide variants that are identical except for the unit corresponding to the LNA unit, where each variant has one of the natural bases uracil, cytosine, thymine, adenine or guanine. That is, the highest and the lowest $T_m$ (referred to herein as the $T_m$ differential) obtained with such four complementary sequences will be about 15, 12, 10, 9, 8, 7, 6, 5, 4, 3 or 2° C. or less.

Desirable modified nucleobases or nucleosidic bases for use in nucleic acid compositions of the invention include optionally substituted carbon alicyclic or carbocyclic aryl groups (i.e. only carbon ring members), particularly multi-ring carbocyclic aryl groups such as groups having 2, 3, 4, 5, 6, 7, or 8 linked, particularly fused carbocyclic aryl moieties. Optionally substituted pyrene is also desirable. Such nucleobases or nucleosidic bases can provide significant performance results, as demonstrated for instance in the examples which follow. Heteroalicyclic and heteroaromatic nucleobases or nucleosidic bases also will be suitable as discussed below. In some embodiments, the carbocyclic moiety is linked to the 1'-position of the LNA unit through a linker (e.g., a branched or straight alkylene or alkenylene).

References herein to LNA units indicate a nucleic acid unit that has a carbon or hetero alicyclic ring with four to six ring members, e.g. a firanose ring, or other alicyclic ring structures such as a cyclopentyl, cycloheptyl, tetrahydropyranyl, oxepanyl, tetrahydrothiophenyl, pyrrolidinyl, thianyl, thiepanyl, piperidinyl, and the like. In one aspect of the invention at least one ring atom of the carbon or hetero alicyclic group is taken to form a further cyclic linkage to thereby provide a multi-cyclic group. The cyclic linkage may include one or more, typically two atoms, of the carbon or hetero alicyclic group. The cyclic linkage also may include one or more atoms that are substituents, but not ring members, of the carbon or hetero alicyclic group.

Desirable LNA units include those that contain a furanosyl-type ring and one or more of the following linkages: C-1', C-2'; C-2', C-3'; C-2', C-4'; or a C-2', C-5'linkage. A C-2', C-4' is particularly desirable. In another aspect of the invention, desirable LNA units are compounds having a substituent on the 2'-position of the central sugar moiety (e.g., ribose or xylose), or derivatives thereof, which favors the C3'-endo conformation, commonly referred to as the North (or simply N for short) conformation. Desirable LNA unitsaccording to this second aspect of the invention include 2'-O-methyl, 2'-fluoro, 2'-allyl, and 2'-O-methoxyethoxy derivatives. Other desirable LNA units are further discussed below and in International Patent Publication WO 99/14226, WO 00/56746, and O 00/66604. Exemplary nucleic acids contain one or more units selected from the group consisting of 2'-O,4'-C-methylene-β-D-ribofuranosyls, 2'-deoxy-2'-fluoro ribonucleotides, 2'-O-methyl ribonucleotides, 2'-O-methoxyethyl ribonucleotides, peptide nucleic acids, 5-propynyl pyrimidine ribonucleotides, 7-deazapurine ribonucleotides, 2,6-diaminopurine ribonucleotides, and 2-thio-pyrimidine ribonucleotides.

Oligonucleotides of the invention contain at least one LNA unit with a modified base as disclosed herein. Suitable oligonucleotides also may contain natural DNA or RNA units (e.g., nucleotides) with natural bases, as well as LNA units that contain natural bases. Furthermore, the oligonucleotides of the invention also may contain modified DNA or RNA, such as 2'-O-methyl RNA, with natural bases. Desirable oligonucleotides contain at least one of and desirably both of 1) one or more DNA or RNA units (e.g., nucleotides) with natural bases, and 2) one or more LNA units with natural bases, in addition to LNA units with a modified base.

LNA oligonucleotides with natural bases obey Watson-Crick base-pairing rules and form duplexes that are significantly more stable than similar duplexes formed by DNA oligonucleotides. In addition, LNA oligonucleotides are capable of hybridizing with double-stranded DNA target molecules as well as RNA secondary structures by strand invasion as well as of specifically blocking a wide selection of enzymatic reactions such as, digestion of double-stranded DNA by restriction endonucleases; and digestion of DNA and RNA with deoxyribonucleases and ribonucleases, respectively.

The systems disclosed herein can provide significant nucleic acid probes for universal hybridization. In particular, universal hybridization can be accomplished with a conformationally restricted monomer, including a desirable pyrene LNA monomer. Universal hybridization behavior also can be accomplished in an RNA context. Additionally, the binding affinity of probes for universal hybridization can be increased by the introduction of high affinity monomers without compromising the base-pairing selectivity of bases neighboring the universal base.

Incorporation of one or more modified nucleobases or nucleosidic bases into an oligonucleotide can provide significant advantages. Among other things, LNA oligonucleotides can often self-hybridize, rather than hybridize to another oligonucleotide. Use of one or more modified bases with the LNA units can modulate affinity levels of the oligo, thereby inhibiting undesired self-hybridization.

The invention also includes methods for synthesis of the monomers and oligomers disclosed herein, including those syntheses disclosed in Scheme 1 and 2 below as well as in the examples which follow.

Modified nucleic acid compounds of the invention that contain base substitution (often referred to hereinafter as universal bases) can mediate universal hybridization when incorporated into e.g. a DNA strand, RNA strand and/or chimeric molecules such as a 2'-OMe-RNA/LNA chimeric strand. Desirable examples of novel LNA nucleotides with substitutions include pyrene-LNA or pyrenyl-LNA nucleotides. With respect to a 2'-OMe-RNA/LNA chimeric strand, the compounds of the invention have a high affinity hybridization without compromising the base-pairing selectivity of bases neighboring the universal base monomers. Methods of detection and evaluation of the universal bases are described in detail in the Examples which follow.

Oligonucleotides of the invention can be employed in a wide range of applications, particularly those in those applications involving a hybridization reaction. Oligonucleotides also may be used in DNA sequencing aiming at improved throughput in large-scale, shotgun genome sequencing projects, improved throughput in capillary DNA sequencing (e.g. ABI prism 3700) as well as at an improved method for 1) sequencing large, tandemly repeated genomic regions, 2) closing gaps in genome sequencing projects and 3) sequencing of GC-rich templates. In DNA sequencing, oligonucleotide sequencing primers are combined with LNA enhancer elements for the read-through of GC-rich and/or tandemly repeated genomic regions, which often present many challenges for genome sequencing projects.

Oligonucleotides of the invention desirably contain at least 50 percent or more, more desirably 55, 60, 65, or 70 percent or more of non-modified or natural DNA or RNA units (e.g., nucleotides) or units other than LNA units based on the total number of units or residues of the oligo. A non-modified nucleic acid as referred to herein means that the nucleic acid upon incorporation into a 10-mer oligomer will not increase the $T_m$ of the oligomer in excess of 1° C. or 2° C. More desirably, the non-modified nucleic acid unit (e.g., nucleotide) is a substantially or completely "natural"

nucleic acid, i.e. containing a non-modified base of uracil, cytosine, thymine, adenine or guanine and a non-modified pentose sugar unit of β-D-ribose (in the case of RNA) or β-D-2-deoxyribose (in the case of DNA).

Oligonucleotides of the invention suitably may contain only a single modified (i.e. LNA) nucleic acid unit, but desirably an oligonucleotide will contain 2, 3, 4 or 5 or more modified nucleic acid units. Typically desirable is where an oligonucleotide contains from about 5 to about 40 or 45 percent modified (LNA) nucleic acid units, based on total units of the oligo, more desirably where the oligonucleotide contains from about 5 or 10 percent to about 20, 25, 30 or 35 percent modified nucleic acid units, based on total units of the oligo.

Typical oligonucleotides that contain one or more LNA units with a modified base as disclosed herein suitably contain from 3 or 4 to about 200 nucleic acid repeat units, with at least one unit being an LNA unit with a modified base, more typically from about 3 or 4 to about 5, 6, 7, 8, 9, 10, 15, 20, 30, 40, 50, 60, 70, 80, 90, 100, 110, 120, 130, 140 or 150 nucleic acid units, with 1, 2, 3, 4, 5, 6, 7, 8, 9, or 10 LNA units with a modified base being present.

As discussed above, particularly desirable oligonucleotides will contain a non-modified DNA or RNA units at 3' and/or 5' ends and a modified DNA or RNA unit at one position upstream from (generally referred to herein as the −1, position) either or both the 3' and 5' terminal non-modified nucleic acid units. In some embodiments, the modified base is at the 3' terminal position of a nucleic acid primer, such as a primer for the dection of a single nucleotide polymorphism.

Also desirable are oligonucleotides that do not have an extended stretches of modified DNA or RNA units, e.g. greater than about 4, 5 or 6 consecutive modified DNA or RNA units. That is, desirably one or more non-modified DNA or RNA will be present after a consecutive stretch of about 3, 4 or 5 modified nucleic acids.

Generally desirable are oligonucleotides that contain a mixture of LNA units that have non-modified or natural nucleobases (i.e. adenine, guanine, cytosine, uracil or thymine) and LNA units that have modified base groups as disclosed herein.

Particularly desirable oligonucleotides of the invention include those where an LNA unit with a modified base is interposed between two LNA units each having non-modified or natural bases (adenine, guanine, cytosine, uracil or thymine). The LNA "flanking" units with natural base moieties may be directly adjacent to the LNA with modified base moiety, or desirably is within 2, 3, 4 or 5 nucleic acid units of the LNA unit with modified base. Nucleic acid units that may be spaced between an LNA unit with a modified base and a LNA unit with natural nucleobases suitably are DNA and/or RNA and/or alkyl-modified RNA/DNA units, typically with natural base moieties, although the DNA and/or RNA units also may contain modified base moieties.

The oligonucleotides of the present invention are comprised of at least about one universal base. Oligonucleotides of the present can also be comprised, for example, of between about one to six 2'-OMe-RNA unit, at least about two LNA units and at least about one LNA pyrene unit.

As discussed above, a variety of locked nucleic acids may be employed in the monomers and oligomers of the invention including bicyclic and tricyclic DNA or RNA having a 2'–4' or 2'–3' sugar linkages; 2'-O,4'-C-methylene-β-D-ribofuranosyl moiety, known to adopt a locked C3'-endo RNA-like furanose conformation. Illustrative modified structures that may be included in oligonucleotides of the invention are shown in FIG. 1. Other nucleic acid units that may be included in an oligonucleotide of the invention may comprise 2'-deoxy-2'-fluoro ribonucleotides; 2'-O-methyl ribonucleotides; 2'-O-methoxyethyl ribonucleotides; peptide nucleic acids; 5-propynyl pyrimidine ribonucleotides; 7-deazapurine ribonucleotides; 2,6-diaminopurine ribonucleotides; and 2-thio-pyrimidine ribonucleotides, and nucleotides with other sugar groups (e.g. xylose).

It also has been found that oligonucleotides will be particularly useful for detection and analysis of mutations including SNPs. In particular, for at least some applications, it may be desirable to employ an oligonucleotide as a "mutation resistant probe", i.e. a probe which does not detect a certain single base variation (complementary to the LNA unit with modified base) but maintains specific base pairing for other units of the probe. Hence, such a probe of the invention can detect a range of related mutatants.

In another aspect, the invention features a population of two or more nucleic acids of the invention. The populations of nucleic acids of the invention may contain any number of unique molecules. For example, the population may contain as few as 10, $10^2$, $10^4$, or $10^5$ unique molecules or as many as $10^7$, $10^8$, $10^9$ or more unique molecules. In desirable embodiments, at least 1, 5, 10, 50, 100 or more of the polynucleotide sequences are a non-naturally-occurring sequence. Desirably, at least 20, 40, or 60% of the unique polynucleotide sequences are non-naturally-occurring sequences. Desirably, the nucleic acids are all the same length; however, some of the molecules may differ in length.

In one aspect, the invention features a method for amplifying nucleic acid comprising using a nucleic acid of the invention as a PCR primer. Desirably, the primer binds to a target molecule. In various embodiments, the primer binds to a target molecule of an unknown or a known sequence.

In another aspect, the invention provides a reaction substrate that includes a nucleic acid of the invention. Desirably, the nucleic acid is a capture probe, such as capture probe that can detect at least one base-pair difference between a wild type sequence of a nucleic acid of interest and one or more alleles thereof. Desirable capture probes bind to a single-stranded DNA target.

In another aspect, the invention provides a method for nucleic acid manipulation by using an oligonucleotide of the invention as a substrate for one or more nucleic acid active enzymes. Desirably, the oligonucleotide is used as a substrate for DNA or RNA polymerases.

In another aspect, the invention provides a method for nucleic acid manipulation by incubating a nucleic acid of the invention with an enzyme under conditions that allow the enzyme (e.g., a DNA or RNA polymerase or a restriction enzyme) to bind or chemically modify the nucleic acid.

In still another aspect, the invention features the use of a nucleic acid of the invention for the design of a probe which does not discriminate between a first target nucleotide and a second target nucleotide having a single base variation compared to the first target nucleotide.

In another aspect, the invention features the use of a nucleic acid of the invention for the preparation of a probe for detecting a group of target nucleic acids having identical nucleotide sequences except for one or more single base variations.

In another aspect, the invention features a method for amplifying a target nucleic acid molecule. The method involves (a) incubating a first nucleic acid of the invention with a target molecule under conditions that allow the first nucleic acid to bind the target molecule; and (b) extending the first nucleic acid with the target molecule as a template.

Desirably, the method further involves contacting the target molecule with a second nucleic acid that binds to a different region of the target molecule than the first nucleic acid. In various embodiments, the sequence of the target molecule is known or unknown.

In another aspect, the invention provides a method for detecting a target nucleic acid molecule by (a) incubating a first nucleic acid of the invention with a target molecule under conditions that allow the first nucleic acid to hybridize the target molecule; and (b) detecting the hybridization. Desirably, the method also involves contacting the target molecule with a second nucleic acid that binds to a different region of the target molecule than the first nucleic acid. In some embodiments, the first nucleic acid binds to two or more target molecules with polynucleotide sequences that differ by one or more nucleotides. Desirably, the first nucleic acid has a modified base in the position corresponding to the nucleotide that differs between two or more target molecules.

In one aspect, the invention features the use of a nucleic acid of the invention for the manufacture of a pharmaceutical composition for treatment of a disease curable by an antisense technology.

In one aspect, the invention provides a method for inhibiting the expression of a target nucleic acid in a cell. The method involves introducing into the cell a nucleic acid of the invention in an amount sufficient to specifically attenuate expression of the target nucleic acid. The introduced nucleic acid has a nucleotide sequence that is essentially complementary to a region of desirably at least 20 nucleotides of the target nucleic acid. Desirably, the cell is in a mammal.

In a related aspect, the invention provides a method for preventing, stabilizing, or treating a disease, disorder, or condition associated with a target nucleic acid in a mammal. This method involves introducing into the mammal a nucleic acid of the invention in an amount sufficient to specifically attenuate expression of the target nucleic acid, wherein the introduced nucleic acid has a nucleotide sequence that is essentially complementary to a region of desirably at least 20 nucleotides of the target nucleic acid.

In another aspect, the invention provides a method for preventing, stabilizing, or treating a pathogenic infection in a mammal by introducing into the mammal a nucleic acid of the invention in an amount sufficient to specifically attenuate expression of a target nucleic acid of a pathogen. The introduced nucleic acid has a nucleotide sequence that is essentially complementary to a region of desirably at least 20 nucleotides of the target nucleic acid.

In desirable embodiments of the therapeutic methods of the above aspects, the mammal is a human. In some embodiments, the introduced nucleic acid is single stranded or double stranded stranded.

In another aspect, the invention provides a method for amplifying a target RNA, by (a) incubating a target RNA with a nucleic acid of the invention that has two or more (e.g., 5 to 10) consecutive thymines; and (b) extending the nucleic acid with the target RNA as a template. Desirably, the nucleic acid comprises a pyrene-LNA nucleotide. In some embodiments, one or more of the thymines are part of LNA T nucleotides. Desirably, the nucleic acid is fluorescently labeled. In some embodiments, the target RNA is included in a total RNA cellular extract and/or the target RNA is eucaryotic polyadenylated mRNA. Desirably, the oligo(T) oligonucleotide primer is used in first strand cDNA synthesis for reverse transcription of eucaryotic poly(A)+ RNA directly from total RNA extracts from a cell or biological sample. In some embodiments, the nucleic acid is part of an anchoring sequence of the oligo(T).

In some embodiments, the incubation is performed in the presence of a reverse transcriptase and a stabilizing amount of a trehalose solution. In other embodiments, the incubation is performed in the presence of a thermo stable reverse transcriptase.

In still another aspect, the invention features a method for amplifying a target nucleic acid molecule involves (a) incubating a target molecule with a nucleic acid of the invention that has a region with substantial complementarity to a conserved region of two or more nucleic acids under conditions that allow the nucleic acid to bind the target molecule; and (b) extending the nucleic acid with the target molecule as a template. Desirably, the nucleic acid is used in a degenerated oligonucleotide probe for identification and/or selection of related proteins, enzymes, or protein kinase domains within prokaryotes, Archae, or eukaryotes. Desirably, the proteins, enzymes, and protein kinase domains are selected from the group consisting of retroviral aspartyl protease (accession number PF00077), eukaryotic protein kinases including the rat map kinase erk2 (accession number PF00069), hepatitis C virus non-structural protein E2/NS1 (accession number PF01560), archacal ATPase (accession number PF01637), homeobox-associated leusine zipper (PF02183), apoptosis-preventing protein (PF02331), DNA repair protein rad10 (PF03834), glycohydrolase family 11 (PF00457), and glycohydrolase family 12 (PF01670).

In one aspect, the invention provides a method for detecting a target nucleic acid molecule by (a) incubating a target molecule with a nucleic acid of the invention that comprises a region with substantial complementarity to a conserved region of two or more nucleic acids under conditions that allow the nucleic acid to hybridize to the target molecule; and (b) detecting the hybridization. Desirably, the nucleic acid is used in a degenerated oligonucleotide probe for identification and/or selection of related proteins, enzymes, or protein kinase domains within prokaryotes, Archae, or eukaryotes. Desirably, the proteins, enzymes, and protein kinase domains are selected from the group consisting of retroviral aspartyl protease (accession number PF00077), eukaryotic protein kinases including the rat map kinase erk2 (accession number PF00069), hepatitis C virus non-structural protein E2/NS1 (accession number PF01560), archaeal ATPase (accession number PF01637), homeobox-associated leusine zipper (PF02183), apoptosis-preventing protein (PF02331), DNA repair protein rad10 (PF03834), glycohydrolase family 11 (PF00457), and glycohydrolase family 12 (PF01670).

In desirable embodiments of the above amplification or detection methods, the nucleic acid includes one or more pyrene-LNA units, such as at least 5 or 10 LNA units. Desirably, the conserved region encodes a region in a protein that is involved in catalysis, substrate binding, or DNA binding.

In one aspect, the invention features the use of a nucleic acid of the invention in an oligo(T) oligonucleotide primer in first strand cDNA synthesis for reverse transcription of eukaryotic poly(A)+RNA directly from a total RNA extract from a cell or biological sample. Desirably, the nucleic acid of primer is part of an anchoring sequence of the oligo(T).

In another embodiment, the invention features the use of a nucleic acid of the invention in a degenerated oligonucleotide probe for identification and/or selection of related proteins, enzymes, or protein kinase domains within prokaryotes, Archae, or eukaryotes. Desirably, the proteins, enzymes, and protein kinase domains are selected from the group consisting of retroviral aspartyl protease (accession number PF00077), eukaryotic protein kinases including the rat map kinase erk2 (accession number PF00069), hepatitis C virus non-structural protein E2/NS1 (accession number PF01560), archaeal ATPase (accession number PF01637), homeobox-associated leusine zipper (PF02183), apoptosis-preventing protein (PF02331), DNA repair protein rad10 (PF03834), glycohydrolase family 11 (PF00457), and glycohydrolase family 12 (PF01670).

In one aspect, the invention features a method of detecting a nucleic acid of a pathogen (e.g., a nucleic acid in a sample such as a blood or urine sample from a mammal). This method involves contacting a nucleic acid probe of the invention with a nucleic acid sample under conditions that allow the probe to hybridize to at least one nucleic acid in the sample. The probe is desirably at least 60, 70, 80, 90, 95, or 100% complementary to a nucleic acid of a pathogen (e.g., a bacteria, virus, or yeast such as any of the pathgens described herein). Hybridization between the probe and a nucleic acid in the sample is detected, indicating that the sample contains the corresponding nucleic acid from a pathogen. In some embodiments, the method is used to determine what strain of a pathogen has infected a mammal (e.g., a human) by determining whether a particular nucleic acid is present in the sample. In other embodiments, the probe has a universal base in a position corresponding to a nucleotide that varys among different strains of a pathogen, and thus the probe detects the presence of a nucleic acid from any of a multiple of pathogenic strains.

In other embodiments of any of various aspects of the invention, a nucleic acid probe or primer specifically hybridizes to a target nucleic acid but does not substantially hybridize to non-target molecules, which include other nucleic acids in a cell or biological sample having a sequence that is less than 99, 95, 90, 80, or 70% identical or complementary to that of the target nucleic acid. Desirably, the amount of the these non-target molecules hybridized to, or associated with, the nucleic acid probe or primer, as measured using standard assays, is 2-fold, desirably 5-fold, more desirably 10-fold, and most desirably 50-fold lower than the amount of the target nucleic acid hybridized to, or associated with, the nucleic acid probe or primer. In other embodiments, the amount of a target nucleic acid hybridized to, or associated with, the nucleic acid probe or primer, as measured using standard assays, is 2-fold, desirably 5-fold, more desirably 10-fold, and most desirably 50-fold greater than the amount of a control nucleic acid hybridized to, or associated with, the nucleic acid probe or primer. In certain embodiments, the nucleic acid probe or primer RNA is substantially complementary (e.g., at least 80, 90, 95, 98, or 100% complementary) to a target nucleic acid or a group of target nucleic acids from a cell. In other embodiments, the probe or primer is homologous to multiple RNA or DNA molecules, such as RNA or DNA molecules from the same gene family. In other embodiments, the probe or primer is homologous to a large number of RNA or DNA molecules. In desirable embodiments, the probe or primer binds to nucleic acids which have polynucleotide sequences that differ in sequence at a position that corresponds to the position of a universal base in the probe or primer. Examples of control nucleic acids include nucleic acids with a random sequence or nucleic acids known to have little, if any, affinity for the nucleic acid probe or primer.

Desirably, the association constant ($K_a$) of the nucleic acid toward a complementary target molecule is higher than the association constant of the complementary strands of the double stranded target molecule. In some desirable embodiments, the melting temperature of a duplex between the nucleic acid and a complementary target molecule is higher than the melting temperature of the complementary strands of the double stranded target molecule.

Exemplary mammals that can be treated using the methods of the invention include humans, primates such as monkeys, animals of veterinary interest (e.g., cows, sheep, goats, buffalos, and horses), and domestic pets (e.g., dogs and cats). Exemplary cells in which one or more target genes can be silenced using the methods of the invention include invertebrate, plant, bacteria, yeast, and vertebrate (e.g., mammalian or human) cells.

With respect to the therapeutic methods of the invention, it is not intended that the administration of nucleic acids to a mammal be limited to a particular mode of administration, dosage, or frequency of dosing; the present invention contemplates all modes of administration, including oral, intraperitoneal, intramuscular, intravenous, intraarticular, intralesional, subcutaneous, or any other route sufficient to provide a dose adequate to prevent or treat a disease (e.g., a disease associated with the expression of a target nucleic acid that is silenced with a nucleic acid of the invention). One or more nucleic acids may be administered to the mammal in a single dose or multiple doses. When multiple doses are administered, the doses may be separated from one another by, for example, one week, one month, one year, or ten years. It is to be understood that, for any particular subject, specific dosage regimes should be adjusted over time according to the individual need and the professional judgment of the person administering or supervising the administration of the compositions.

Optimum dosages may vary depending on the relative potency of individual oligonucleotides, and can generally be estimated based on $EC_{50}$ values found to be effective in in vitro and in vivo animal models. In general, dosage is from 0.001 ug to 100 g per kg of body weight (e.g., 0.001 ug/kg to 1 g/kg), and may be given once or more daily, weekly, monthly or yearly, or even once every 2 to 20 years (U.S. Pat. No. 6,440,739). Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.001 ug to 100 g per kg of body weight (e.g., 0.001 ug/kg to 1 g/kg), once or more daily, to once every 20 years. If desired, conventional treatments may be used in combination with the nucleic acids of the present invention.

Suitable carriers include, but are not limited to, saline, buffered saline, dextrose, water, glycerol, ethanol, and combinations thereof. The composition can be adapted for the mode of administration and can be in the form of, for example, a pill, tablet, capsule, spray, powder, or liquid. In some embodiments, the pharmaceutical composition contains one or more pharmaceutically acceptable additives suitable for the selected route and mode of administration. These compositions may be administered by, without limitation, any parenteral route including intravenous, intraarterial, intramuscular, subcutaneous, intradermal, intraperitoneal, intrathecal, as well as topically, orally, and by mucosal routes of delivery such as intranasal, inhalation, rectal, vaginal, buccal, and sublingual. In some embodiments, the pharmaceutical compositions of the invention are prepared for administration to vertebrate (e.g., mammalian) subjects in the form of liquids, including sterile, nonpyrogenic liquids for injection, emulsions, powders, aerosols, tablets, capsules, enteric coated tablets, or suppositories.

By "antisense nucleic acid" is meant a nucleic acid, regardless of length, that is complementary to a coding strand or mRNA of interest. In some embodiments, the antisene molecule inhibits the expression of only one nucleic acid, and in other embodiments, the antisense molecule inhibits the expression of more than one nucleic acid. Desirably, the antisense nucleic acid decreases the expression or biological activity of a nucleic and or encoded protein by at least 20, 40, 50, 60, 70, 80, 90, 95, or 100%. An antisense molecule can be introduced, e.g., to an individual cell or to whole animals, for example, it may be introduced systemically via the bloodstream. Desirably, a region of the antisense nucleic acid or the entire antisense nucleic acid is at least 70, 80, 90, 95, 98, or 100% complimentary to a coding sequence, regulatory region (5' or 3' untranslated region), or an mRNA of interest. Desirably, the region of complementarity includes at least 5, 10, 20, 30, 50, 75, 100, 200, 500, 1000, 2000 or 5000 nucleotides or includes all of the nucleotides in the antisense nucleic acid.

In some embodiments, the antisense molecule is less than 200, 150, 100, 75, 50, or 25 nucleotides in length. In other embodiments, the antisense molecule is less than 50,000; 10,000; 5,000; or 2,000 nucleotides in length. In certain embodiments, the antisense molecule is at least 200, 300, 500, 1000, or 5000 nucleotides in length. In some embodiments, the number of nucleotides in the antisense molecule is contained in one of the following ranges: 5–15 nucleotides, 16–20 nucleotides, 21–25 nucleotides, 26–35 nucleotides, 36–45 nucleotides, 46–60 nucleotides, 61–80 nucleotides, 81–100 nucleotides, 101–150 nucleotides, or 151–200 nucleotides, inclusive. In addition, the antisense molecule may contain a sequence that is less than a full-length sequence or may contain a full-length sequence.

By "double stranded nucleic acid" is meant a nucleic acid containing a region of two or more nucleotides that are in a double stranded conformation. In various embodiments, the double stranded nucleic acids consists entirely of LNA units or a mixture of LNA units, ribonucleotides, and/or deoxynucleotides. The double stranded nucleic acid may be a single molecule with a region of self-complimentarity such that nucleotides in one segment of the molecule base pair with nucleotides in another segment of the molecule. Alternatively, the double stranded nucleic acid may include two different strands that have a region of complimentarity to each other. Desirably, the regions of complimentarily are at least 70, 80, 90, 95, 98, or 100% complimentary. Desirably, the region of the double stranded nucleic acid that is present in a double stranded conformation includes at least 5, 10, 20, 30, 50, 75, 100, 200, 500, 1000, 2000 or 5000 nucleotides or includes all of the nucleotides in the double stranded nucleic acid. Desirable double stranded nucleic acid molecules have a strand or region that is at least 70, 80, 90, 95, 98, or 100% identical to a coding region or a regulatory sequence (e.g., a transcription factor binding site, a promoter, or a 5' or 3' untranslated region) of a nucleic acid of interest. In some embodiments, the double stranded nucleic acid is less than 200, 150, 100, 75, 50, or 25 nucleotides in length. In other embodiments, the double stranded nucleic acid is less than 50,000; 10,000; 5,000; or 2,000 nucleotides in length. In certain embodiments, the double stranded nucleic acid is at least 200, 300, 500, 1000, or 5000 nucleotides in length. In some embodiments, the number of nucleotides in the double stranded nucleic acid is contained in one of the following ranges: 5–15 nucleotides, 16–20 nucleotides, 21–25 nucleotides, 26–35 nucleotides, 36–45 nucleotides, 46–60 nucleotides, 61–80 nucleotides, 81–100 nucleotides, 101–150 nucleotides, or 151–200 nucleotides, inclusive. In addition, the double stranded nucleic acid may contain a sequence that is less than a full-length sequence or may contain a full-length sequence.

In some embodiments, the double stranded nucleic acid inhibits the expression of only one nucleic acid, and in other embodiments, the double stranded nucleic acid molecule inhibits the expression of more than one nucleic acid. Desirably, the nucleic acid decreases the expression or biological activity of a nucleic acid of interest or a protein encoded by a nucleic acid of interest by at least 20, 40, 50, 60, 70, 80, 90, 95, or 100%. A double stranded nucleic acid can be introduced, e.g., to an individual cell or to whole animals, for example, it may be introduced systemically via the bloodstream.

In various embodiments, the double stranded nucleic acid or antisense molecule includes one or more LNA nucleotides, one or more universal bases, and/or one or more modified nucleotides in which the 2' position in the sugar contains a halogen (such as flourine group) or contains an alkoxy group (such as a methoxy group) which increases the half-life of the double stranded nucleic acid or antisense molecule in vitro or in vivo compared to the corresponding double stranded nucleic acid or antisense molecule in which the corresponding 2' position contains a hydrogen or an hydroxyl group. In yet other embodiments, the double stranded nucleic acid or antisense molecule includes one or more linkages between adjacent nucleotides other than a naturally-occurring phosphodiester linkage. Examples of such linkages include phosphoramide, phosphorothioate, and phosphorodithioate linkages. Desirably, the double strandwd or antisense molecule is purified.

By "purified" is meant separated from other components that naturally accompany it. Typically, a factor is substantially pure when it is at least 50%, by weight, free from proteins, antibodies, and naturally-occurring organic molecules with which it is naturally associated. Desirably, the factor is at least 75%, more desirably, at least 90%, and most desirably, at least 99%, by weight, pure. A substantially pure factor may be obtained by chemical synthesis, separation of the factor from natural sources, or production of the factor in a recombinant host cell that does not naturally produce the factor. Nucleic acids and proteins may be purified by one skilled in the art using standard techniques such as those described by Ausubel et al. (Current Protocols in Molecular Biology, John Wiley & Sons, New York, 2000). The factor is desirably at least 2, 5, or 10 times as pure as the starting material, as measured using polyacrylamide gel electrophoresis, column chromatography, optical density, HPLC analysis, or western analysis (Ausubel et al., supra). Desirable methods of purification include immunoprecipitation, column chromatography such as immunoaffinity chromatography, magnetic bead immunoaffinity purification, and panning with a plate-bound antibody.

By "treating, stabilizing, or preventing a disease, disorder, or condition" is meant preventing or delaying an initial or subsequent occurrence of a disease, disorder, or condition; increasing the disease-free survival time between the disappearance of a condition and its reoccurrence; stabilizing or reducing an adverse symptom associated with a condition; or inhibiting or stabilizing the progression of a condition. Desirably, at least 20, 40, 60, 80, 90, or 95% of the treated subjects have a complete remission in which all evidence of the disease disappears. In another desirable embodiment, the length of time a patient survives after being diagnosed with a condition and treated with a nucleic acid of the invention is at least 20, 40, 60, 80, 100, 200, or even 500% greater than (i) the average amount of time an untreated patient survives or (ii) the average amount of time a patient treated with another therapy survives.

By "treating, stabilizing, or preventing cancer" is meant causing a reduction in the size of a tumor, slowing or preventing an increase in the size of a tumor, increasing the disease-free survival time between the disappearance of a tumor and its reappearance, preventing an initial or subsequent occurrence of a tumor, or reducing an adverse symptom associated with a tumor. In one desirable embodiment, the number of cancerous cells surviving the treatment is at least 20, 40, 60, 80, or 100% lower than the initial number of cancerous cells, as measured using any standard assay. Desirably, the decrease in the number of cancerous cells induced by administration of a nucleic acid of the invention (e.g., a nucleic acid with substantial complementarily to a nucleic acid associated with cancer such as an oncogne) is at least 2, 5, 10, 20, or 50-fold greater than the decrease in the number of non-cancerous cells. In yet another desirable embodiment, the number of cancerous cells present after administration of a nucleic acid of the invention is at least 2, 5, 10, 20, or 50-fold lower than the number of cancerous cells present prior to the administration of the compound or after administration of a buffer control. Desirably, the methods of the present invention result in a decrease of 20, 40, 60, 80, or 100% in the size of a tumor as determined using standard methods. Desirably, at least 20, 40, 60, 80, 90, or 95% of the treated subjects have a complete remission in which all evidence of the cancer disappears. Desirably, the cancer does not reappear or reappears after at least 5, 10, 15, or 20 years.

Exemplary cancers that can be treated, stabilized, or prevented using the above methods include prostate cancers, breast cancers, ovarian cancers, pancreatic cancers, gastric cancers, bladder cancers, salivary gland carcinomas, gastrointestinal cancers, lung cancers, colon cancers, melanomas, brain tumors, leukemias, lymphomas, and carcinomas. Benign tumors may also be treated or prevented using the methods and nucleic acids of the present invention.

By "infection" is meant the invasion of a host animal by a pathogen (e.g., a bacteria, yeast, or virus). For example, the infection may include the excessive growth of a pathogen that is normally present in or on the body of an animal or growth of a pathogen that is not normally present in or on the animal. More generally, aninfection can be any situation in which the presence of a pathogen population(s) is damaging to a host. Thus, an animal is "suffering" from an infection when an excessive amount of a pathogen population is present in or on the animal's body, or when the presence of a pathogen population(s) is damaging the cells or other tissue of the animal. In one embodiment, the number of a particular genus or species of paghogen is at least 2, 4, 6, or 8 times the number normally found in the animal.

At bacterial infection may be due to gram positive and/or gram negative bacteria. In desirable embodiments, the bacterial infection is due to one or more of the following bacteria: *Chlamydophila pneumoniae, C. psittaci, C. abortus, Chlamydia trachomatis, Simkania negevensis, Parachlamydia acanthamoebae, Pseudomonas aeruginosa, P. alcaligenes, P. chlororaphis, P. fluorescens, P. luteola, P. mendocina, P. monteilii, P. oryzihabitans, P. pertocinogena, P. pseudalcaligenes, P. putida, P. stutzeri, Burkholderia cepacia, Aeromonas hydrophilia, Escherichia coli, Citrobacter freundii, Salmonella typhimurium, S. typhi, S. paratyphi, S. enteritidis, Shigella dysenteriae, S. flexneri, S. sonnei, Enterobacter cloacae, E. aerogenes, Klebsiella pneumoniae, K. oxytoca, Serratia marcescens, Francisella tularensis, Morganella morganii, Proteus mirabilis, Proteus vulgaris, Providencia alcalifaciens, P. rettgeri, P. stuartii, Acinetobacter calcoaceticus, A. haemolyticus, Yersinia enterocolitica, Y. pestis, Y. pseudotuberculosis, Y. intermedia, Bordetella pertussis, B. parapertussis, B. bronchiseptica, Haemophilus influenzae, H. parainfluenzae, H. haemolyticus, H. parahaemolyticus, H. ducreyi, Pasteurella multocida, P. haemolytica, Branhamella catarrhalis, Helicobacter pylori, Campylobacter fetus, C. jejuni, C. coli, Borrelia burgdorferi, V. cholerae, V. parahaemolyticus, Legionella pneumophila, Listeria monocytogenes, Neisseria gonorrhea, N. meningitidis, Kingella dentrificans, K. kingae, K. oralis, Moraxella catarrhalis, M. atlantae, M. lacunata, M. nonliquefaciens, M. osloensis, M. phenylpyruvica, Gardnerella vaginalis, Bacteroides fragilis, Bacteroides distasonis, Bacteroides 3452A homology group, Bacteroides vulgatus, B. ovalus, B. thetaiotaomicron, B. uniformis, B. eggerthii, B. splanchnicus, Clostridium difficile, Mycobacterium tuberculosis, M. avium, M. intracellulare, M. leprae, C. diphtheriae, C. ulcerans, C. accolens, C. afermentans, C. amycolatum, C. argentorense, C. auris, C. bovis, C. confusum, C. coyleae, C. durum, C. falsenii, C. glucuronolyticum, C. imitans, C. jeikeium, C. kutscheri, C. kroppenstedtii, C. lipophilum, C. maeginleyi, C. matruchoti, C. mucifaciens, C. pilosum, C. propinquum, C. renale, C. riegelii, C. sanguinis, C. singulare, C. striatum, C. sundsvallense, C. thomssenii, C. urealyticum, C. xerosis, Streptococcus pneumoniae, S. agalactiae, S. pyogenes, Enterococcus avium, E. casseliflavus, E. cecorum, E. dispar, E. durans, E. faecalis, E. faecium, E. flavescens, E. gallinarum, E. hirae, E. malodoratus, E. mundtii, E. pseudoavium, E. raffinosus, E. solitarius, Staphylococcus aureus, S. epidermidis, S. saprophyticus, S. intermedius, S. hyicus, S. haemolyticus, S. hominis, and/or S. saccharolyticus.* Desirably, a nucleic acid is administered in an amount sufficient to prevent, stabilize, or inhibit the growth of a pathogenic bacteria or to kill the bacteria.

In various embodiments, the viral infection relevant to the methods of the invention is an infection by one or more of the following viruses: West Nile virus (e.g., Samuel, "Host genetic variability and West Nile virus susceptibility," Proc. Natl. Acad. Sci. USA Aug. 21, 2002; Beasley, Virology 296:17–23, 2002), Hepatitis, picomarirus, polio, HIV, coxsacchie, herpes simplex, St. Louis encephalitis s, Epstein-Barr, myxovirus, JC, coxsakievirus B, togavirus, measles, paramyxovirus, echovirus, bunyavirus, cytomegalovirus, varicella-zoster, mumps, equine encephalitis, lymphocytic choriomeningitis, rabies, simian virus 40, human polyoma virus, parvovirus, papilloma virus, primate adenovirus, and/or BK.

By "mammal in need of treatment" is meant a mammal in which a disease, disorder, or condition is treated, stabilized, or prevented by the administration of a nucleic acid of the invention.

By "mutation" is meant an alteration in a naturally-occurring or reference nucleic acid sequence, such as an insertion, deletion, frameshift mutation, silent mutation, nonsense mutation, or missense mutation. Desirably, the amino acid sequence encoded by the nucleic acid sequence has at least one amino acid alteration from a naturally-occurring sequence.

Other aspects of the invention are discussed infra.

BRIEF DESCRIPTION OF THE DRAWING

FIG. 2 is a table of the melting temperatures of various nucleic acids.

DETAILED DESCRIPTION OF THE INVENTION

Figure 1:
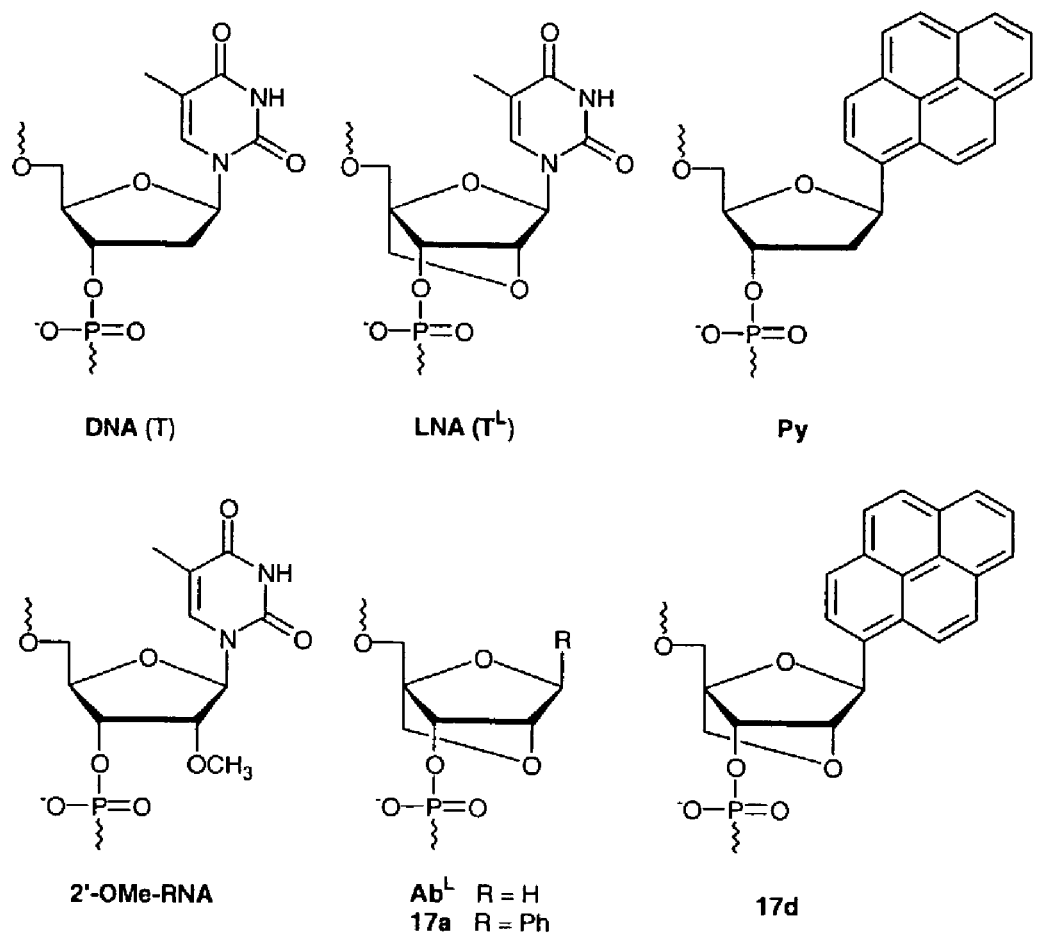
FIG. 1 shows the structures of selected nucleotide monomers: DNA (T), LNA ($T^L$), pyrene DNA (Py), 2'-OMe-RNA [2'-OMe(T)], abasic LNA ($Ab^L$), phenyl LNA (17a), and pyrenyl LNA (17d). The short notations shown are used in Table 1 and Table 2 or DNA, LNA and 2'-OMe-RNA, the thymine monomers are shown as examples.

The present invention relates to novel modified nucleic acid compositions with novel substitutions and their synthesis thereof. These nucleic acid composition are useful as universal bases and have a wide range of applications such as primers for PCR, sequencing primers for sequencing of unknown nucleic acids, detection of groups of base variants comprising the wild type genes as well as the mutations, and the like.

As discussed above, desirable modified bases contain one or more carbon alicyclic or carbocyclic aryl units, i.e. non-aromatic or aromatic cyclic units that contain only carbon atoms as ring members. Base groups that contain carbocyclic aryl groups are generally desirable, particularly a moiety that contains multiple linked aromatic groups, particularly groups that contain fused rings. That is, optionally substituted polynuclear aromatic groups are especially desirable such as optionally substituted naphthyl, optionally substituted anthracenyl, optionally substituted phenanthrenyl, optionally substituted pyrenyl, optionally substituted chrysenyl, optionally substituted benzanthracenyl, optionally substituted dibenzanthracenyl, optionally substituted benzopyrenyl, with substituted or unsubstituted pyrenyl being particularly desirable.

Without being bound by any theory, it is believed that such carbon alicyclic and/or carbocyclic aryl base groups can increase hydrophobic interaction with neighboring bases of an oligonucleotide. Those interactions can enhance the stability of a hybridized oligo pair, without necessity of interactions between bases of the distinct oligos of the hybridized pair.

Again without being bound by any theory, it is further believed that such hydrophobic interactions can be particularly favored by platelike stacking of neighboring bases, i.e. intercalation. Such intercalation will be promoted if the base comprises a moiety with a relatively planar extended structure, such as provided by an aromatic group, particularly a carbocyclic aryl group having multiple fused rings. This is indicated by the increases in $T_m$ values exhibited by oligos having LNA units with pyrenyl base groups relative to comparable oligos having LNA units with naphthyl base groups.

Modified (non-natural) nucleobases or nucleosidic bases that contain one or more heteroalicyclic or heteroaromatic groups also will be suitable for use in LNA units, particularly such non-aromatic and aromatic groups that contains one or more N, O or S atoms as ring members, particularly at least one sulfur atom, and from 5 to about 8 ring members. Also desirable is a base group that contains two or more fused rings, where at least one of the rings is a heteroalicyclic or heteroaromatic group containing 1, 2, or 3 N, O or S atoms as ring members.

Desirable modified nucleobases or nucleosidic bases covalently linked to the 1'-position of a furanosyl ring, particularly to the 1'-position of a 2',4'-linked furanosyl ring, especially to the 1'-position of a 2'-O,4'-C-methylene-beta-D-ribofuranosyl ring.

In general, desirable are nucleobases or nucleosidic bases that contain 2, 3, 4, 5, 6, 7 or 8 fused rings, which may be carbon alicyclic, heteroalicyclic, carbocyclic aryl and/or heteroaromatic; more desirably base groups that contain 3 to 6 fused rings, which may be carbon alicyclic, heteroalicyclic, carbocyclic aryl and/or heteroaromatic, and desirably the fused rings are each aromatic, particularly carbocyclic aryl.

In some embodiments, LNA unit has a carbon or hetero alicyclic ring with four to six ring members, and one or more of the alicyclic ring members form an additional cyclic linkage. Desirably, at least one of the alicyclic ring or the cyclic linkage contains at least one hetero atom ring member, such as at least one N, O, S or Se ring atom.

In some embodiments, the linkage comprises two adjacent alicyclic ring members. In some embodiments, the linkage has two alicyclic ring members that are not adjacent. Exemplary linkages include C-1', C-2'; C-2', C-3'; C-2', C-4'; and C-2', C-5' linkages. In some embodiments, the linkage has a total of from 3 to 6 atoms (e.g., 3 or 4 atoms) in addition to the alicyclic ring members. In some embodiments, the alicyclic group contains a single cyclic linkage or two cyclic linkages. In some embodiments, the nucleic acid has an LNA unit having a modified nucleobase or nucleosidic base other than oxazole or imidazole.

Less desirable and thus excluded from certain embodiments of the invention are optionally substituted oxazole base, particularly if used with an LNA group having a 2',4'-linkage, as well as optionally substituted imidazole and optionally substituted isoxazole base groups.

Other suitable base groups for use in LNA units in accordance with the invention include optionally substituted pyridyloxazole, optionally substituted pyrenylmethylglycerol, optionally substituted pyrrole, optionally substituted diazole and optionally substituted triazole groups.

As discussed above, typically desirable modified nucleobases or nucleosidic bases of the present invention when incorporated into an oligonucleotide containing all LNA units or a mixture of LNA and DNA or RNA units will exhibit substantially constant $T_m$ values upon hybridization with a complementary oligonucleotide, irrespective of the nucleobases or nucleosidic bases (natural) present on the complementary oligonucleotide.

In particular, typically desirable modified nucleobases or nucleosidic bases of the present invention when incorporated into a 9-mer oligonucleotide (all other eight residues or units being natural DNA or RNA units with natural bases) will exhibit a $T_m$ differential equal to or less than 15, 12, 10, 9, 8, 7, 6, 5, 4, 3 or 2° C. upon hybridizing to the four complementary oligonucleotide variants that are identical except for the unit corresponding to the LNA unit, where each variant has one of the natural bases uracil, cytosine, thymine, adenine or guanine. For such $T_m$ differentials, hybridization is conducted in a hybridization buffer of 10 mM sodium phosphate, 100 mM sodium chloride, 0.1 mM EDTA, pH 7.0 (see defined protocol of steps a) through d) below).

As referred to herein, a nucleic acid compound that has a $T_m$ differential of a specified amount (e.g., 15, 12, 10, 8, 6, 5, 4, 3, 2° C. or less) means the nucleic acid compound will exhibit that specified $T_m$ differential when incorporated into a specified 9-mer oligonucleotide with respect to the four complementary variants, as defined immediately below:

Unless otherwise indicated, as referred to herein, a $T_m$ value provided by a particular modified base is calculated by the following protocol (steps a) through d)):

a) incorporating the modified base of interest into the following oligonucleotide 5'-d(GTGAMATGC), wherein M is the modified base;

b) mixing $1.5 \times 10^{-6}$M of the oligonucleotide having incorporated therein the modified base with each of $1.5 \times 10^{-6}$M of the four oligonucleotides having the sequence 3'-d(CAC-TYTACG), wherein Y is A, C, G, T, respectively, in a buffer of 10 mM sodium phosphate, 100 mM sodium chloride, 0.1 mM EDTA, pH 7.0;

c) allowing the oligonucleotides to hybridize; and d) detecting the $T_m$ for each of the four hybridized nucleotides by heating the hybridized nucleotides and observing the temperature at which the maximum of the first derivative of the melting curve recorded at a wavelength of 260 nm is obtained.

Unless otherwise indicated, as referred to herein, a $T_m$ differential for a particular modified base is determined by subtracting the highest $T_m$ value determined in steps a) through d) immediately above from the lowest $T_m$ value determined by steps a) through d) immediately above.

In one aspect, the invention provides oligonucleotides comprising at least ten nucleosides, at least two of which are selected from the group consisting of A, T, C and G, and at least one nucleoside being a universal nucleoside. The incorporation of one or more universal nucleosides into the oligomer makes bonding to unknown bases possible and allows the oligonucleotide to match ambiguous or unknown nucleic acid sequences. In one desirable aspect, all of the common DNA nucleosides—deoxyadenosine (A), thymidine (T), deoxycytidine (C) and deoxyguanosine (G)—are combined with at least one of the universal (modified base) nucleosides to make an oligonucleotide having between about five to 100 nucleosides therein.

In another aspect of the invention, all of the common RNA nucleosides or commonly used derivatives thereof, such as 2'-O-methyl, 2'-fluoro, 2'-allyl, and 2'-O-methoxyethoxy derivatives are combined with at least one of the universal (modified base) nucleosides to make an oligonucleotide having between about five to 100 nucleosides therein.

Modified nucleic acid compounds may comprise a variety of nucleic acid units e.g. nucleoside and/or nucleotide units. As discussed above, an LNA nucleic acid unit has a carbon or hetero alicyclic ring with four to six ring members, e.g. a furanose ring, or other alicyclic ring structures such as a cyclopentyl, cycloheptyl, tetrahydropyranyl, oxepanyl, tetrahydrothiophenyl, pyrrolidinyl, thianyl, thiepanyl, piperidinyl, and the like.

In an aspect of the invention, at least one ring atom of the carbon or hetero alicyclic group is taken to form a further cyclic linkage to thereby provide a multi-cyclic group. The cyclic linkage may include one or more, typically two atoms, of the carbon or hetero alicyclic group. The cyclic linkage also may include one or more atoms that are substituents, but not ring members, of the carbon or hetero alicyclic group.

Unless indicated otherwise, an alicyclic group as referred to herein is inclusive of group having all carbon ring members as well as groups having one or more hetero atom (e.g. N, O, S or Se) ring members. The disclosure of the group as a "carbon or hetero alicyclic group" further indicates that the alicyclic group may contain all carbon ring members (i.e. a carbon alicyclic) or may contain one or more hetero atom ring members (i.e. a hetero alicyclic). Alicyclic groups are understood not to be aromatic, and typically are fully saturated within the ring (i.e. no endocyclic multiple bonds).

Desirably, the alicyclic ring is a hetero alicyclic, i.e. the alicyclic group has one or more hetero atoms ring members, typically one or two hetero atom ring members such as O, N, S or Se, with oxygen being often desirable.

The one or more cyclic linkages of an alicyclic group may be comprised completely of carbon atoms, or generally more desirable, one or more hetero atoms such as O, S, N or Se, desirably oxygen for at least some embodiments. The cyclic linkage will typically contain one or two or three hetero atoms, more typically one or two hetero atoms in a single cyclic linkage.

The one or more cyclic linkages of a nucleic acid compound of the invention can have a number of alternative configurations and/or configurations. For instance, cyclic linkages of nucleic acid compounds of the invention will include at least one alicyclic ring atom. The cyclic linkage may be disubstituted to a single alicyclic atom, or two adjacent or non-adjacent alicyclic ring atoms may be included in a cyclic linkage. Still further, a cyclic linkage may include a single alicyclic ring atom, and a further atom that is a substituent but not a ring member of the alicyclic group.

For instance, as discussed above, if the alicyclic group is a furanosyl-type ring, desirable cyclic linkages include the following: C-1', C-2'; C-2', C-3'; C-2', C-4'; or a C-2', C-5' linkage.

A cyclic linkage will typically comprise, in addition to the one or more alicyclic group ring atoms, 2 to 6 atoms in addition to the alicyclic ring members, more typically 3 or 4 atoms in addition to the alicyclic ring member(s).

The alicyclic group atoms that are incorporated into a cyclic linkage are typically carbon atoms, but hetero atoms such as nitrogen of the alicyclic group also may be incorporated into a cyclic linkage.

It is understood that references herein to a nucleic acid unit or residue or LNA residue or similar term are inclusive of individual LNA, nucleoside, and nucleotide units and inclusive of LNA, nucleoside units, and nucleotide units within an oligonucleotide.

As used herein, "universal base" or "modified base" or other similar term generally refers to a composition (e.g., a non-natural composition) such as a nucleobase or nucleosidic base which can pair with a natural base (i.e. adenine, guanine, cytosine, uracil, and/or thymine), desirably without discrimination. Desirably, the modified base provides a $T_m$ differential of 15, 12, 10, 8, 6, 5, 4, 3, 2° C. or less or as disclosed above.

Specifically desirable modified nucleic acids for use oligonucleotides of the invention include locked nucleic acids as disclosed in WO99/14226 (which include bicyclic and tricyclic DNA or RNA having a 2'-4' or 2'-3' sugar linkages); 2'-deoxy-2'-fluoro ribonucleotides; 2'-O-methyl ribonucleotides; 2'-O-methoxyethyl ribonucleotides; peptide nucleic acids; 5-propynyl pyrimidine ribonucleotides; 7-deazapurine ribonucleotides; 2,6-diaminopurine ribonucleotides; and 2-thio-pyrimidine ribonucleotides.

By "LNA unit" is meant an individual LNA monomer (e.g., an LNA nucleoside or LNA nucleotide) or an oligomer (e.g., an oligonucleotide or nucleic acid) that includes at least one LNA monomer. LNA units as disclosed in WO 99/14226 are in general particularly desirable modified nucleic acids for incorporation into an oligonucleotide of the invention. Additionally, the nucleic acids may be modified at either the 3' and/or 5' end by any type of modification known in the art. For example, either or both ends may be capped with a protecting group, attached to a flexible linking group, attached to a reactive group to aid in attachment to the substrate surface, etc. Desirable LNA units also are disclosed in WO 0056746, WO 0056748, and WO 0066604.

As disclosed in WO 99/14226, LNA are a novel class of DNA analogues that form DNA- or RNA-heteroduplexes with exceptionally high thermal stability. LNA units include bicyclic compounds as shown immediately below where ENA refers to 2'O,4'C-ethylene-bridged nucleic acids:

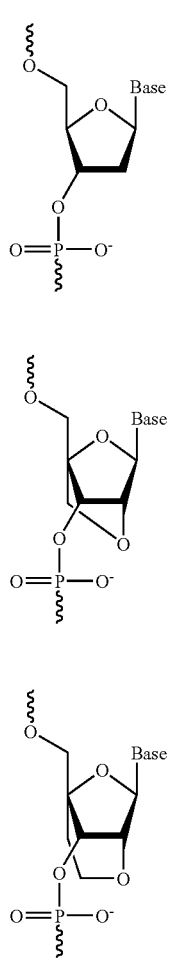

References herein to Locked Nucleoside Analogues, LNA units, LNA residues, LNA monomers, or similar terms are inclusive of such compounds as disclosed in WO 99/14226, WO 00/56746, WO 00/56748, and WO 00/66604.

Desirable LNA units can share chemical properties of DNA and RNA; they are water soluble, can be separated by agarose gel electrophoresis, can be ethanol precipitated, etc.

Desirable LNA units include nucleoside units having a 2'-4' cyclic linkage, as described in the International Patent Application WO 99/14226, WO 00/56746, WO 00/56748, and WO 00/66604. Desirable LNA unit structures are exemplified in the formula Ia and Ib below. In formula Ia the configuration of the furanose is denoted D-β, and in formula Ib the configuration is denoted L-α. Configurations which are composed of mixtures of the two, e.g. D-β and L-α, are also included.

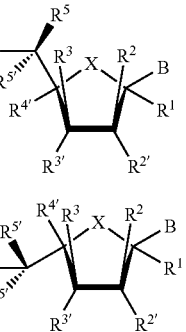

In Ia and Ib, X is oxygen, sulfur and carbon; B is a universal or modified base (particularly non-natural occurring nucleobase or nucleosidic base) e.g. pyrene and pyridyloxazole derivatives, pyrenyl, 5-nitroindole, hypoxanthine, pyrrole, pyrenylmethylglycerol moieties, all of which may be optionally substituted. Other desirable universal bases include, pyrrole, diazole or triazole moieties, all of which may be optionally substituted, and other groups e.g. modified adenine, cytosine, 5-methylcytosine, isocytosine, pseudoisocytosine, guanine, thymine, uracil, 5-bromouracil, 5-propynyluracil, 5-propyny-6-fluoroluracil, 5-methylthiazoleuracil, 6-aminopurine, 2-aminopurine, inosine, diaminopurine, 7-propyne-7-deazaadenine, 7-propyne-7-deazaguanine. $R^1$, $R^2$ or $R^{2'}$, $R^3$ or $R^{3'}$, $R^5$ and $R^{5'}$ are hydrogen, methyl, ethyl, propyl, propynyl, aminoalkyl, methoxy, propoxy, methoxy-ethoxy, fluoro, or chloro. P designates the radical position for an internucleoside linkage to a succeeding monomer, or a 5'-terminal group, $R^3$ or $R^{3'}$ is an internucleoside linkage to a preceding monomer, or a 3'-terminal group. The internucleotide linkage may be a phosphate, phosphorothioate, phosphorodithioate, phosphoramidate, phosphoroselenoate, phosphorodiselenoate, alkylphosphotriester, or methyl phosphornate. The internucleotide linkage may also contain non-phosphorous linkers, hydroxylamine derivatives (e.g. —CH$_2$—NCH$_3$—O—CH$_2$—), hydrazine derivatives, e.g. —CH$_2$—NCH$_3$—NCH$_3$—CH$_2$, amid derivatives, e.g. —CH$_2$—CO—NH—CH$_2$—, —CH$_2$—NH—CO—CH$_2$—. In Ia, $R^{4'}$ and $R^{2'}$ together designate —CH$_2$—O—, —CH$_2$—S—, —CH$_2$—NH—, —CH$_2$—NMe- , —CH$_2$—CH$_2$—O—, —CH$_2$—CH$_2$—S—, —CH$_2$—CH$_2$—NH—, or —CH$_2$—CH$_2$—NMe- where the oxygen, sulfur or nitrogen, respectively, is attached to the 2'-position. In Formula Ib, $R^{4'}$ and $R^2$ together designate —CH$_2$—O—, —CH$_2$—S—, —CH$_2$—NH—, —CH$_2$—NMe- , —CH$_2$—CH$_2$—O—, —CH$_2$—CH$_2$—S—, —CH$_2$—CH$_2$—NH—, or —CH$_2$—CH$_2$—NMe- , where the oxygen, sulphur or nitrogen, respectively, is attached to the 2-position ($R^2$ configuration). Exemplary 5' and/or 3' terminal groups include —H, —OH, —SH, halo (e.g., chloro, fluoro, iodo, or bromo), optionally substituted aryl, (e.g., phenyl or benzyl), alkyl (e.g, methyl or ethyl), alkoxy (e.g., methoxy), acyl (e.g. acetyl or benzoyl), aroyl, aralkyl, hydroxy, hydroxyalkyl, alkoxy, aryloxy, aralkoxy, nitro, cyano, carboxy, alkoxycarbonyl, aryloxycarbonyl, aralkoxycarbonyl, acylamino, aroylamine, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio,amidino, amino, carbamoyl, sulfamoyl, alkene, alkyne, protecting groups (e.g., silyl, 4,4'-dimethoxytrityl, monomethoxytrityl, or trityl (triphenylmethyl)), linkers (e.g., a linker containing an amine, ethylene glycol, quinone such as anthraquinone), detectable labels (e.g., radiolabels or fluorescent labels), and biotin.

Most desirable LNA unit structures are structures in which X is oxygen (Formula Ia, Ib); B is a universal base such as pyrene; $R^1$, $R^2$ or $R^{2'}$, $R^3$ or $R^{3'}$, $R^5$ and $R^{5'}$ are hydrogen; P is a phosphate, phosphorothioate, phosphorodithioate, phosphoramidate, and methyl phosphomates; $R^3$ or $R^{3'}$ is an internucleoside linkage to a preceding monomer, or a 3'-terminal group. In Formula Ia, $R^{4'}$ and $R^{2'}$ together designate —$CH_2$—O—, —$CH_2$—S—, —$CH_2$—NH—, —$CH_2$—NMe—, —$CH_2$—$CH_2$—O—, —$CH_2$—$CH_2$—S—, —$CH_2$—$CH_2$—NH—, or —$CH_2$—$CH_2$—NMe—, where the oxygen, sulphur or nitrogen, respectively, is attached to the 2'-position, and in Formula Ib, $R^{4'}$ and $R^2$ together designate —$CH_2$—O—, —$CH_2$—S—, —$CH_2$—NH—, —$CH_2$—NMe—, —$CH_2$—$CH_2$—O—, —$CH_2$—$CH_2$—S—, —$CH_2$—$CH_2$—NH—, or —$CH_2$—$CH_2$—NMe—, where the oxygen, sulphur or nitrogen, respectively, is attached to the 2'-position in the $R^2$ configuration.

Introduction of LNA units with natural bases into either DNA, RNA or pure LNA oligonucleotides can result in extremely high thermal stability of duplexes with complimentary DNA or RNA, while at the same time obeying the Watson-Crick base pairing rules. In general, the thermal stability of heteroduplexes is increased 3–8° C. per LNA unit in the duplex. Oligonucleotides containing LNA can be designed to be substrates for polymerases (e.g. Taq polymerase), and PCR based on LNA primers is more discriminatory towards single base mutations in the template DNA compared to normal DNA-primers (i.e. allele specific PCR). Furthermore, very short LNA oligos (e.g. 8-mers) which have high $T_m$'s when compared to similar DNA oligos, can be used as highly specific catching probes with outstanding discriminatory power towards single base mutations (i.e. SNP detection).

As used herein, the term "$T_m$" is used in reference to the "melting temperature". The melting temperature is the temperature at which 50% of a population of double-stranded nucleic acid molecules becomes dissociated into single strands. The equation for calculating the $T_m$ of nucleic acids is well-known in the art. The $T_m$ of a hybrid nucleic acid is often estimated using a formula adopted from hybridization assays in 1 M salt, and commonly used for calculating $T_m$ for PCR primers: $T_m$=[(number of A+T)×2° C.+(number of G+C)×4° C.]. C. R. Newton et al. PCR, 2nd Ed., Springer-Verlag (New York: 1997), p. 24. This formula was found to be inaccurate for primers longer that 20 nucleotides. Id. Other more sophisticated computations exist in the art which take structural as well as sequence characteristics into account for the calculation of $T_m$. A calculated $T_m$ is merely an estimate; the optimum temperature is commonly determined empirically. Herein $T_m$ is determined, e.g. as described in Example 18 below by detecting the $T_m$ for each of the four hybridized nucleotides by heating the hybridized nucleotides and observing the temperature at which the maximum of the first derivative of the melting curve recorded at a wavelength of 260 nm is obtained.

The term "homology", as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous."

When used in reference to a double-stranded nucleic acid sequence such as a cDNA or genomic clone, the term "substantially homologous", as used herein, refers to a probe that can hybridize to a strand of the double-stranded nucleic acid sequence under conditions of low stringency, e.g. using a hybridization buffer comprising 20% formamide in 0.8M saline/0.08M sodium citrate (SSC) buffer at a temperature of 37° C. and remaining bound when subject to washing once with that SSC buffer at 37° C.

When used in reference to a single-stranded nucleic acid sequence, the term "substantially homologous", as used herein, refers to a probe that can hybridize to (i.e., is the complement of) the single-stranded nucleic acid template sequence under conditions of low stringency, e.g. using a hybridization buffer comprising 20% formamide in 0.8M saline/0.08M sodium citrate (SSC) buffer at a temperature of 37° C. and remaining bound when subject to washing once with that SSC buffer at 37° C.

Oligonucleotides containing LNA are readily synthesized by standard phosphoramidite chemistry. The flexibility of the phosphoramidite synthesis approach further facilitates the easy production of LNA oligos carrying all types of standard linkers, fluorophores and reporter groups.

Particularly desirable LNA units for incorporation into an oligonucleotide of the invention include those of the following formula IIa

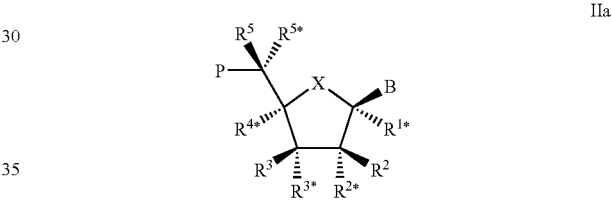

wherein X oxygen, sulfur, nitrogen, substituted nitrogen, carbon and substituted carbon, and desirably is oxygen; B is a modified base as discussed above e.g. an optionally substituted carbocyclic aryl such as optionally substituted pyrene or optionally substituted pyrenylmethylglycerol, or an optionally substituted heteroalicylic or optionally substituted heteroaromatic such as optionally substituted pyridyloxazole. Other desirable universal bases include, pyrrole, diazole or triazole moieties, all of which may be optionally substituted; $R^{1*}$, $R^2$, $R^3$, $R^5$ and $R^{5*}$ are hydrogen; P designates the radical position for an internucleoside linkage to a succeeding monomer, or a 5'-terminal group, $R^{3*}$ is an internucleoside linkage to a preceding monomer, or a 3'-terminal group; and $R^{2*}$ and $R^{4*}$ together designate —O—$CH_2$— or —O—$CH_2$—$CH_2$—, where the oxygen is attached in the 2'-position, or a linkage of $(CH_2)_n$— where n is 2, 3 or 4, desirably 2, or a linkage of —S—$CH_2$— or —NH—$CH_2$—.

Units of formula IIa where $R^{2*}$ and $R^{4*}$ contain oxygen are sometimes referred to herein as "oxy-LNA"; units of formula Ia where $R^{2*}$ and $R^{4*}$ contain sulfur are sometimes referred to herein as "thio-LNA"; and units of formula Ia where $R^{2*}$ and $R^{4*}$ contain nitrogen are sometimes referred to herein as "amino-LNA". For many applications, oxy-LNA units are desirable modified nucleic acid units of the invention.

As used herein, including with respect to formula IIa, the term "nucleobase" or "base unit" covers the naturally occurring nucleobases adenine (A), guanine (G), cytosine (C), thymine (T) and uracil (U) as well as non-naturally occurring nucleobases such as xanthine, diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-($C^3$–$C^6$)-alkynyl-cytosine, 5-fluorouracil, 5-bromouracil, pseudoisocytosine, 2-hydroxy-5-methyl-4-triazolopyridin, isocytosine, isoguanine, inosine and the "non-naturally occurring" nucleobases described in Benner et al., U.S. Pat. No. 5,432,272 and Susan M. Freier and Karl-Heinz Altmann, Nucleic Acids Research, 1997, vol. 25, pp 4429–4443. The term "nucleobase" thus includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., Angewandte Chemie, International Edition, 1991, 30, 613–722 (see especially pages 622 and 623, and in the Concise Encyclopedia of Polymer Science and Engineering, J. I. Kroschwitz Ed., John Wiley & Sons, 1990, pages 858–859, Cook, Anti-Cancer Drug Design 1991, 6, 585–607, each of which are hereby incorporated by reference in their entirety). The term "nucleosidic base" or "base unit" is further intended to include compounds such as heterocyclic compounds that can serve like nucleobases including certain "universal bases" that are not nucleosidic bases in the most classical sense but serve as nucleosidic bases. Especially mentioned as universal bases are 3-nitropyrrole, optionally substituted indoles (e.g., 5-nitroindole), and optionally substituted hypoxanthine. Other desirable compounds include pyrene and pyridyloxazole derivatives, pyrenyl, pyrenylmethylglycerol derivatives and the like. Other desirable universal bases include, pyrrole, diazole or triazole derivatives, including those universal bases known in the art.

As indicated above, various groups of an LNA unit may be optionally substituted. A "substituted" group such as a nucleobase or nucleosidic base and the like may be substituted by other than hydrogen at one or more available positions, typically 1 to 3 or 4 positions, by one or more suitable groups such as those disclosed herein. Suitable groups that may be present on a "substituted" group include e.g. halogen such as fluoro, chloro, bromo and iodo; cyano; hydroxyl; nitro; azido; alkanoyl such as a $C_{1-6}$ alkanoyl group such as acyl and the like; carboxamido; alkyl groups including those groups having 1 to about 12 carbon atoms, or 1, 2, 3, 4, 5, or 6 carbon atoms; alkenyl and alkynyl groups including groups having one or more unsaturated linkages and from 2 to about 12 carbon, or 2, 3, 4, 5 or 6 carbon atoms; alkoxy groups including those having one or more oxygen linkages and from 1 to about 12 carbon atoms, or 1, 2, 3, 4, 5 or 6 carbon atoms; aryloxy such as phenoxy; alkylthio groups including those moieties having one or more thioether linkages and from 1 to about 12 carbon atoms, or 1, 2, 3, 4, 5 or 6 carbon atoms; alkylsulfinyl groups including those moieties having one or more sulfinyl linkages and from 1 to about 12 carbon atoms, or 1, 2, 3, 4, 5, or 6 carbon atoms; alkylsulfonyl groups including those moieties having one or more sulfonyl linkages and from 1 to about 12 carbon atoms, or 1, 2, 3, 4, 5, or 6 carbon atoms; aminoalkyl groups such as groups having one or more N atoms and from 1 to about 12 carbon atoms, or 1, 2, 3, 4, 5 or 6 carbon atoms; carbocyclic aryl having 6 or more carbons; aralkyl having 1 to 3 separate or fused rings and from 6 to about 18 carbon ring atoms, with benzyl being a desirable group; aralkoxy having 1 to 3 separate or fused rings and from 6 to about 18 carbon ring atoms, with O-benzyl being a desirable group; or a heteroaromatic or heteroalicyclic group having 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

The chimeric oligonucleotides of the present invention desirably comprise a mixture of non-modified nucleic acids and modified (non-natural) nucleic acids. In the following discussion, the term "oligonucleotides" will interchangeably be referred to as "oligonucleotides comprising universal (modified) bases". The use of this term is for convenience only, to avoid repetition of the enumeration of the possible configurations for this method, and it is intended that each of the embodiments described below may be used in combination with any probe/target configurations (e.g., labeled probes and captured target DNA and vice versa).

"LNA-universal base conjugate" refers to a LNA unit that contains a covalently attached universal base (e.g., a compound of formula 1a or 1b). Examples of universal bases are described herein.

It should be clear to the person skilled in the art that various nucleobases which previously have been considered "non-naturally occurring" have subsequently been found in nature.

Desirable syntheses of pyrene-LNA units are shown in the following Schemes 1 and 2. In the below Schemes 1 and 2, the compound reference numerals are also referred to in the examples below.

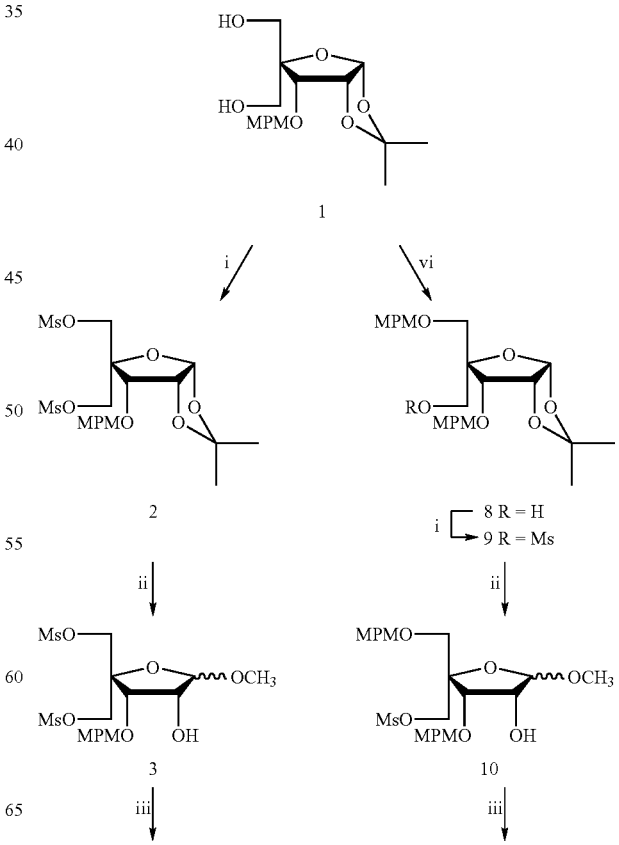

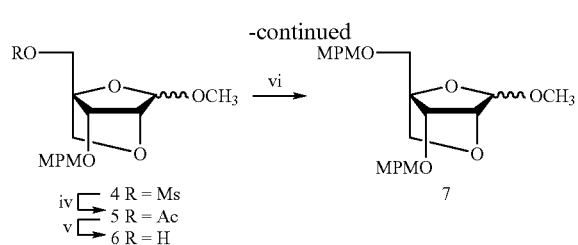

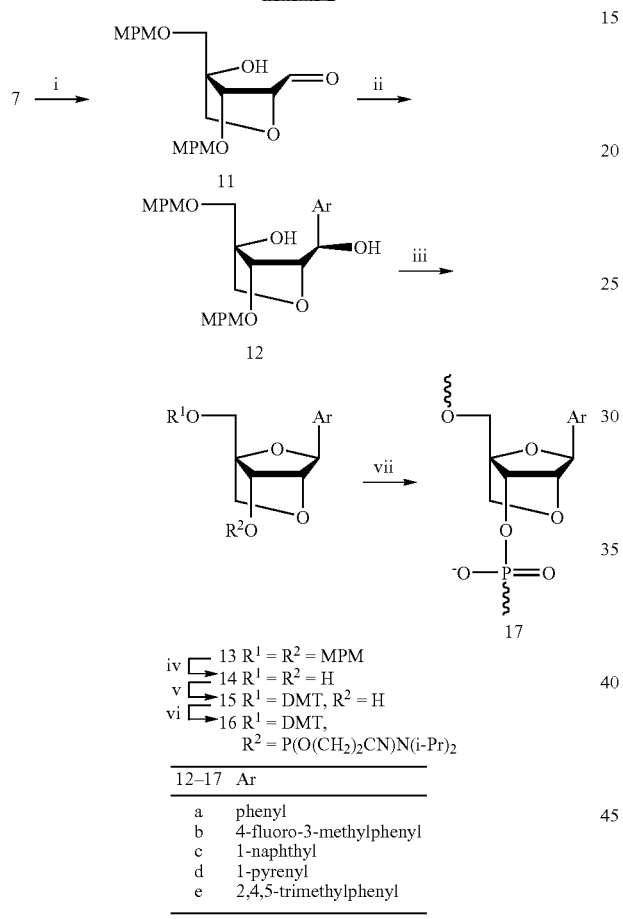

| 12–17 | Ar |
|---|---|
| a | phenyl |
| b | 4-fluoro-3-methylphenyl |
| c | 1-naphthyl |
| d | 1-pyrenyl |
| e | 2,4,5-trimethylphenyl |

A "non-oxy-LNA" monomer or unit is broadly defined as any nucleoside (i.e. a glycoside of a heterocyclic base) which does not contain an oxygen atom in a 2'-4'-sugar linkage. Examples of non-oxy-LNA units include 2'-deoxynucleotides (DNA) or nucleotides (RNA) or any analogues of these units which are not oxy-LNA, such as for example the thio-LNA and amino-LNA described above with respect to formula 1a and in Singh et al. J. Org. Chem. 1998, 6, 6078–9, and the derivatives described in Susan M. Freier and Karl-Heinz Altmann, Nucleic Acids Research, 1997, vol 25, pp 4429–4443.

A wide variety of modified nucleic acids may be employed, including those that have 2'-modification of hydroxyl, 2'-O-methyl, 2'-fluoro, 2'-trifluoromethyl, 2'-O-(2-methoxyethyl), 2'-O-aminopropyl, 2'-O-dimethylaminooxyethyl, 2'-O-fluoroethyl or 2'-O-propenyl. The nucleic acid may further include a 3' modification, desirably where the 2'- and 3'-position of the sugar moiety (e.g., ribose or xylose) is linked. The nucleic acid also may contain a modification at the 4'-position, desirably where the 2'- and 4'-positions of the sugar moiety (e.g., ribose or xylose) are linked such as by a 2'-4' link of $-CH_2-S-$, $-CH_2-NH-$, or $-CH_2-NMe-$ bridge.

The nucleotide also may have a variety of configurations such as α-D-ribo, β-D-xylo, or α-L-xylo configuration.

The internucleoside linkages of the units of oligos of the invention may be natural phosphorodiester linkages, or other linkages such as $-O-P(O)_2-O-$, $-O-P(O,S)-O-$, $-O-P(S)_2-O-$, $-NR^H-P(O)_2-O-$, $-O-P(O,NR^H)-O-$, $-O-PO(R")-O-$, $-O-PO(CH_3)-O-$, and $-O-PO(NHR^N)-O-$, where $R^H$ is selected from hydrogen and $C_{1-4}$-alkyl, and R" is selected from $C_{1-6}$-alkyl and phenyl.

A further desirable group of modified nucleic acids for incorporation into oligomers of the invention include those of the following formula:

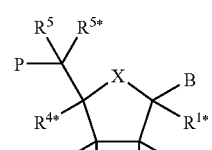

I wherein X is $-O-$; B is a modified base as discussed above e.g. an optionally substituted carbocyclic aryl such as optionally substituted pyrene or optionally substituted pyrenylmethylglycerol, or an optionally substituted heteroalicylic or optionally substituted heteroaromatic such as optionally substituted pyridyloxazole. Other desirable universal bases include, pyrrole, diazole or triazole moieties, all of which may be optionally substituted;

$R^{1*}$ is hydrogen;

P designates the radical position for an internucleoside linkage to a succeeding monomer, or a 5'-terminal group, such internucleoside linkage or 5'-terminal group optionally including the substituent $R^5$, $R^5$ being hydrogen or included in an internucleoside linkage, $R^{3*}$ is a group P* which designates an internucleoside linkage to a preceding monomer, or a 3'-terminal group;

one or two pairs of non-geminal substituents selected from the present substituents of $R^2$, $R^{2*}$, $R^3$, $R^{4*}$, may designate a biradical consisting of 1–4 groups/atoms selected from $-C(R^aR^b)-$, $-C(R^a)=C(R^a)-$, $-C(R^a)=N-$, $-O-$, $-S-$, $-SO_2-$, $-N(R^a)-$, and $>C=Z$, wherein Z is selected from $-O-$, $-S-$, and $-N(R^a)-$, and $R^a$ and $R^b$ each is independently selected from hydrogen, optionally substituted $C_{1-6}$-alkyl, optionally substituted $C_{2-6}$-alkenyl, hydroxy, $C_{1-6}$-alkoxy, $C_{2-6}$-alkenyloxy, carboxy, $C_{1-6}$-alkoxycarbonyl, $C_{1-6}$-alkylcarbonyl, formyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, photochemically active groups, thermochemically active groups, chelating groups, reporter groups, and ligands, said possible pair of non-geminal substituents thereby forming a monocyclic entity together with (i) the atoms to which said non-geminal substituents are bound and (ii) any intervening atoms; and each of the substituents $R^2$, $R^{2*}$, $R^3$, $R^{4*}$ which are present and not involved in the possible biradical is independently selected from hydrogen, optionally substituted $C_{1-6}$-alkyl, optionally substituted $C_{2-6}$-alkenyl, hydroxy, $C_{1-6}$-alkoxy, $C_{2-6}$-alkenyloxy, carboxy, $C_{1-6}$-alkoxycarbonyl, $C_{1-6}$-alkylcarbonyl, formyl, amino, mono- and di($C_{1-6}$-alkyl) amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, photochemically active groups, thermochemically active groups, chelating groups, reporter groups, and ligands; and basic salts and acid addition salts thereof.

Particularly desirable LNA units for use in oligonucleotides of the invention are 2'-deoxyribonucleotides, ribonucleotides, and analogues thereof that are modified at the 2'-position in the sugar moiety (e.g., ribose or xylose), such as 2'-O-methyl, 2'-fluoro, 2'-trifluoromethyl, 2'-O-(2-methoxyethyl), 2'-O-aminopropyl, 2'-O-dimethylamino-oxyethyl, 2'-O-fluoroethyl or 2'-O-propenyl, and analogues wherein the modification involves both the 2' and 3' position, desirably such analogues wherein the modifications links the 2'- and 3'-position in the sugar moiety (e.g., ribose or xylose), such as those described in Nielsen et al., J. Chem. Soc., Perkin Trans. 1, 1997, 3423–33, and in WO 99/14226, and analogues wherein the modification involves both the 2'- and 4'-position, desirably such analogues wherein the modifications links the 2'- and 4'-position in the sugar moiety (e.g., ribose or xylose), such as analogues having a —$CH_2$— S— or a —$CH_2$—NH— or a —$CH_2$—NMe- bridge (see Singh et al. J. Org. Chem. 1998, 6, 6078–9). Although LNA units having the β-D-ribo configuration are often the most applicable, other configurations also are suitable for purposes of the invention. Of particular use are α-L-ribo, the β-D-xylo and the α-L-xylo configurations (see Beier et al., Science, 1999, 283, 699 and Eschenmoser, Science, 1999, 284, 2118), in particular those having a 2'-4'-$CH_2$—S—, —$CH_2$—NH—, —$CH_2$—O— or —$CH_2$—NMe- bridge.

In the present context, the term "oligonucleotide" which is the same as "oligomer" which is the same as "oligo" means a successive chain of nucleoside monomers (e.g., glycosides of heterocyclic bases) connected via internucleoside linkages. The linkage between two successive monomers in the oligo consist of 2 to 4, desirably 3, groups/atoms selected from —$CH_2$—, —O—, —S—, —$NR^H$—, >C=O, >C=$NR^H$, >C=S, —Si(R")$_2$—, —SO—, —S(O)$_2$—, —P(O)$_2$—, —PO(BH$_3$)—, —P(O,S)—, —P(S)$_2$—, —PO(R")—, —PO(OCH$_3$)—, and —PO(NHR$^H$)—, where $R^H$ is selected from hydrogen and $C_{1-4}$-alkyl, and R" is selected from $C_{1-6}$-alkyl and phenyl. Illustrative examples of such linkages are —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH= (including $R^5$ when used as a linkage to a succeeding monomer), —$CH_2$—$CH_2$—O—, —$NR^H$—$CH_2$—$CH_2$—, —$CH_2$—$CH_2$—$NR^H$, —$CH_2$—$NR^H$—$CH_2$—, —O—$CH_2$—$CH_2$—$NR^H$, —$NR^H$—CO—O—, $NR^H$—CO—$NR^H$—, —$NR^H$—CS— $NR^H$—, —$NR^H$—C(=$NR^H$)—$NR^H$—, —$NR^H$—CO— $CH_2$—$NR^H$—, —O—CO—O—, —O—CO—$CH_2$—O—, —O—$CH_2$—CO—O—, —$CH_2$—CO—$NR^H$—, —O—CO—$NR^H$—, —$NR^H$—CO—$CH_2$—, —O—$CH_2$— CO—$NR^H$—, —O—$CH_2$—$CH_2$—$NR^H$—, —CH=N— O—, —$CH_2$—$NR^H$—O—, —$CH_2$—O—N= (including $R^5$ when used as a linkage to a succeeding monomer), —$CH_2$— O—$NR^H$—, —CO—$NR^H$—$CH_2$—, —$CH_2$—$NR^H$—O—, —$CH_2$—$NR^H$—CO—, —O—$NR^H$—$CH_2$—, —O—$NR^H$—, —O—$CH_2$—S—, —S—$CH_2$—O—, —$CH_2$—$CH_2$—S—, —O—$CH_2$—$CH_2$—S—, —S—$CH_2$—CH= (including $R^5$ when used as a linkage to a succeeding monomer), —S—$CH_2$—$CH_2$—, —S—$CH_2$— $CH_2$—O—, —S—$CH_2$—$CH_2$—S—, —$CH_2$—S—$CH_2$—, —$CH_2$—SO—$CH_2$—, —$CH_2$—SO$_2$—$CH_2$—, —O—SO— O—, —O—S(O)$_2$—O—, —O—S(O)$_2$—$CH_2$—, —O—S (O)$_2$—$NR^H$—, —$NR^H$—S(O)$_2$—$CH_2$—, —O—S(O)$_2$— $CH_2$—, —O—P(O)$_2$—O—, —O—P(O,S)—O—, —O—P (S)$_2$—O—, —S—P(O)$_2$—O—, —S—P(O,S)—O—, —S—P(S)$_2$—O —, —O—P(O)$_2$—S—, —O—P(O,S)— S—, —O—P(S)$_2$—S—, —S—P(O)$_2$—S—, —S—P(O, S)—S—, —S—P(S)$_2$—S—, —O—PO(R")—O—, —O—PO(OCH$_3$)—O—, —O—PO(OCH$_2$CH$_3$)—O—, —O—PO(OCH$_2$CH$_2$S—R)—O—, —O—PO(BH$_3$)—O—, —O—PO(NHR$^N$)—O—, —O—P(O)$_2$—$NR^H$—, —$NR^H$— P(O)$_2$—O—, —O—P(O,$NR^H$)—O—, —$CH_2$—P(O)$_2$— O—, —O—P(O)$_2$—$CH_2$—, and —O—Si(R")$_2$—O—; among which —$CH_2$—CO—$NR^H$—, —$CH_2$—$NR^H$—O—, —S—$CH_2$—O—, —O—P(O)$_2$—O—, —O—P(O,S)— O—, —O—P(S)$_2$—O—, —$NR^H$—P(O)$_2$—O—, —O—P (O,$NR^H$)—O—, —O—PO(R")—O—, —O—PO(CH$_3$)— O—, and —O—PO(NHR$^N$)—O—, where $R^H$ is selected form hydrogen and $C_{1-4}$-alkyl, and R" is selected from $C_{1-6}$-alkyl and phenyl, are especially desirable. Further illustrative examples are given in Mesmaeker et. al., Current Opinion in Structural Biology 1995, 5, 343–355 and Susan M. Freier and Karl-Heinz Altmann, Nucleic Acids Research, 1997, vol 25, pp 4429–4443. The left-hand side of the internucleoside linkage is bound to the 5-membered ring as substituent P* at the 3'-position, whereas the right-hand side is bound to the 5'-position of a preceding monomer.

The term "succeeding monomer" relates to the neighboring monomer in the 5'-terminal direction and the "preceding monomer" relates to the neighboring monomer in the 3'-terminal direction.

Monomers are referred to as being "complementary" if they contain nucleobases that can form hydrogen bonds according to Watson-Crick base-pairing rules (e.g. G with C, A with T or A with U) or other hydrogen bonding motifs such as for example diaminopurine with T, inosine with C, pseudoisocytosine with G, etc.

In the practice of the present invention, target genes may be suitably single-stranded or double-stranded DNA or RNA; however, single-stranded DNA or RNA targets are desirable. It is understood that the target to which the LNA-nucleoside conjugates of the invention are directed include allelic forms of the targeted gene and the corresponding mRNAs including splice variants. There is substantial guidance in the literature for selecting particular sequences for LNA-nucleoside conjugates given a knowledge of the sequence of the target polynucleotide, e.g., Peyman and Ulmann, *Chemical Reviews,* 90:543–584, 1990; Crooke, *Ann. Rev. Pharmacol. Toxicol.,* 32:329–376 (1992); and Zamecnik and Stephenson, Proc. Natl. Acad. Sci., 75:280–284 (1974). Desirable mRNA targets include the 5' cap site, tRNA primer binding site, the initiation codon site, the mRNA donor splice site, and the mRNA acceptor splice site, e.g., Goodchild et al., U.S. Pat. No. 4,806,463.

As used herein, the term "corresponding unmodified reference nucleoside" refers to a nucleoside that is not conjugated to LNA and is in the same orientation as the nucleoside in the LNA-universal base conjugate.

As used herein, the term "corresponding unmodified reference nucleobase" refers to a nucleobase that is not conjugated to LNA and is in the same orientation as the nucleobase in the LNA-universal base conjugate.

A further aspect of the invention is the use of different LNA units such as for example a nucleic acid with one or more oxy-LNA, thio-LNA or amino-LNA units.

The use of such different monomers offers a means to "fine tune" the chemical, physical, biological, pharmacokinetic and pharmacological properties of the nucleoside thereby facilitating improvement in their safety and efficacy profiles when used as a therapeutic drug.

An "LNA modified oligonucleotide" is used herein to describe oligonucleotides comprising at least one LNA unit of the general scheme A, described infra, having the below described illustrative examples of modifications:

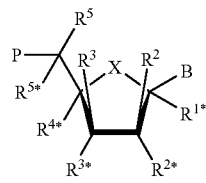

A wherein X is selected from —O—, —S—, —N($R^N$)—, —C($R^6R^{6*}$)—, —O—C($R^7R^{7*}$)—, —C($R^6R^{6*}$)—O—, —S—C($R^7R^{7*}$)—, —C($R^6R^{6*}$)—S—, —N($R^{N*}$)—C($R^7R^{7*}$)—, —C($R^6R^6$)—N($R^{N*}$)—, and —C($R^6R^{6*}$)—C($R^7R^{7*}$)—;

B is selected from a modified base as discussed above e.g. an optionally substituted carbocyclic aryl such as optionally substituted pyrene or optionally substituted pyrenylmethylglycerol, or an optionally substituted heteroalicylic or optionally substituted heteroaromatic such as optionally substituted pyridyloxazole, optionally substituted pyrrole, optionally substituted diazole or optionally substituted triazole moieties; hydrogen, hydroxy, optionally substituted $C_{1-4}$-alkoxy, optionally substituted $C_{1-4}$-alkyl, optionally substituted $C_{1-4}$-acyloxy, nucleobases, DNA intercalators, photochemically active groups, thermochemically active groups, chelating groups, reporter groups, and ligands;

P designates the radical position for an internucleoside linkage to a succeeding monomer, or a 5'-terminal group, such internucleoside linkage or 5'-terminal group optionally including the substituent $R^5$;

one of the substituents $R^2$, $R^{2*}$, $R^3$, and $R^{3*}$ is a group P* which designates an internucleoside linkage to a preceding monomer, or a 2'/3'-terminal group.

the substituents of $R^{1*}$, $R^{4*}$, $R^5$, $R^{5*}$, $R^6$, $R^{6*}$, $R^7$, $R^{7*}$, $R^N$, and the ones of $R^2$, $R^{2*}$, $R^3$, and $R^{3*}$ not designating P* each designates a biradical comprising about 1–8 groups/atoms selected from —C($R^aR^b$)—, —C($R^a$)=C($R^a$)—, —C($R^a$)=N—, —C($R^a$)—O—, —O—, —Si($R^a$)$_2$—, —C($R^a$)—S—, —S—, —SO$_2$—, —C($R^a$)—N($R^b$)—, —N($R^a$)—, and >C=Q, wherein Q is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents $R^a$ and $R^b$ together may designate optionally substituted methylene (=CH$_2$), and wherein two non-geminal or geminal substituents selected from $R^a$, $R^b$, and any of the substituents $R^{1*}$, $R^2$, $R^{2*}$, $R^3$, $R^{3*}$, $R^{4*}$, $R^5$, $R^{5*}$, $R^{6*}$ and $R^7$, and $R^{7*}$ which are present and not involved in P, P* or the biradical(s) together may form an associated biradical selected from biradicals of the same kind as defined before;

the pair(s) of non-geminal substituents thereby forming a mono- or bicyclic entity together with (i) the atoms to which said non-geminal substituents are bound and (ii) any intervening atoms; and each of the substituents $R^{1*}$, $R^2$, $R^{2*}$, $R^3$, $R^{4*}$, $R^5$, $R^{5*}$, $R^6$ and $R^{6*}$, $R^7$, and $R^{7*}$ which are present and not involved in P, P* or the biradical(s), is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1–5 carbon atom(s) alkylene chain which is optionally interrupted and/or terminated by one or more heteroatoms/groups selected from —O—, —S—, and —(N$R^N$)— where $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl; and basic salts and acid addition salts thereof.

Exemplary 5', 3', and/or 2' terminal groups include —H, —OH, halo (e.g., chloro, fluoro, iodo, or bromo), optionally substituted aryl, (e.g., phenyl or benzyl), alkyl (e.g, methyl or ethyl), alkoxy (e.g., methoxy), acyl (e.g. acetyl or benzoyl), aroyl, aralkyl, hydroxy, hydroxyalkyl, alkoxy, aryloxy, aralkoxy, nitro, cyano, carboxy, alkoxycarbonyl, aryloxycarbonyl, aralkoxycarbonyl, acylamino, aroylamine, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio,amidino, amino, carbamoyl, sulfamoyl, alkene, alkyne, protecting groups (e.g., silyl, 4,4'-dimethoxytrityl, monomethoxytrityl, or trityl (triphenylmethyl)), linkers (e.g., a linker containing an amine, ethylene glycol, quinone such as anthraquinone), detectable labels (e.g., radiolabels or fluorescent labels), and biotin.

In another desirable embodiment, LNA modified oligonucleotides used in this invention comprises oligonucleotides containing at least one LNA unit of the general scheme A above:

wherein X, B, P are defined as above;
one of the substituents $R^2$, $R^{2*}$, $R^3$, and $R^{3*}$ is a group P* which designates an internucleoside linkage to a preceding monomer, or a 2'/3'-terminal group;
two of the substituents of $R^{1*}$, $R^2$, $R^{2*}$, $R^3$, $R^{3*}$, $R^5$, $R^{5*}$, $R^6$, $R^{6*}$, $R^7$, and $R^{7*}$ when taken together designate a biradical structure selected from $-(CR^*R^*)_r\text{-}M\text{-}(CR^*R^*)_s-$, $-(CR^*R^*)_r-M-(CR^*R^*)_s-M-$, -M-$(CR^*R^*)_{r+s}$-M-, -M-$(CR^*R^*)_r$-M-$(CR^*R^*)_s-$, $(CR^*R^*)_{r+s}$, -M-, -M-M-, wherein each M is independently selected from $-O-$, $-S-$, $-Si(R^*)_2-$, $-N(R^*)-$, $>C=O$, $-C(=O)-N(R^*)-$, and $-N(R^*)-C(=O)-$. Each R* and $R^{1(1*)}-R^{7(7*)}$, which are not involved in the biradical, are independently selected from hydrogen, halogen, azido, cyano, nitro, hydroxy, mercapto, amino, mono- or di($C_{1-6}$-alkyl) amino, optionally substituted $C_{1-6}$-alkoxy, optionally substituted $C_{1-6}$-alkyl, DNA intercalators, photochemically active groups, thermochemically active groups, chelating groups, reporter groups, and ligands, and/or two adjacent (non-geminal) R* may together designate a double bond, and each of r and s is 0–4 with the proviso that the sum r+s is 1–5.

Examples of LNA units are shown in scheme B:

Scheme B

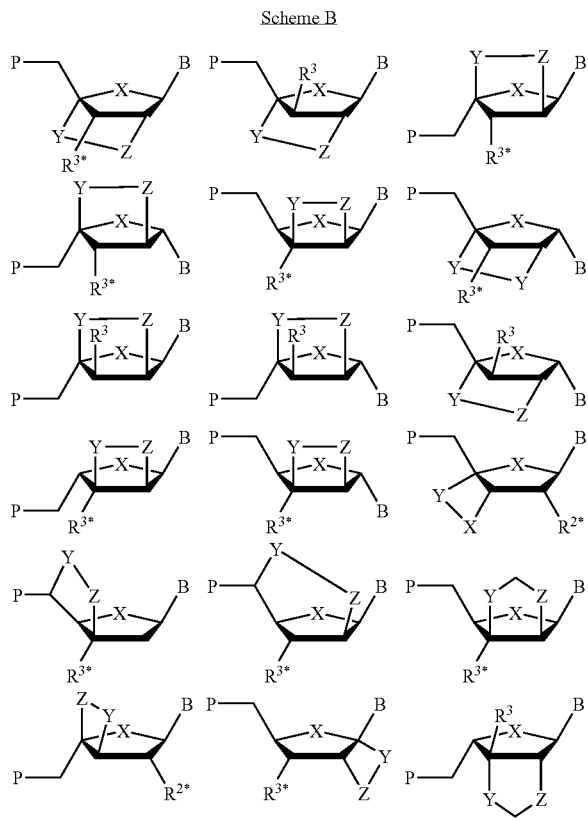

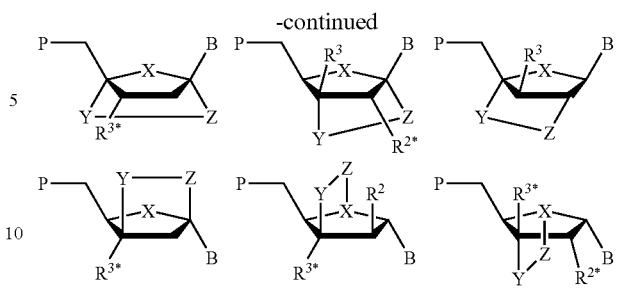

-continued wherein the groups, X and B are defined as above.

P designates the radical position for an internucleoside linkage to a succeeding monomer, nucleoside such as an L-nucleoside, or a 5'-terminal group, such internucleoside linkage or 5'-terminal group optionally including the substituent $R^5$;

one of the substituents $R^2$, $R^{2*}$, $R^3$, and $R^{3*}$ is a group P* which designates an internucleoside linkage to a preceding monomer, or a 2'/3'-terminal group. Exemplary 5', 3', and/or 2' terminal groups include those described above.

Desirable nucleosides are L-nucleosides such as for example, derived dinucleoside monophosphates. The nucleoside can be comprised of either a beta-D, a beta-L or an alpha-L nucleoside. Desirable nucleosides may be linked as dimers wherein at least one of the nucleosides is a beta-L or alpha-L. B may also designate the pyrimidine bases cytosine, thymine, uracil, or 5-fluorouridine (5-FUdR) other 5-halo compounds, or the purine bases, adenosine, guanosine or inosine.

In some embodiments, the LNA-pyrene is in a position corresponding to the position of a non-base (e.g., a unit without a base) in another nucleic acid, such as a target nucleic acid. Incorporation of pyrene in a DNA strand that is hybridized against the four natural bases decreases the $T_m$ by −4.5° C. to −6.8° C.; however, incorporation of pyrene in a DNA strand in a position opposite a non-base only decreases the $T_m$ by −2.3° C. to −4.6° C., most likely due to the better accomodation of the pyrene in the B-type duplex (Matray and Kool, J. Am. Chem. Soc. 120, 6191, 1998). Thus, incorporation on LNA-pyrene into a nucleic acid in a position opposite a non-base (e.g., a unit without a base or a unit with a small group such as a noncyclic group instead of a base) in a target nucleic acid may also minimize any potential decrease in $T_m$ due to the pyrene substitution The chimeric oligos of the present invention are highly suitable for a variety of diagnostic purposes such as for the isolation, purification, amplification, detection, identification, quantification, or capture of nucleic acids such as DNA, mRNA or non-protein coding cellular RNAs, such as tRNA, rRNA, snRNA and scRNA, or synthetic nucleic acids, in vivo or in vitro.

The oligomer can comprise a photochemically active group, a thermochemically active group, a chelating group, a reporter group, or a ligand that facilitates the direct or indirect detection of the oligomer or the immobilization of the oligomer onto a solid support. Such group are typically attached to the oligo when it is intended as a probe for in situ hybridization, in Southern hybridization, Dot blot hybridization, reverse Dot blot hybridization, or in Northern hybridization.

When the photochemically active group, the thermochemically active group, the chelating group, the reporter group, or the ligand includes a spacer (K), the spacer may suitably comprise a chemically cleavable group.

In the present context, the term "photochemically active groups" covers compounds which are able to undergo chemical reactions upon irradiation with light. Illustrative examples of functional groups hereof are quinones, especially 6-methyl-1,4-naphtoquinone, anthraquinone, naphtoquinone, and 1,4-dimethyl-anthraquinone, diazirines, aromatic azides, benzophenones, psoralens, diazo compounds, and diazirino compounds.

In the present context "thermochemically reactive group" is defined as a functional group which is able to undergo thermochemically-induced covalent bond formation with other groups. Illustrative examples of functional parts thermochemically reactive groups are carboxylic acids, carboxylic acid esters such as activated esters, carboxylic acid halides such as acid fluorides, acid chlorides, acid bromide, and acid iodides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, and boronic acid derivatives.

In the present context, the term "chelating group" means a molecule that contains more than one binding site and frequently binds to another molecule, atom or ion through more than one binding site at the same time. Examples of functional parts of chelating groups are iminodiacetic acid, nitrilotriacetic acid, ethylenediamine tetraacetic acid (EDTA), aminophosphonic acid, etc.

In the present context, the term "reporter group" or "detectable label" means a group which is detectable either by itself or as a part of an detection series. Examples of functional parts of reporter groups are biotin, digoxigenin, fluorescent groups (groups which are able to absorb electromagnetic radiation, e.g. light or X-rays, of a certain wavelength, and which subsequently reemits the energy absorbed as radiation of longer wavelength; illustrative examples are dansyl (5-dimethylamino)-1-naphthalene-sulfonyl), DOXYL (N-oxyl-4,4-dimethyloxazolidine), PROXYL (N-oxyl-2,2,5,5-tetra-methylpyrrolidine), TEMPO (N-oxyl-2,2,6,6-tetramethylpiperidine), dinitrophenyl, acridines, coumarins, Cy3 and Cy5 (trademarks for Biological Detection Systems, Inc.), erythrosine, coumaric acid, umbelliferone, Texas red, rhodamine, tetramethyl rhodamine, Rox, 7-nitrobenzo-2-oxa-1-diazole (NBD), pyrene, fluorescein, Europium, Ruthenium, Samarium, and other rare earth metals), radioisotopic labels, chemiluminescence labels (labels that are detectable via the emission of light during a chemical reaction), spin labels (a free radical (e.g. substituted organic nitroxides) or other paramagnetic probes (e.g. $Cu^{2+}$, $Mg^{2+}$) bound to a biological molecule being detectable by the use of electron spin resonance spectroscopy), enzymes (such as peroxidases, alkaline phosphatases, β-galactosidases, and glycose oxidases), antigens, antibodies, haptens (groups which are able to combine with an antibody, but which cannot initiate an immune response by itself, such as peptides and steroid hormones), carrier systems for cell membrane penetration such as: fatty acid residues, steroid moieties (cholesteryl), vitamin A, vitamin D, vitamin E, folic acid peptides for specific receptors, groups for mediating endocytose, epidermal growth factor (EGF), bradykinin, and platelet derived growth factor (PDGF). Especially interesting examples are biotin, fluorescein, Texas Red, rhodamine, dinitrophenyl, digoxigenin, Ruthenium, Europium, Cy5, Cy3, etc.

In the present context "ligand" means something which binds. Ligands can comprise functional groups such as aromatic groups (such as benzene, pyridine, naphthalene, anthracene, and phenanthrene), heteroaromatic groups (such as thiophene, furan, tetrahydrofuran, pyridine, dioxane, and pyrimidine), carboxylic acids, carboxylic acid esters, carboxylic acid halides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, $C_1$-$C_{20}$ alkyl groups optionally interrupted or terminated with one or more heteroatoms such as oxygen atoms, nitrogen atoms, and/or sulphur atoms, optionally containing aromatic or mono/polyunsaturated hydrocarbons, polyoxyethylene such as polyethylene glycol, oligo/polyamides such as poly-α-alanine, polyglycine, polylysine, peptides, oligo/polysaccharides, oligo/polyphosphates, toxins, antibiotics, cell poisons, and steroids, and also "affinity ligands", i.e. functional groups or biomolecules that have a specific affinity for sites on particular proteins, antibodies, poly- and oligosaccharides, and other biomolecules.

It should be understood that the above-mentioned specific examples under DNA intercalators, photochemically active groups, thermochemically active groups, chelating groups, reporter groups, and ligands correspond to the "active/functional" part of the groups in question. For the person skilled in the art it is furthermore clear that DNA intercalators, photochemically active groups, thermochemically active groups, chelating groups, reporter groups, and ligands are typically represented in the form M-K- where M is the "active/functional" part of the group in question and where K is a spacer through which the "active/functional" part is attached to the 5- or 6-membered ring. Thus, it should be understood that the group B, in the case where B is selected from DNA intercalators, photochemically active groups, thermochemically active groups, chelating groups, reporter groups, and ligands, has the form M-K-, where M is the "active/functional" part of the DNA intercalator, photochemically active group, thermochemically active group, chelating group, reporter group, and ligand, respectively, and where K is an optional spacer comprising 1–50 atoms, desirably 1–30 atoms, in particular 1–15 atoms, between the 5- or 6-membered ring and the "active/functional"part.

In the present context, the term "spacer" means a thermochemically and photochemically non-active distance-making group and is used to join two or more different moieties of the types defined above. Spacers are selected on the basis of a variety of characteristics including their hydrophobicity, hydrophilicity, molecular flexibility and length (e.g. see Hermanson et. al., "Immobilized Affinity Ligand Techniques", Academic Press, San Diego, Calif. (1992), p. 137-ff). Generally, the length of the spacers are less than or about 400 Å, in some applications desirably less than 100 Å. The spacer, thus, comprises a chain of carbon atoms optionally interrupted or terminated with one or more heteroatoms, such as oxygen atoms, nitrogen atoms, and/or sulphur atoms. Thus, the spacer K may comprise one or more amide, ester, amino, ether, and/or thioether functionalities, and optionally aromatic or mono/polyunsaturated hydrocarbons, polyoxyethylene such as polyethylene glycol, oligo/polyamides such as poly-α-alanine, polyglycine, polylysine, and peptides in general, oligosaccharides, oligo/polyphosphates. Moreover the spacer may consist of combined units thereof. The length of the spacer may vary, taking into consideration the desired or necessary positioning and spatial orientation of the "active/functional" part of the group in question in relation to the 5- or 6-membered ring. In particularly interesting embodiments, the spacer includes a chemically cleavable group. Examples of such chemically cleavable groups include disulphide groups cleavable under reductive conditions, peptide fragments cleavable by peptidases, etc.

Modified nucleobases and nucleosidic bases may comprise a cyclic unit (e.g. a carbocyclic unit such as pyrenyl) that is joined to a nucleic unit, such as a 1'-position of furasonyl ring through a linker, such as a straight of branched chain alkylene or alkenylene group. Alkylene groups suitably having from 1 (i.e. —$CH_2$—) to about 12 carbon atoms, more typically 1 to about 8 carbon atoms, still more typically 1 to about 6 carbon atoms. Alkenylene groups suitably have one, two or three carbon-carbon double bounds and from 2 to about 12 carbon atoms, more typically 2 to about 8 carbon atoms, still more typically 2 to about 6 carbon atoms.

As discussed above, oligonucleotides of the invention may be used in high specificity oligo arrays e.g. wherein a multitude of different oligos are affixed to a solid surface in a predetermined pattern (*Nature Genetics*, suppl. vol. 21, January 1999, 1–60 and WO 96/31557). The usefulness of such an array, which can be used to simultaneously analyze a large number of target nucleic acids, depends to a large extend on the specificity of the individual oligos bound to the surface. The target nucleic acids may carry a detectable label or be detected by incubation with suitable detection probes which may also be an oligonucleotide of the invention.

An additional object of the present invention is to provide oligonucleotides which combines an increased ability to discriminate between complementary and mismatched targets with the ability to act as substrates for nucleic acid active enzymes such as for example DNA and RNA polymerases, ligases, phosphatases. Such oligonucleotides may be used for instance as primers for sequencing nucleic acids and as primers in any of the several well known amplification reactions, such as the PCR reaction.

In a further aspect, oligonucleotides of the invention may be used to construct new affinity pairs with exhibit enhanced specificity towards each other. The affinity constants can easily be adjusted over a wide range and a vast number of affinity pairs can be designed and synthesized. One part of the affinity pair can be attached to the molecule of interest (e.g. proteins, amplicons, enzymes, polysaccharides, antibodies, haptens, peptides, etc.) by standard methods, while the other part of the affinity pair can be attached to e.g. a solid support such as beads, membranes, micro-titer plates, sticks, tubes, etc. The solid support may be chosen from a wide range of polymer materials such as for instance polypropylene, polystyrene, polycarbonate or polyethylene. The affinity pairs may be used in selective isolation, purification, capture and detection of a diversity of the target molecules.

Oligonucleotides of the invention also may be employed as probes in the purification, isolation and detection of for instance pathogenic organisms such as viral, bacteria, and fungi. Oligonucleotides of the invention also may be used as generic tools for the purification, isolation, amplification and detection of nucleic acids from groups of related species such as for instance rRNA from gram-positive or gram negative bacteria, fungi, mammalian cells, etc.

Oligonucleotides of the invention also may be employed as an aptamer in molecular diagnostics, e.g. in RNA mediated catalytic processes, in specific binding of antibiotics, drugs, amino acids, peptides, structural proteins, protein receptors, protein enzymes, saccharides, polysaccharides, biological cofactors, nucleic acids, or triphosphates or in the separation of enantiomers from racemic mixtures by stereospecific binding.

Oligonucleotides of the invention also may be used for labeling of cells, e.g., in methods wherein the label allows the cells to be separated from unlabelled cells.

Oligonucleotides also may be conjugated by forming a covalent bond or non-covalent bond to a compound selected from proteins, amplicons, enzymes, polysaccharides, antibodies, haptens, and peptides. Desirably, the oligonucleotide has a fluorophore moiety and a quencher moiety, positioned in such a way that the hybridized state of the oligonucleotide can be distinguished from the unbound state of the oligonucleotide by a change in the fluorescent signal from the nucleotide. Other desirable oligonucleotides are adapted for use as a Taqman probe or Molecular Beacon.

Kits are also provided containing one or more oligonucleotides of the invention for the isolation, purification, amplification, detection, identification, quantification, or capture of natural or synthetic nucleic acids. The kit typically will contain a reaction body, e.g. a slide or biochip. One or more oligonucleotides of the invention may be suitably immobilized on such a reaction body.

The invention also provides methods for using kits of the invention for carrying out a variety of bioassays. Any type of assay wherein one component is immobilized may be carried out using the substrate platforms of the invention. Bioassays utilizing an immobilized component are well known in the art. Examples of assays utilizing an immobilized component include for example, immunoassays, analysis of protein-protein interactions, analysis of protein-nucleic acid interactions, analysis of nucleic acid-nucleic acid interactions, receptor binding assays, enzyme assays, phosphorylation assays, diagnostic assays for determination of disease state, genetic profiling for drug compatibility analysis, SNP detection, etc.

Identification of a nucleic acid sequence capable of binding to a biomolecule of interest can be achieved by immobilizing a library of nucleic acids onto the substrate surface so that each unique nucleic acid was located at a defined position to form an array. The array would then be exposed to the biomolecule under conditions which favored binding of the biomolecule to the nucleic acids. Non-specifically binding biomolecules could be washed away using mild to stringent buffer conditions depending on the level of specificity of binding desired. The nucleic acid array would then be analyzed to determine which nucleic acid sequences bound to the biomolecule. Desirably the biomolecules would carry a fluorescent tag for use in detection of the location of the bound nucleic acids.

Assay using an immobilized array of nucleic acid sequences may be used for determining the sequence of an unknown nucleic acid; single nucleotide polymorphism (SNP) analysis; analysis of gene expression patterns from a particular species, tissue, cell type, etc.; gene identification; etc.

As discussed above, oligonucleotides of the invention may be used for therapeutic applications, e.g. as an antisense, double stranded nucleic acid (e.g., RNAi agent), antigene, or ribozyme therapeutic agents. In these therapeutic methods, one or more oligonucleotides of the invention is administered as desired to a patient suffering from or susceptible the targeted disease or disorder, e.g., a viral infection.

The oligonucleotides used in the methods of the present invention may be used without any prior analysis of the structure assumed by a target nucleic acid. For any given case, it can be determined empirically using appropriately selected reference target molecule whether a chosen probe or array of probes can distinguish between genetic variants sufficiently for the needs of a particular assay. Once a probe or array of probes is selected, the analysis of which probes bind to a target, and how efficiently these probes bind (i.e., how much of probe/target complex can be detected) allows a hybridization signature of the conformation of the target to be created. It is contemplated that the signature may be stored, represented or analyzed by any of the methods commonly used for the presentation of mathematical and physical information, including but not limited to line, pie, or area graphs or 3-dimensional topographic representations. The data may also be used as a numerical matrix, or any other format that may be analyzed either visually, mathematically or by computer-assisted algorithms, such as for example EURAYdesign™ software and/or neural networks.

The resulting signatures of the nucleic acid structures serve as sequence-specific identifiers of the particular molecule, without requiring the determination of the actual nucleotide sequence. While specific sequences may be identified by comparison of their signature to a reference signature, the use of algorithms to deduce the actual sequence of a molecule by sequence-specific hybridization (i.e., at high stringency to eliminate the influence of secondary and tertiary structures) to a complete matrix (i.e., probes that shift by a single nucleotide position at each location of an array), is not a feature or requirement, or within the bounds of the methods of the present invention.

It is also contemplated that information on the structures assumed by a target nucleic acid may be used in the design of the probes, such that regions that are known or suspected to be involved in folding may be chosen as hybridization sites. Such an approach will reduce the number of probes that are likely to be needed to distinguish between targets of interest.

There are many methods used to obtain structural information involving nucleic acids, including the use of chemicals that are sensitive to the nucleic acid structure, such as phenanthroline/copper, EDTA-$Fe^{2+}$, cisplatin, ethylnitrosourea, dimethyl pyrocarbonate, hydrazine, dimethyl sulfate, and bisulfite. Enzymatic probing using structure-specific nucleases from a variety of sources, such as the Cleavase™ enzymes (Third Wave Technologies, Inc., Madison, Wis.), Taq DNA polymerase, *E. coli* DNA polymerase I, and eukaryotic structure-specific endonucleases (e.g., human, murine and Xenopus XPG enzymes, yeast RAD2 enzymes), murine FEN-1 endonucleases (Harrington and Lieber, Genes and Develop., 3:1344 [1994]) and calf thymus 5' to 3' exonuclease (Murante et al., J. Biol. Chem., 269:1191 [1994]). In addition, enzymes having 3' nuclease activity such as members of the family of DNA repair endonucleases (e.g., the RrpI enzyme from Drosophila melanogaster, the yeast RAD1/RAD10 complex and *E. coli* Exo III), are also suitable for examining the structures of nucleic acids.

If analysis of structure as a step in probe selection is to be used for a segment of nucleic acid for which no information is available concerning regions likely to form secondary structures, the sites of structure-induced modification or cleavage must be identified. It is most convenient if the modification or cleavage can be done under partially reactive conditions (i.e., such that in the population of molecules in a test sample, each individual will receive only one or a few cuts or modifications). When the sample is analyzed as a whole, each reactive site should be represented, and all the sites may be thus identified. Using a Cleavase Fragment Length Polymorphism™ cleavage reaction as an example, when the partial cleavage products of an end labeled nucleic acid fragment are resolved by size (e.g., by electrophoresis), the result is a ladder of bands indicating the site of each cleavage, measured from the labeled end. Similar analysis can be done for chemical modifications that block DNA synthesis; extension of a primer on molecules that have been partially modified will yield a nested set of termination products. Determining the sites of cleavage/modification may be done with some degree of accuracy by comparing the products to size markers (e.g., commercially available fragments of DNA for size comparison) but a more accurate measure is to create a DNA sequencing ladder for the same segment of nucleic acid to resolve alongside the test sample. This allows rapid identification of the precise site of cleavage or modification.

The oligonucleotides may interact with the target in any number of ways. For example, in another embodiment, the oligonucleotides may contact more than one region of the target nucleic acid. When the target nucleic acid is folded as described, two or more of the regions that remain single stranded may be sufficiently proximal to allow contact with a single oligonucleotide. The capture oligonucleotide in such a configuration is referred to herein as a "bridge" or "bridging" oligonucleotide, to reflect the fact that it may interact with distal regions within the target nucleic acid. The use of the terms "bridge" and "bridging" is not intended to limit these distal interactions to any particular type of interaction. It is contemplated that these interactions may include non-standard nucleic acid interactions known in the art, such as G-T base pairs, Hoogsteen interactions, triplex structures, quadraplex aggregates, and the multibase hydrogen bonding such as is observed within nucleic acid tertiary structures, such as those found in tRNAs. The terms are also not intended to indicate any particular spatial orientation of the regions of interaction on the target strand, i.e., it is not intended that the order of the contact regions in a bridge oligonucleotide be required to be in the same sequential order as the corresponding contact regions in the target strand. The order may be inverted or otherwise shuffled.

As used herein, the term "target nucleic acid" or "nucleic acid target" refers to a particular nucleic acid sequence of interest. Thus, the "target" can exist in the presence of other nucleic acid molecules or within a larger nucleic acid molecule.

The term "nucleic acid," "oligomer," or "oligonucleotide" refers to a nucleic acid with or without an LNA unit.

The following non-limiting examples are illustrative of the invention. All documents mentioned herein are incorporated herein by reference in their entirety.

General Comments

In the following Examples, compound reference numbers designate the compound as shown in Scheme 1 and 2 above.

Reactions were conducted under an atmosphere of nitrogen when anhydrous solvents were used. All reactions were monitored by thin-layer chromatography (TLC) using EM reagent plates with florescence indicator ($SiO_2$-60, F-254). The compounds were visualized under UV light and by spraying with a mixture of 5% aqueous sulfuric acid and ethanol followed by heating. Silica gel 60 (particle size 0.040–0.063 mm, Merck) was used for flash column chromatography. NMR spectra were recorded at 300 MHz for $^1$H NMR, 75.5 MHz for $^{13}$C NMR and 121.5 MHz for $^{31}$P NMR on a Varian Unity 300 spectrometer. δ-Values are in ppm relative to tetramethyl silane as internal standard ($^1$H and $^{13}$C NMR) and relative to 85% $H_3PO_4$ as external standard ($^{31}$P NMR). Coupling constants are given in Hertz. The assignments, when given, are tentative, and the assignments of methylene protons, when given, may be interchanged. Bicyclic compounds are named according to the Von Bayer nomenclature. Fast atom bombardment mass spectra (FAB-MS) were recorded in positive ion mode on a Kratos MS50TC spectrometer. The composition of the oligonucleotides were verified by MALDI-MS on a Micromass Tof Spec E mass spectrometer using a matrix of diammonium citrate and 2,6-dihydroxyacetophenone.

EXAMPLE 1

Synthesis of 1,2-O-Isopropylidene-5-O-methanesulfonyl-4-C-methanesulfonyloxymethyl-3-O-(p-methoxybenzyl)-α-D-ribofuranose [Compound 2 in Scheme 1 Above]

Mesyl chloride (8.6 g, 7.5 mmol) was dropwise added to a stirred solution of 4-C-hydroxymethyl-1,2-O-isopropylidene-3-O-p-methoxybenzyl-α-D-ribofuranose [R. Yamaguchi, T. Imanishi, S. Kohgo, H. Horie and H. Ohrui, Biosci. Biotechnol. Biochem., 1999, 63, 736] (1, 10.0 g, 29.4 mmol) in anhydrous pyridine (30 cm$^3$) and the reaction mixture was stirred overnight at room temperature. The mixture was evaporated to dryness under reduced pressure to give a residue which was co-evaporated with toluene (2×25 cm$^3$), dissolved in $CH_2Cl_2$ (200 cm$^3$) and washed successively with saturated aqueous $NaHCO_3$ (2×100 cm$^3$) and brine (50 cm$^3$). The organic phase was dried ($Na_2SO_4$), filtered and evaporated to dryness under reduced pressure. The colorless viscous oil obtained was purified by column chromatography [0.5–1% (v/v) MeOH in $CH_2Cl_2$ as eluent], followed by crystallization from MeOH to give furanose 2 as a white solid material (13.6 g, 93%); $R_f$ 0.57 ($CH_2Cl_2$/MeOH 95:5, v/v); $\delta_H$ ($CDCl_3$) 7.30 (2 H, d, J 8.7), 6.90 (2 H, d, J 8.5), 5.78 (1 H, d, J 3.7), 4.86 (1 H, d, J 12.0), 4.70 (1 H, d, J 11.4), 4.62 (1 H, dd, J 5.0 and 3.8), 4.50 (1 H, d, J 11.1), 4.39 (1 H, d, J 12.3), 4.31 (1 H, d, J 11.0), 4.17 (1 H, d, J 5.1), 4.11 (1 H, d, J 11.0), 3.81 (3 H, s), 3.07 (3 H, s), 2.99 (3 H, s), 1.68 (3 H, s), 1.34 (3 H, s); $\delta_C$ ($CDCl_3$) 159.8, 129.9, 128.8, 114.1, 114.0, 104.5, 83.2, 78.0, 77.9, 72.6, 69.6, 68.8, 55.4, 38.1, 37.5, 26.3, 25.7.

EXAMPLE 2

Synthesis of Methyl 5-O-methanesulfonyl-4-C-methanesulfonyloxymethyl-3-O-(p-methoxybenzyl)-D-ribofuranoside [Compound 3 in Scheme 1 Above]

A suspension of furanoside 2 (13.5 g, 27.2 mmol) in a mixture of $H_2O$ (45 cm$^3$) and 15% HCl in MeOH (450 cm$^3$, w/w) was stirred at room temperature for 72 h. The mixture was carefully neutralized by addition of saturated aqueous $NaHCO_3$ (100 cm$^3$) followed by $NaHCO_3$ (s) whereupon the mixture was evaporated to dryness under reduced pressure. $H_2O$ (100 cm$^3$) was added, and extraction was performed with EtOAc (3×100 cm$^3$). The combined organic phase was washed with brine (100 cm$^3$), dried ($Na_2SO_4$), filtered and then evaporated to dryness under reduced pressure. The residue was coevaporated with toluene (2×25 cm$^3$) and purified by column chromatography [1–2% (v/v) MeOH in $CH_2Cl_2$] to give furanoside 3 as an anomeric mixture (clear oil, 11.0 g, 86%, ratio between anomers ca. 6:1); $R_f$ 0.39, 0.33 ($CH_2Cl_2$/MeOH 95:5, v/v); $\delta_H$ ($CDCl_3$, major anomer only) 7.28 (2 H, d, J 8.4), 6.91 (2 H, d, J 8.9), 4.87 (1 H, s), 4.62 (1 H, d, J 11.4), 4.53 (1 H, d, J 11.2), 4.41 (2 H, s), 4.31 (1 H, d, J 9.8), 4.24 (1 H, d, J 4.6), 4.06 (1 H, d, J 10.0), 3.98 (1 H, br s), 3.81 (3 H, s), 3.33 (3 H, s), 3.06 (3 H, s), 3.03 (3 H, s); $\delta_C$ ($CDCl_3$, major anomer only) 160.0, 130.1, 128.5, 114.3, 107.8, 81.7, 81.2, 73.8, 73.6, 69.7, 69.6, 55.5, 55.4, 37.5, 37.4.

EXAMPLE 3

Synthesis of (1R,3RS,4R,7S)-1-Methanesulfonyloxymethyl-3-methoxy-7-(p-methoxybenzyloxy)-2, 5-dioxabicyclo[2.2.1]heptane [Compound 4 in Scheme 1 Above]

To a stirred solution of the anomeric mixture of Compound 3 (10.9 g, 23.2 mmol) in anhydrous DMF (50 cm$^3$) at 0° C. was added during 10 min added sodium hydride (2.28 g of a 60% suspension in mineral oil (w/w), 95.2 mmol) and the mixture was stirred for 12 h at room temperature. Ice-cold $H_2O$ (200 cm$^3$) was slowly added and extraction was performed using EtOAc (3×200 cm$^3$). The combined organic phase was washed successively with saturated aqueous $NaHCO_3$ (2×100 cm$^3$) and brine (50 cm$^3$), dried ($Na_2SO_4$), filtered and evaporated to dryness under reduced pressure. The residue was purified by column chromatography [0.5–1% (v/v) MeOH in $CH_2Cl_2$] to give first the major isomer (6.42 g, 74%) and then [1.5% (v/v) MeOH in $CH_2Cl_2$] the minor isomer (1.13 g, 13%), both as clear oils; $R_f$ 0.56, 0.45 ($CH_2Cl_2$/MeOH 95:5, v/v); $\delta_H$ ($CDCl_3$, major isomer) 7.16 (2 H, d, J 8.8), 6.74 (2 H, d, J 8.4), 4.65 (1 H, s), 4.42–4.32 (4 H, m), 3.95–3.94 (2 H, m), 3.84 (1 H, d, J 7.4), 3.66 (3 H, s), 3.54 (1 H, d, J 7.4), 3.21 (3 H, s), 2.90 (3 H, s); $\delta_C$ ($CDCl_3$, major isomer) 159.6, 129.5, 129.3, 114.0, 105.3, 83.2, 78.6, 77.2, 72.1, 71.8, 66.3, 55.6, 55.4, 37.8; $\delta_H$ ($CDCl_3$, minor isomer) 7.27 (2 H, d, J 8.9), 6.89 (2 H, d, J 8.6), 4.99 (1 H, s), 4.63–4.39 (4 H, m), 4.19 (1 H, s), 4.10–3.94 (2 H, m), 3.91 (1 H, s), 3.81 (3 H, s), 3.47 (3 H, s), 3.05 (3 H, s); $\delta_C$ ($CDCl_3$, minor isomer) 159.7, 129.6, 129.5, 114.1, 104.4, 86.4, 79.3, 77.1, 72.3, 71.9, 66.2, 56.4, 55.4, 37.7.

EXAMPLE 4

Synthesis of (1R,4R,7S)-1-Acetoxymethyl-3-methoxy-7-(p-methoxybenzyloxy)-2,5-dioxabicyclo[2.2.1]heptane [Compound 5 in Scheme 1]

To a stirred solution of furanoside 4 (major isomer, 6.36 g, 17.0 mmol) in dioxane (25 cm$^3$) was added 18-crown-6 (9.0 g, 34.1 mmol) and KOAc (8.4 g, 85.6 mmol). The stirred mixture was heated under refluxed for 12 h and subsequently evaporated to dryness under reduced pressure. The residue was dissolved in $CH_2Cl_2$ (100 cm$^3$) and washing was performed, successively, with saturated aqueous $NaHCO_3$ (2×50 cm$^3$) and brine (50 cm$^3$). The separated organic phase was dried ($Na_2SO_4$), filtered and evaporated to dryness under reduced pressure. The residue was purified by column chromatography [1% (v/v) MeOH in $CH_2Cl_2$] to give furanoside 5 as a white solid material (one anomer, 5.23 g, 91%); $R_f$ 0.63 ($CH_2Cl_2$/MeOH 95:5, v/v); $\delta_H$ ($CDCl_3$) 7.27–7.24 (2 H, m), 6.90–6.87 (2 H, m), 4.79 (1 H, s), 4.61 (1 H, d, J 11.0), 4.49 (2 H, m), 4.28 (1 H, d, J 11.0), 4.04 (3 H, m), 3.80 (3 H, s), 3.68 (1 H, m), 3.36 (3 H, s), 2.06 (3 H, s); $\delta_C$ ($CDCl_3$) 170.7, 159.5, 129.5, 129.4, 113.9, 105.1, 83.3, 78.9, 77.2, 72.0, 71.9, 61.0, 55.4, 55.3, 20.8.

EXAMPLE 5

Synthesis of (1S,4R,7S)-1-Hydroxymethyl-3-methoxy-7-(p-methoxybenzyloxy)-2,5-dioxabicyclo[2.2.1]heptane [Compound 6 in Scheme 1]

A solution of furanoside 5 (one anomer, 5.16 g, 15.3 mmol) in saturated methanolic ammonia (200 cm$^3$) was stirred at room temperature for 48 h. The reaction mixture was evaporated to dryness under reduced pressure, coevaporated with toluene (2×50 cm$^3$), and the residue purified by column chromatography [2–3% (v/v) MeOH in CH$_2$Cl$_2$] to give furanoside 6 as a white solid material (one anomer, 3.98 g, 88%); R$_f$ 0.43 (CH$_2$Cl$_2$/MeOH 95:5, v/v); δ$_H$ (CDCl$_3$) 7.27 (2 H, d, J 8.6), 6.88 (2 H, d, J 8.9), 4.79 (1 H, s), 4.59 (1 H, d, J 11.3), 4.53 (1 H, d, J 11.4), 4.09 (2 H, s), 3.97 (1 H, d, J 7.5), 3.86 (2 H, br s), 3.80 (3 H, s), 3.75–3.62 (2 H, m), 3.37 (3 H, s); δ$_c$ (CDCl$_3$) 159.4, 129.7, 129.3, 113.9, 105.2, 85.6, 78.3, 77.4, 71.9, 71.8, 58.8, 55.5, 55.3.

EXAMPLE 6

(1S,4R,7S)-3-Methoxy-7-(p-methoxybenzyloxy)-1-(p-methoxybenzyloxymethyl)-2,5-dioxabicyclo[2.2.1]heptane [Compound 7 in Scheme 1]

To a stirred solution of furanoside 6 (one anomer, 3.94 g, 13.3 mmol) in anhydrous DMF (50 cm$^3$) at 0° C. was added a suspension of NaH [60% in mineral oil (w/w), 1.46 g, 60.8 mmol] followed by dropwise addition of p-methoxybenzyl chloride (2.74 g, 17.5 mmol). The mixture was allowed to warm to room temperature and stirring was continued for another 4 h whereupon ice-cold H$_2$O (50 cm$^3$) was dropwise added. The mixture was extracted with CH$_2$Cl$_2$ (3×100 cm$^3$) and the combined organic phase was washed with brine (100 cm$^3$), dried (Na$_2$SO$_4$), filtered, evaporated to dryness under reduced pressure and coevaporated with toluene (3×50 cm$^3$). The residue (4.71 g) tentatively assigned as a mixture of 7 and aldehyde 11 was used in the preparation of 11 (see below) without further purification.

EXAMPLE 7

4-C-Methanesulfonyloxymethyl-3,5-di-O-(p-methoxybenzyl)-1,2-O-isopropylidene-α-D-ribofuranose [Compound 9 in Scheme 1]

4-C-Hydroxymethyl-3,5-di-O-(p-methoxybenzyl)-1,2-O-isopropylidene-α-D-ribofuranose [R. Yamaguchi, T. Imanishi, S. Kohgo, H. Horie and H. Ohrui, *Biosci. Biotechnol. Biochem.*, 1999, 63, 736] (8, 3.2 g, 6.95 mmol) was mesylated using MsCl (2.00 g, 17.5 mmol) and pyridine (10 cm$^3$) following the procedure described for 2. After work-up, the colorless viscous oil was purified by column chromatography [1% (v/v) MeOH in CH$_2$Cl$_2$] to give derivative 9 in 89% yield (3.17 g) as a clear oil; R$_f$ 0.45 (CH$_2$Cl$_2$/MeOH 98:2, v/v); δ$_H$ (CDCl$_3$) 7.22 (2 H, d, J 8.9), 7.18 (2 H, d, J 8.7), 6.86 (4 H, d, J 8.3), 5.76 (1 H, d, J 3.8), 4.83 (1 H, d, J 12.0), 4.64 (1 H, d, J 11.6), 4.59 (1 H, m), 4.49–4.35 (4 H, m), 4.24 (1 H, d, J 5.3), 3.80 (6 H, s), 3.56 (1 H, d, J 10.5), 3.45 (1 H, d, J 10.5), 3.06 (3 H, s), 1.67 (3 H, s), 1.33 (3 H, s); δ$_c$ (CDCl$_3$) 159.6, 159.4, 129.9, 129.8, 129.7, 129.5, 129.4, 129.3, 114.0, 113.8, 113.7, 113.6, 104.5, 84.9, 78.6, 78.1, 73.4, 72.4, 71.0, 69.9, 55.3, 38.0, 26.4, 25.9.

EXAMPLE 8

Methyl 4-C-methanesulfonyloxymethyl-3,5-di-O-(p-methoxybenzyl)-D-ribofuranose [Compound 10 in Scheme 1]

Methanolysis of furanoside 9 (3.1 g, 5.76 mmol) was performed using a mixture of a solution of 15% HCl in MeOH (w/w, 120 cm$^3$) and H$_2$O (12 cm$^3$) following the procedure described for the synthesis of 3. After work-up, the crude product was purified by column chromatography [0.5–1% (v/v) MeOH in CH$_2$Cl$_2$] to give the major anomer of 10 (1.71 g, 58%) and [1–1.5% (v/v) MeOH in CH$_2$Cl$_2$] the minor anomer of 10 (0.47 g, 16%), both as clear oils; R$_f$ 0.31, 0.24 (CH$_2$Cl$_2$/MeOH 98:2, v/v); δ$_c$ (major anomer, CDCl$_3$) 159.8, 159.5, 129.9, 129.8, 129.6, 129.5, 129.0, 114.2, 114.1, 114.0, 113.9, 107.9, 84.7, 79.9, 74.2, 73.5, 73.5, 70.2, 64.4, 55.6, 55.4, 37.4.

EXAMPLE 9

Alternative Preparation of Compound 7 in Scheme 1

Ring closure of furanoside 10 (major anomer, 1.68 g, 3.28 mmol) was achieved using NaH (60% suspension in mineral oil (w/w), 0.32 g, 13.1 mmol) in anhydrous DMF (10 cm$^3$) following the procedure described for the synthesis of 4 to give a crude product tentatively assigned as a mixture of furanoside 7 and aldehyde 11 (see below) (1.13 g).

EXAMPLE 10

(2R,3S,4S)-4-Hydroxy-3-(p-methoxybenzyloxy)-4-(p-methoxybenzyloxymethyl)-tetrahydrofuran-2-carbaldehyde [Compound 11 in Scheme 1]

A solution of crude furanoside 7 (as a mixture with 11 as prepared as described above, 5.80 g) in 80% glacial acetic acid (100 cm$^3$) was stirred at 50° C. for 4 h. The solvent was distilled off under reduced pressure and the residue was successively coevaporated with absolute ethanol (3×25 cm$^3$) and toluene (2×25 cm$^3$) and purified by column chromatography [4–5% (v/v) MeOH in CH$_2$Cl$_2$] to give aldehyde 11 as a colorless oil (4.60 g); R$_f$ 0.37 (CH$_2$Cl$_2$MeOH 95:5, v/v); δ$_H$ (CDCl$_3$) 9.64 (1 H, br s), 7.27–7.17 (4 H, m), 6.87–6.84 (4 H, m), 4.59 (1 H, d, J 11.6), 4.51–4.41 (2 H, m), 4.35 (1 H, s), 3.92–3.90 (2 H, m), 3.79 (6 H, s), 3.77–3.68 (3 H, m), 3.55 (2 H, br s); δ$_c$ (CDCl$_3$) 203.6, 159.5, 159.4, 129.7, 129.6, 129.5, 129.2, 114.0, 113.9, 113.8, 87.3, 86.7, 81.0, 75.1, 73.4, 71.6, 67.6, 55.3.

EXAMPLE 11

General Procedure for the Reaction of Aryl Magnesium Bromides with Aldehyde 11 to Give Compounds 12a–e in Scheme 2

A solution of aldehyde 11 (Scheme 2) in anhydrous THF (10 cm$^3$) was added dropwise during 5 min to a stirred solution of the aryl magnesium bromide dissolved in anhydrous THF at 0° C. The mixture was allowed to heat to room temperature and stirred for 12 h. The mixture was evaporated to dryness under reduced pressure and the residue diluted with CH$_2$Cl$_2$ and washed several times with saturated aqueous NH$_4$Cl. The organic phase was dried (Na$_2$SO$_4$), filtered, and evaporated to dryness under reduced pressure. Column chromatography of the crude product obtained afforded the compounds 12a–e as shown in Scheme 2.

EXAMPLE 11a

Synthesis of (2S,3S,4S)-4-Hydroxy-2-[(R)-hydroxy (Phenyl)methyl]-4-(p-methoxybenzyloxy)-3-(p-methoxybenzyloxymethyl) tetrahydrofuran [Compound 12a of Scheme 2]

Grignard reaction of phenylmagnesium bromide (1.0 M solution in THF, 14.2 cm$^3$, 14.2 mmol) with aldehyde 11 (515 mg, 1.28 mmol) afforded 12a as shown in Scheme 2. The crude product was purified by column chromatography [4% (v/v) MeOH in CH$_2$Cl$_2$] to give tetrahydrofuran 12a (540 mg, 88%) as a colorless oil; R$_f$ 0.34 (CH$_2$Cl$_2$/MeOH 95:5, v/v); $\delta_H$ (CDCl$_3$) 7.40–7.19 (7 H, m), 6.91–6.73 (6 H, m), 4.73 (1 H, d, J 6.4), 4.48 (2 H, s), 4.08 (2 H, s), 3.88 (1 H, d, J 9.4), 3.79 (1 H, m), 3.78 (3 H, s), 3.76 (3 H, s), 3.75–3.69 (2 H, m), 3.50 (1 H, d, J 9.4), 3.45 (1 H, s), 3.42 (1 H, br s), 3.26 (1 H, br s); $\delta_c$ (CDCl$_3$) 159.5, 159.3, 140.7, 129.7, 129.6, 129.5, 129.2, 128.5, 128.0, 127.3, 113.9, 113.8, 113.7, 89.4, 84.6, 81.8, 75.3, 74.7, 73.5, 71.6, 69.3, 55.3; m/z (FAB) 503 [M+Na]$^+$, 479 [M–H]$^+$, 461 [M–H–H$_2$O]$^+$.

EXAMPLE 11b

Synthesis of (2S,3S,4S)-4-Hydroxy-2-[(R)-hydroxy (4-fluoro-3-methylphenyl)methyl]-4-(p-methoxybenzyloxy)-3-(p-methoxybenzyloxymethyl)tetrahydrofuran [Compound 12b of Scheme 2]

Grignard reaction of 4-fluoro-3-methylphenylmagnesium bromide (1.0 M solution in THF, 15.0 cm$^3$, 15.0 mmol) with aldehyde 11 (603 mg, 1.5 mmol) afforded 12b as shown in Scheme 2. The crude product was purified by column chromatography [4–5% (v/v) MeOH in CH$_2$Cl$_2$] to give tetrahydrofuran 12b (611 mg, 85%) as a colorless oil; R$_f$ 0.34 (CH$_2$Cl$_2$/MeOH 95:5, v/v); $\delta_H$ (CDCl$_3$) 7.24–7.12 (5 H, m), 6.98–6.84 (5 H, m), 6.77 (1 H, d, J 8.5), 4.65 (1 H, dd, J 2.8 and 6.4), 4.49 (2 H, s), 4.15 (2 H, s), 4.01 (1 H, dd, J 2.3 and 6.5), 3.87 (1 H, d, J 9.3), 3.79 (3H, s), 3.78 (3 H, s), 3.76–3.68 (2 H, m), 3.52 (1 H, s), 3.47 (1 H, d, J 10.3), 3.42 (1 H, d, J 2.9), 3.22 (1 H, s), 2.24 (3 H, d, J 0.8); $\delta_c$ (CDCl$_3$) 162.7, 159.5, 159.4, 136.2, 136.1, 130.3, 130.2, 129.7, 129.6, 129.5, 129.4, 129.1, 126.1, 126.0, 115.1, 114.8, 114.0, 113.9, 113.8, 89.3, 84.5, 81.8, 75.3, 74.0, 73.5, 71.7, 69.2, 55.4, 55.3, 14.7 (d, J 3.9); m/z (FAB) 535 [M+Na]$^+$, 511 [M–H]$^+$, 493 [M–H—H$_2$O]$^+$.

EXAMPLE 11c

Synthesis of (2S,3S,4S)-4-Hydroxy-2-[(R)-hydroxy (1-naphtyl)methyl]-4-(p-methoxybenzyloxy)-3-(p-methoxybenzyloxymethyl) tetrahydrofuran [Compound 12c of Scheme 2]

1-Bromonaphthalene (1.55 g, 7.5 mmol) was added to a stirred mixture of magnesium turnings (182 mg, 7.5 mmol) and iodine (10 mg) in THF (10 cm$^3$). The mixture was stirred at 40° C. for 1 h whereupon it was allowed to cool to room temperature. A solution of aldehyde 11 (603 mg, 1.5 mmol) in THF (10 cm$^3$) was added slowly and the reaction was stirred for 12 h. The crude product was purified by column chromatography [4–5% (v/v) MeOH in CH$_2$Cl$_2$] to give tetrahydrofuran 12c (756 mg, 95%) as a colorless oil; R$_f$ 0.35 (CH$_2$Cl$_2$/MeOH 95:5, v/v); $\delta_H$ (CDCl$_3$) 8.08 (1 H, m), 7.86 (1 H, m), 7.79 (1 H, d, J 8.2), 7.72 (1 H, d, J 7.2), 7.49–7.44 (3H, m), 7.18 (2 H, d, J 8.4), 6.84 (2 H, d, J 8.6), 6.74 (2 H, d, J 8.7), 6.68 (2 H, d, J 8.8), 5.52 (1 H, dd, J 3.7 and 5.6), 4.45 (2 H, s), 4.34 (1 H, dd, J 2.5 and 5.9), 4.03 (1 H, d , J 11.0), 3.96 (1 H, d, J 11.0), 3.93 (1 H, d, J 9.5), 3.80 (1 H, d, J 9.3), 3.77 (3 H, s), 3.75 (1 H, d, J 2.6), 3.72 (3 H, s), 3.68 (1 H, d, J 9.3), 3.56 (1 H, d, J 3.7), 3.49 (1 H, d, J 9.3), 3.34 (1 H, s); $\delta_c$ (CDCl$_3$) 159.5, 159.3, 136.3, 134.0, 131.0, 129.7, 129.6, 129.5, 129.4, 129.0, 128.6, 128.2, 125.6, 125.5, 123.5, 114.0, 113.8, 113.7, 88.7, 84.7, 81.9, 75.5, 73.5, 71.7, 71.3, 69.3, 55.4, 55.3; m/z (FAB) 553 [M+Na]$^+$, 529 [M–H]$^+$, 511 [M–H–H$_2$O]$^+$.

EXAMPLE 11d (2S,3S,4S)-4-Hydroxy-2-[(R)-hydroxy(1-pyrenyl) methyl]-4-(p-methoxybenzyloxy)-3-(p-methoxybenzyloxymethyl)tetrahydrofuran [Compound 12d of Scheme 2]

Tetrahydrofuran 12d was synthesized from aldehyde 11 (515 mg, 1.28 mmol), 1-bromopyrene (1.0 g, 3.56 mmol), magnesium turnings (155 mg, 6.4 mmol), iodine (10 mg) and THF (20 cm$^3$) following the procedure described for synthesis of compound 12c. The crude product was purified by column chromatography [3–4% (v/v) MeOH in CH$_2$Cl$_2$] to give tetrahydrofuran 12d (690 mg, 89%) as a pale yellow solid; R$_f$ 0.35 (CH$_2$Cl$_2$/MeOH 95:5, v/v); $\delta_H$ (CDCl$_3$) 8.23 (2 H, d, J 8.4 and 9.2), 8.19–8.13 (3 H, m), 8.05–7.99 (4 H, m), 7.14 (2 H, d, J 8.8), 6.82 (2 H, d, J 9.0), 6.30 (2 H, d, J 8.7), 6.20 (2 H, d, J 8.6), 5.87 (1 H, d, J 7.2), 4.43 (2 H, s), 4.41 (1 H, m), 4.01 (1 H, d, J 9.4), 3.91 (1 H, d, J 11.8), 3.86 (1 H, d, J 9.2), 3.77 (1 H, d, J 1.9), 3.76 (3 H, s), 3.70–3.64 (3 H, m), 3.52–3.45 (1 H, m), 3.44 (3 H, s); $\delta_c$ (CDCl$_3$) 159.5, 158.9, 133.9, 131.4, 131.1, 130.7, 129.7, 129.5, 129.2, 128.9, 128.5, 127.8, 127.7, 127.5, 126.0, 125.5, 125.3, 125.2, 125.1, 125.0, 124.9, 122.9, 113.9, 113.3, 89.5, 83.5, 82.0, 75.7, 73.4, 71.3, 71.0, 69.3, 55.3, 55.0; m/z (MALDI) 627 [M+Na]$^+$, 609 [M$^+$+Na–H$_2$O]$^+$.

EXAMPLE 11e (2S,3S,4S)-4-Hydroxy-2-[(R)-hydroxy(2,4,5-trimethylphenyl)methyl]-4-(p-methoxybenzyloxy)-3-(p-methoxybenzyloxymethyl) tetrahydrofuran [Compound 12e of Scheme 2]

Tetrahydrofuran 12e was synthesized from aldehyde 11 (515 mg, 1.28 mmol), 1-bromo-2,4,5-trimethylbenzene (1.28 g, 6.4 mmol), magnesium turnings (155 mg, 6.4 mmol), iodine (10 mg) and THF (20 cm$^3$) following the procedure described for synthesis of compound 12c. The crude product was purified by column chromatography [3–4% (v/v) MeOH in CH$_2$Cl$_2$] to give tetrahydrofuran 12e (589 mg, 88%) as a colorless oil; R$_f$ 0.34 (CH$_2$Cl$_2$/MeOH 95:5, v/v); $\delta_H$ (CDCl$_3$) 7.25 (2 H, d, J 8.7), 7.21 (2 H, d, J 8.9), 6.90 (1 H, s), 6.87 (1 H, s), 6.85 (2 H, d, J 8.9), 6.76 (2 H, d, J 8.7), 4.95 (1 H, dd, J 3.6 and 5.9), 4.48 (2 H, s), 4.18–4.08 (3 H, m), 3.89 (1 H, d, J 9.6), 3.80 (1 H, m), 3.79 (3 H, s), 3.77 (3 H, s), 3.71 (1 H, d, J 9.2), 3.64 (1 H, d, J 2.6), 3.51 (1 H, d, J 9.4), 3.24 (1 H, s), 3.18 (1 H, d, J 3.4), 2.25 (3 H,s), 2.22 (3 H,s), 2.21 (3 H, s); $\delta_c$ (CDCl$_3$) 159.5, 159.3, 136.0, 135.8, 134.2, 132.5, 132.0, 129.8, 129.7, 129.6, 129.5, 128.5, 113.9, 113.8, 88.6, 84.7, 81.7, 75.4, 73.6, 71.7, 70.9, 69.4, 55.3, 19.5, 19.4, 19.0; m/z (FAB) 545 [M+Na]$^+$, 521 [M–H]$^+$, 503 [M–H–H$_2$O ]$^+$.

EXAMPLE 12

General Procedure for the Cyclization of 12a–e to give Compounds 13a–e as Shown in Scheme 2

N,N',N'-Tetramethylazodicarboxamide (TMAD) was added in one portion to a stirred solution of the compounds 12a–e as shown in Scheme 2 and tributylphosphine in benzene at 0° C. The mixture was stirred for 12 h at room temperature whereupon it was diluted with diethyl ether (50 cm$^3$). The organic phase was washed successively with saturated aqueous NH$_4$Cl (2×20 cm$^3$) and brine (25 cm$^3$), dried (Na$_2$SO$_4$), filtered and evaporated to dryness under reduced pressure. The crude product obtained was purified by column chromatography [1.5–2% (v/v) MeOH in CH$_2$Cl$_2$] to give compounds 13a–e as shown in Scheme 2.

EXAMPLE 12a (1S,3S,4R,7S)-7-(p-Methoxybenzyloxy)-1-(p-methoxybenzyloxymethyl)-3-phenyl-2,5-dioxabicyclo[2.2.1]heptane [Compound 13a of Scheme 2]

Cyclization of compound 12a (540 mg, 1.13 mmol) in the presence of TMAD (310 mg, 1.8 mmol), PBu$_3$ (364 mg, 1.8 mmol) and benzene (10 cm$^3$) followed by the general work-up procedure and column chromatography afforded compound 13a as a colorless oil (400 mg, 77%); R$_f$ 0.51 (CH$_2$Cl$_2$/MeOH 98:2, v/v); δ$_H$ (CDCl$_3$) 7.36–7.33 (7 H, m), 7.10 (2 H, d, J 8.3), 6.88 (2 H, d, J 8.7), 6.78 (2 H, d, J 8.7), 5.17 (1 H, s, H-3), 4.59 (2 H, br s, —CH$_2$(MPM)), 4.43 (1 H, d, J 11.3, —CH$_2$(MPM)), 4.34 (1 H, d, J 11.3, —CH$_2$(MPM)), 4.19 (1 H, s, H-4), 4.09 (1 H, d, J 7.7, H-6), 4.06 (1 H, d, J 7.7, H-6), 4.01 (1 H, s, H-7), 3.82–3.77 (5 H, m, —C$_1$—CH$_2$—O—, OCH$_3$), 3.76 (3 H, s, —OCH$_3$); δ$_c$ (CDCl$_3$) 159.4, 159.3, 139.4 (C-1'), 130.3, 129.7, 129.5, 129.3, 128.5, 127.5, 125.4, 113.9, 113.8, 85.9 (C-1), 84.1 (C-3), 81.1 (C-4), 77.4 (C-7), 73.7 (—CH$_2$(MPM)), 73.4 (C-6), 71.8 (—CH$_2$(MPM)), 66.3 (—C$_1$—CH$_2$—O—), 55.4 (—OCH$_3$), 55.3 (—OCH$_3$); m/z (FAB) 467 [M+Na—H$_2$O]$^+$, 461 [M–H]$^+$.

EXAMPLE 12b (1S,3S,4R,7S)-3-(4-Fluoro-3-methylphenyl)-7-(p-methoxybenzyloxy)-1-(p-methoxybenzyloxymethyl)-2,5-dioxabicyclo[2.2.1]heptane [Compound 13b of Scheme 2]

Cyclization of compound 12b (550 mg, 1.08 mmol) in the presence of TMAD (275 mg, 1.6 mmol), PBu$_3$ (325 mg, 1.6 mmol) and benzene (10 cm$^3$) followed by the general work-up procedure and column chromatography afforded compound 13b as a colorless oil (445 mg, 84%); R$_f$ 0.52 (CH$_2$Cl$_2$/MeOH 98:2, v/v); δ$_H$ (CDCl$_3$) 7.28 (2 H, d, J 8.7), 7.11 (2 H, d, J 8.6), 7.08–7.09 (2 H, m, H-2' and H-6'), 6.94 (1 H, dd, J 8.5 and 9.2, H-5'), 6.88 (2 H, d, J 8.6), 6.79 (2 H, d, J 8.4), 5.08 (1 H, s, H-3), 4.62–4.55 (2 H, m, —CH$_2$(MPM)), 4.45 (1 H, d, J 11.1, —CH$_2$(MPM)), 4.36 (1 H, d, J 11.6, —CH$_2$(MPM)), 4.13 (1 H, s, H-4), 4.07, 4.03 (1 H each, 2d, J 7.6 each, H-6), 3.99 (1 H, s, H-7), 3.81 (2 H, m, —C$_1$—CH$_2$—O—), 3.80 (3 H, s, —OCH$_3$), 3.77 (3 H, s, —OCH$_3$), 2.23 (3 H, d, J 1.6, Ar—CH$_3$); δ$_c$ (CDCl$_3$) 162.3 (C-4'), 159.4, 159.3, 134.8, 134.7, 130.3, 129.6, 129.5, 129.2, 128.5, 128.4, 128.3, 124.2, 115.1, 114.8, 113.9, 113.8, 85.9 (C-1), 83.3 (C-3), 81.0 (C-4), 77.1 (C-7), 73.6 (—CH$_2$(MPM)), 73.4 (C-6), 71.8 (—CH$_2$(MPM)), 66.2 (—C$_1$—CH$_2$—O—), 55.4 (—OCH$_3$), 55.3 (—OCH$_3$), 14.7 (d, J 3.3, Ar—CH$_3$); m/z (FAB) 494 [M]$^+$, 493 [M–H]$^+$.

EXAMPLE 12c (1S,3S,4R,7S)-7-(p-Methoxybenzyloxy)-1-(p-methoxybenzyloxymethyl)-3-(1-naphthyl)-2,5-dioxabicyclo[2.2.1]heptane [Compound 13c of Scheme 2]

Cyclization of compound 12c (700 mg, 1.32 mmol) in the presence of TMAD (345 mg, 2.0 mmol), PBu$_3$ (405 mg, 2.0 mmol) and benzene (15 cm$^3$) followed by the general work-up procedure and column chromatography afforded compound 13c as a colorless oil (526 mg, 78%); R$_f$ 0.53 (CH$_2$Cl$_2$/MeOH 98:2, v/v); δ$_H$ (CDCl$_3$) 7.91–7.86 (2 H, m), 7.78 (1 H, d, J 8.2), 7.73 (1 H, d, J 7.1), 7.53–7.46 (3 H, m), 7.32 (2 H, d, J 8.7), 7.04 (2 H, d , J 8.7), 6.90 (2 H, d, J 8.3), 6.71 (2 H, d, J 8.6), 5.79 (1 H, s, H-3), 4.67–4.61 (2 H, m, —CH$_2$(MPM)), 4.43 (1 H, s, H-4), 4.38 (1 H, d, J 11.2, —CH$_2$(MPM)), 4.27 (1 H, d, J 10.9, —CH$_2$(MPM)), 4.16 (2 H, br s, H-6), 4.08 (1 H, s, H-7), 3.91, 3.87 (1 H each, 2d, J 11.0 each, —C$_1$—CH$_2$—O—), 3.81 (3 H, s, —OCH$_3$), 3.72 (3 H, s, —OCH$_3$); δ$_c$ (CDCl$_3$) 159.3, 134.6 (C-1'), 133.5, 130.3, 129.8, 129.7, 129.4, 129.3, 128.9, 128.1, 126.4, 125.8, 125.6, 123.8, 122.7, 113.9, 113.7, 85.7 (C-1), 82.3 (C-3), 79.9 (C-4), 78.2 (C-7), 73.7 (—OCH$_2$(MPM)), 73.5 (C-6), 71.8 (—OCH$_2$(MPM)), 66.3 (—C$_1$—CH$_2$—O—), 55.4 (—OCH$_3$), 55.3 (—OCH$_3$); m/z (FAB) 512 [M]$^+$, 511 [M–H]$^+$.

EXAMPLE 12d (1S,3S,4R,7S)-7-(p-Methoxybenzyloxy)-1-(p-methoxybenzyloxymethyl)-3-(1-pyrenyl)-2,5-dioxabicyclo[2.2.1]heptane [Compound 13d of Scheme 2]

Cyclization of compound 12d (650 mg, 1.08 mmol) in the presence of TMAD (275 mg, 1.6 mmol), PBu$_3$ (325 mg, 1.6 mmol) and benzene (10 cm$^3$) followed by the general work-up procedure and column chromatography afforded compound 13d as a pale yellow solid (496 mg, 79%); R$_f$ 0.53 (CH$_2$Cl$_2$MeOH 98:2, v/v); δ$_H$ (CDCl$_3$) 8.29 (1 H, d, J 8.2), 8.18–8.12 (5 H, m), 8.08–8.01 (2 H, m), 7.96 (1 H, d, J 7.5), 7.35 (2 H, d, J 8.5), 6.97 (2 H, d, J 8.9), 6.92 (2 H, d, J 8.8), 6.60 (2 H, d, J 8.8), 6.09 (1 H, s, H-3), 4.71–4.65 (2 H, m, —CH$_2$(MPM)), 4.49 (1 H, s, H-4), 4.34 (1 H, d, J 11.4, —CH$_2$(MPM)), 4.23 (1 H, d, J 11.1, —CH$_2$(MPM)), 4.25 (1 H, d, J 7.6, H-6), 4.21 (1 H, d, J 7.8, H-6), 4.16 (1 H, s, H-7), 3.95–3.94 (2 H, m, —C$_1$—CH$_2$—O—), 3.81 (3 H, s, —OCH$_3$), 3.59 (3 H, s, —OCH$_3$); δ$_c$ (CDCl$_3$) 159.4, 159.3, 132.2 (C-1'), 131.4, 130.8, 130.7, 130.4, 129.5, 129.4, 128.0, 127.5, 127.4, 126.9, 126.1, 125.6, 125.4, 124.9, 124.8, 124.7, 123.6, 122.0, 113.9, 113.7, 85.9 (C-1), 82.7 (C-3), 80.6 (C-4), 77.9 (C-7), 73.9 (—OCH$_2$(MPM)), 73.5 (C-6), 71.8 (—OCH$_2$(MPM)), 66.3 (—C$_1$—CH$_2$—O—), 55.4 (—OCH$_3$), 55.2 (—OCH$_3$); m/z (FAB) 587[M+H]$^+$, 586 [M]$^+$.

EXAMPLE 12e (1S,3S,4R,7S)-7-(p-Methoxybenzyloxy)-1-(p-methoxybenzyloxymethyl)-3-(2,4,5-trimethylphenyl)-2,5-dioxa bicyclo[2.2.1]heptane [Compound 13e of Scheme 2]

Cyclization of compound 12e (550 mg, 1.05 mmol) in the presence of TMAD (275 mg, 1.6 mmol), PBu$_3$ (325 mg, 1.6 mmol) and benzene (10 cm³) followed by the general work-up procedure and column chromatography afforded compound 13e as a colorless oil (425 mg, 80%); $R_f$ 0.52 (CH$_2$Cl$_2$/MeOH 98:2, v/v); $\delta_H$ (CDCl$_3$) 7.30 (2 H, d, J 9.0), 7.24 (1 H, s, H-6'), 7.13 (2 H, d, J 8.9), 6.89 (1 H, s, H-3'), 6.88 (2 H, d, J 8.8), 6.79 (2 H, d, J 8.6), 5.18 (1 H, s, H-3), 4.64–4.57 (2 H, m, —CH$_2$(MPM)), 4.46 (1 H, d, J 11.2, —CH$_2$(MPM)), 4.36 (1 H, d, J 11.5, —CH$_2$(MPM)), 4.18 (1 H, s, H-4), 4.14 (1 H, s, H-7), 4.09 (1 H, d, J 7.9, H-6), 4.04 (1 H, d, J 7.7, H-6), 3.86 (2 H, s, —C$_1$—CH$_2$—O—), 3.80 (3 H, s, —OCH$_3$), 3.76 (3H, s, —OCH$_3$), 2.21 (6 H, s, 2×Ar—CH$_3$), 2.17 (3 H, s, Ar—CH$_3$); $\delta_c$ (CDCl$_3$) 159.4, 159.3, 135.5 (C-1'), 134.4, 134.0, 131.7, 131.3, 130.5, 129.9, 129.4, 129.2, 127.2, 113.9, 113.8, 85.6 (C-1), 82.4 (C-3), 79.4 (C-4), 77.6 (C-7), 73.5 (—OCH$_2$(MPM)), 73.4 (C-6), 71.8 (—OCH$_2$(MPM)), 66.3 (—C$_1$—CH$_2$—O—), 55.4 (—OCH$_3$), 55.3 (—OCH$_3$), 19.5 (—CH$_3$), 19.3 (—CH$_3$), 18.4 (—CH$_3$); m/z (FAB) 504 [M]$^+$, 503 [M−H]$^+$.

EXAMPLE 14

General Procedure for the Oxidative Removal of the p-methoxybenzyl Groups to Give Compounds 14a–e as Shown in Scheme 2

To a stirred solution of Compound 13a–e in CH$_2$Cl$_2$ (containing a small amount of H$_2$O) at room temperature, was added 2,3-dichloro-5,6-dicyanoquinone (DDQ) which resulted in an immediate appearance of a deep greenish-black color which slowly faded into pale brownish-yellow. The reaction mixture was vigorously stirred at room temperature for 4 h. The precipitate was removed by filtration through a short pad of silica gel and washed with EtOAc. The combined filtrate was washed, successively, with saturated aqueous NaHCO$_3$ (2×25 cm³) and brine (25 cm³). The separated organic phase was dried (Na$_2$SO$_4$), filtered and evaporated to dryness under reduced pressure. The crude product obtained was purified by column chromatography [4–5% (v/v) MeOH in CH$_2$Cl$_2$] to give compounds 14a–e.

EXAMPLE 14a (1S,3S,4R,7S)-7-Hydroxy-1-hydroxymethyl-3-phenyl-2,5-dioxabicyclo[2.2.1]heptane [Compound 14a of Scheme 2]

Compound 13a (400 mg, 0.86 mmol) was treated with DDQ (600 mg, 2.63 mmol) in a mixture of CH$_2$Cl$_2$ (10 cm³) and H$_2$O (0.5 cm³). After the general work-up procedure and column chromatography, compound 14a was obtained as a white solid material (128 mg, 66%); $R_f$ 0.30 (CH$_2$Cl$_2$/MeOH 9:1, v/v); $\delta_H$ ((CD$_3$)$_2$CO/CD$_3$OD; (CD$_3$)$_2$CO was added to the compound followed by addition of CD$_3$OD until a clear solution appeared) 7.40–7.22 (5 H, m), 4.99 (1 H, s), 4.09 (1 H, s), 4.04 (1 H, s), 4.01 (1 H, d, J 7.7), 3.86 (1 H, d, J 7.7), 3.90 (2 H, br s), 3.77 (2 H, br s); $\delta_c$ ((CD$_3$)$_2$CO/CD$_3$OD; (CD$_3$)$_2$CO was added to the compound followed by addition of CD$_3$OD until a clear solution appeared) 140.0, 128.2, 127.2, 125.4, 87.2, 83.7, 83.5, 72.3, 70.2, 58.4; m/z (FAB) 223[M+H]$^+$.

EXAMPLE 14b (1S,3S,4R,7S)-3-(4-Fluoro-3-methylphenyl)-7-hydroxy-1-hydroxymethyl-2,5-dioxabicyclo[2.2.1] heptane [Compound 14b of Scheme 2]

Compound 13b (400 mg, 0.81 mmol) was treated with DDQ (570 mg, 2.5 mmol) in a mixture of CH$_2$Cl$_2$ (10 cm³) and H$_2$O (0.5 cm³). After the general work-up procedure and column chromatography, compound 14b was obtained as a white solid material (137 mg, 67%); $R_f$ 0.31 (CH$_2$Cl$_2$/MeOH 9:1, v/v); $\delta_H$ (CD$_3$OD) 7.23 (1 H, d, J 8.1), 7.19 (1 H, m), 6.99 (1 H, dd, J 8.5 and 9.3), 4.99 (1 H, s), 4.09 (1 H, s), 4.06 (1 H, s), 4.03 (1 H, d, J 7.6), 3.93–3.91 (3 H, m), 2.25 (3 H, d, J 1.4); $\delta_c$ (CD$_3$OD) 161.9 (d, J 243.3), 136.4 (d, J 3.4), 129.6 (d, J 5.0), 126.1 (d, J 22.8), 125.5 (d, J 8.0), 115.7 (d, J 22.9), 88.5, 85.0, 84.3, 73.5, 71.3, 59.4, 14.5 (d, J 3.7); m/z (FAB) 255 [M+H]$^+$.

EXAMPLE 14c (1S,3S,4R,7S)-7-Hydroxy-1-hydroxymethyl-3-(1-naphthyl)-2,5-dioxabicyclo[2.2.1]heptane [Compound 14b of Scheme 2]

Compound 13c (475 mg, 0.93 mmol) was treated with DDQ (600 mg, 2.63 mmol) in a mixture of CH$_2$Cl$_2$ (10 cm³) and H$_2$O (0.5 cm³). After the general work-up procedure and column chromatography, compound 14c was obtained as a white solid material (170 mg, 67%); $R_f$ 0.31 (CH$_2$Cl$_2$/MeOH 9:1, v/v); $\delta_H$ (CDCl$_3$/CD$_3$OD; CD$_3$OD was added to the compound followed by addition of CDCl$_3$ until a clear solution appeared) 7.94–7.86 (2 H, m), 7.80–7.74 (2 H, m), 7.55–7.46 (3 H, m), 5.74 (1 H, s), 4.56 (2 H, br s), 4.37 (1 H, s), 4.24 (1 H, s), 4.17–4.11 (2 H, m), 4.04 (2 H, br s); $\delta_c$ (CDCl$_3$/CD$_3$OD; CD$_3$OD was added to the compound followed by addition of CDCl$_3$ until a clear solution appeared) 134.7, 134.0, 130.2, 129.3, 128.6, 126.8, 126.2, 125.8, 123.8, 122.8, 87.4, 83.1, 82.2, 73.1, 71.5, 59.0; m/z (FAB) 273 [M+H]$^+$, 272 [M]$^+$.

EXAMPLE 14d (1S,3S,4R,7S)-7-Hydroxy-1-hydroxymethyl-3-(1-pyrenyl)-2,5-dioxabicyclo[2.2.1]heptane [Compound 14d of Scheme 2]

Compound 13d (411 mg, 0.7 mmol) was treated with DDQ (570 mg, 2.5 mmol) in a mixture of CH$_2$Cl$_2$ (10 cm³) and H$_2$O (0.5 cm³). After the general work-up procedure and column chromatography, compound 14d was obtained as a white solid material (182 mg, 75%); $R_f$ 0.32 (CH$_2$Cl$_2$/MeOH 9:1, v/v); $\delta_H$ (CDCl$_3$/CD$_3$OD; CD$_3$OD was added to the compound followed by addition of CDCl$_3$ until a clear solution appeared) 8.32 (1 H, d, J 7.8), 8.23–8.18 (5 H, m), 8.06 (2 H, br s), 8.01 (1 H, d, J 7.6), 6.06 (1H, s), 4.47 (1 H, s), 4.36 (1 H, s), 4.27–4.18 (2 H, m), 4.10 (2 H, br s); $\delta_c$ (CDCl$_3$/CD$_3$OD) 132.2, 131.0, 128.5, 127.8, 127.3, 126.5, 125.9, 125.7, 125.1, 123.6, 122.1, 87.7, 83.7, 82.6, 73.1, 71.4, 58.9; m/z (FAB) 347 [M+H]$^+$, 346 [M]$^+$.

EXAMPLE 14e (1S,3S,4R,7S)-7-Hydroxy-1-hydroxymethyl-3-(2,4,5-trimethylphenyl)-2,5-dioxabicyclo[2.2.1]heptane [Compound 14e of Scheme 2]

Compound 13e (355 mg, 0.7 mmol) was treated with DDQ (570 mg, 2.5 mmol) in a mixture of $CH_2Cl_2$ (10 cm$^3$) and $H_2O$ (0.5 cm$^3$). After the general usual work-up procedure and column chromatography, compound 14e was obtained as a white solid material (120 mg, 65%); $R_f$ 0.31 ($CH_2Cl_2$/MeOH 9:1, v/v); $\delta_H$ (CDCl$_3$/CD$_3$OD; CD$_3$OD was added to the compound followed by addition of CDCl$_3$ until a clear solution appeared) 7.23 (1 H, s), 6.92 (1 H, s), 5.14 (1 H, s), 4.26 (1 H, s), 4.10 (1 H, s), 4.08, (1 H, d, J 7.7), 4.00–3.95 (3 H, m), 2.23 (6 H, s), 2.21 (1 H, s); $\delta_c$ (CDCl$_3$/CD$_3$OD; CD$_3$OD was added to the compound followed by addition of CDCl$_3$ until a clear solution appeared) 135.6, 133.9, 133.8, 131.7, 131.2, 126.6, 86.6, 82.1, 81.9, 72.3, 70.6, 58.5, 19.2, 19.0, 18.1; m/z (FAB) 265 [M+H]$^+$, 264 [M]$^+$.

EXAMPLE 15

General Procedure for Dimethoxytritylation of Compounds 14a–e to Give Compounds 15a–e as Shown in Scheme 2

4,4'-Dimethoxytrityl chloride (DMTCl) was added in one portion to a stirred solution of compound 14a–e in anhydrous pyridine. After stirring the mixture at room temperature for 4 h, methanol (0.2 cm$^3$) was added and the resulting mixture was evaporated to dryness under reduced pressure. The residue was coevaporated with anhydrous CH$_3$CN (2×5 cm$^3$) and anhydrous toluene (2×5 cm$^3$) and then dissolved in CH$_2$Cl$_2$ (20 cm$^3$, traces of acid removed by filtration through a short pad of basic alumina). The resulting solution was washed, successively, with saturated aqueous NaHCO$_3$ (2×10 cm$^3$) and brine (10 cm$^3$). The separated organic phase was dried (Na$_2$SO$_4$), filtered and evaporated to dryness under reduced pressure. The crude product obtained was purified by column chromatography [0.25–0.50% (v/v) MeOH in CH$_2$Cl$_2$, containing 0.5% Et$_3$N] affording compounds 15a–e.

EXAMPLE 15a (1R,3S,4R,7S)-1-(4,4'-Dimethoxytrityloxymethyl)-7-hydroxy-3-phenyl-2,5-dioxabicyclo[2.2.1]heptane [Compound 15a of Scheme 2]

Dimethoxytritylation of compound 14a (108 mg, 0.49 mmol) using DMTCl (214 mg, 0.63 mmol) in anhydrous pyridine (2 cm$^3$) followed by the general work-up procedure and column chromatography afforded compound 15a as a white solid material (180 mg, 71%); $R_f$ 0.31 (CH$_2$Cl$_2$/MeOH 98:2, v/v); $\delta_H$ (CDCl$_3$) 7.66–7.21 (14 H, m), 6.84 (4 H, d, J 8.8), 5.19 (1 H, s), 4.29 (1 H, s), 4.13 (1 H, s), 4.07 (1 H, d, J 8.4), 4.01 (1 H, d, J 8.3), 3.78 (6H, s), 3.55 (1 H, d, J 10.2), 3.50 (1 H, d, J 10.7), 2.73 (1 H, br s); $\delta_c$ (CDCl$_3$) 158.6, 149.8, 144.9, 139.4, 136.2, 135.9, 135.8, 130.3, 130.2, 128.5, 128.3, 128.0, 127.6, 126.9, 125.4, 123.9, 113.3, 86.4, 86.0, 83.8, 83.4, 73.0, 71.6, 60.2, 55.3; m/z (FAB) 525 [M+H]$^+$, 524 [M]$^+$.

EXAMPLE 15b (1R,3S,4R,7S)-1-(4,4'-Dimethoxytrityloxymethyl)-3-(4-fluoro-3-methylphenyl)-7-hydroxy-2,5-dioxabicyclo[2.2.1]heptane [Compound 15b of Scheme 2]

Dimethoxytritylation of compound 14b (95 mg, 0.38 mmol) using DMTCl (129 mg, 0.42 mmol) in anhydrous pyridine (2 cm$^3$) followed by the general work-up procedure and column chromatography afforded compound 15b as a white solid material (126 mg, 61%); $R_f$ 0.32 (CH$_2$Cl$_2$/MeOH 98:2, v/v); $\delta_H$ (CDCl$_3$) 7.53–7.15 (11 H, m), 6.97 (1 H, dd, J 8.7 and 8.9), 6.84 (4 H, d, J 8.8), 5.11 (1 H, s), 4.26 (1 H, d, J 3.9), 4.08 (1 H, s), 4.03 (1 H, d, J 8.0), 3.95 (1 H, d, J 8.0), 3.78 (6 H, s), 3.54 (1 H, d, J 10.5), 3.47 (1 H, d, J 10.1), 2.26 (3 H, d, J 1.5), 2.08 (1 H, br s); $\delta_c$ (CDCl$_3$) 160.8 (d, J 244.1), 158.7, 144.9, 135.9, 134.7, 134.6, 130.3, 130.2, 130.1, 128.5, 128.4, 128.3, 128.0, 127.0, 125.2, 124.9, 124.4, 124.3, 115.2, 114.9, 113.4, 86.5, 86.0, 83.7, 83.0, 72.9, 71.7, 60.1, 55.3, 14.8 (d, J 3.1); m/z (FAB) 556 [M]$^+$.

EXAMPLE 15c 1R,3S,4R,7S)-1-(4,4'-Dimethoxytrityloxymethyl)-7-hydroxy-3-(1-naphthyl)-2,5-dioxabicyclo[2.2.1]heptane [Compound 15c of Scheme 2]

Dimethoxytritylation of compound 14c (125 mg, 0.46 mmol) using DMTCl (170 mg, 0.5 mmol) in anhydrous pyridine (2 cm$^3$) followed by the general work-up procedure and column chromatography afforded compound 15c as a white solid material (158 mg, 60%); $R_f$ 0.35 (CH$_2$Cl$_2$/MeOH 98:2, v/v); $\delta_H$ (CDCl$_3$) 7.95–7.86 (3 H, m), 7.79 (1 H, d, J 8.3), 7.58–7.41 (9 H, m), 7.35–7.23 (3 H, m), 6.86 (4 H, d, J 8.8), 5.80 (1 H, s), 4.36 (1 H, s), 4.32 (1 H, d, J 6.5), 4.17 (1 H, d, J8.3), 4.06 (1 H, d, J 8.0), 3.78 (6 H, s), 3.62–3.56 (2 H, m), 2.00 (1 H, d, J 6.6); $\delta_c$ (CDCl$_3$) 158.7, 144.9, 136.0, 135.9, 134.5, 133.6, 130.3, 129.8, 129.0, 128.3, 128.2, 128.1, 127.0, 126.5, 125.9, 125.6, 123.9, 122.6, 113.4, 86.6, 85.7, 82.5, 81.7, 73.1, 72.6, 60.2, 55.3; m/z (FAB) 575 [M+H]$^+$, 574 [M]$^+$.

EXAMPLE 15d (1R,3S,4R,7S)-1-(4,4'-Dimethoxytrityloxymethyl)-7-hydroxy-3-(1-pyrenyl)-2,5-dioxabicyclo[2.2.1]heptane [Compound 15d of Scheme 2]

Dimethoxytritylation of the compound 14d (130 mg, 0.38 mmol) using DMTCl (140 mg, 0.42 mmol) in anhydrous pyridine (2 cm$^3$) followed by the general work-up procedure and column chromatography afforded compound 15d as a white solid material (147 mg, 61%); $R_f$ 0.37 (CH$_2$Cl$_2$/MeOH 98:2, v/v); $\delta_H$ (CDCl$_3$) 8.46 (1 H, d, J 8.0), 8.19–8.00 (7 H, m), 7.61 (2 H, dd, J 1.6 and 7.4), 7.48 (4 H, d, J 8.3), 7.35 (2 H, dd, J 7.2 and 7.5), 7.25 (1 H, m), 7.15 (1 H, m), 6.88 (4 H, d, J 9.0), 6.10 (1 H, s), 4.46 (1 H, s), 4.43 (1 H, br s), 4.25 (1 H, d, J 8.1), 4.12 (1 H, d, J 8.1), 3.79 (6H, s), 3.71–3.63 (2 H, m), 2.22 (1 H, br s); $\delta_c$ (CDCl$_3$) 158.7, 149.8, 144.9, 136.1, 136.0, 135.9, 132.1, 131.4, 130.9, 130.6, 130.3, 130.2, 129.2, 129.1, 128.4, 128.3, 128.2, 128.1, 127.5, 127.4, 127.0, 126.9, 126.2, 125.5, 125.4, 124.9, 124.8, 124.7, 123.8, 123.7, 121.9, 113.4, 86.6, 86.1, 83.2, 82.2, 73.2, 72.4, 60.3, 55.3; m/z (FAB) 649 [M+H]$^+$, 648 [M]$^+$.

EXAMPLE 15e (1R,3S,4R,7S)-1-(4,4'-Dimethoxytrityloxymethyl)-7-hydroxy-3-(2,4,5-trimethylphenyl)-2,5-dioxabicyclo[2.2.1]heptane [Compound 15e of Scheme 2]

Dimethoxytritylation of compound 14e (80 mg, 0.3 mmol) using DMTCl (113 mg, 0.33 mmol) in anhydrous pyridine (2 cm$^3$) followed by the general work-up procedure and column chromatography afforded compound 15e as a white solid material (134 mg, 78%); R$_f$ 0.32 (CH$_2$Cl$_2$/MeOH 98:2, v/v); $\delta_H$ (CDCl$_3$) 7.55 (2 H, d, J 7.9), 7.45–7.42 (4 H, m), 7.32–7.21 (4 H, m), 6.93 (1 H, s), 6.84 (4 H, d, J 8.2), 5.20 (1 H, s), 4.40 (1 H, s), 4.08 (1 H, s), 4.04 (1 H, d, J 8.3), 3.95 (1 H, d, J 8.2), 3.78 (6 H, s), 3.56 (1 H, d, J 10.5), 3.47 (1 H, d, J 10.2), 2.24 (3 H, s), 2.22 (3 H, s), 2.19 (3 H, s); $\delta_c$ (CDCl$_3$) 158.6, 145.0, 136.0, 135.7, 134.4, 134.2, 131.8, 131.3, 130.3, 130.2, 128.3, 128.0, 127.2, 126.9, 113.3, 86.4, 85.7, 82.1, 81.8, 73.0, 71.8, 60.2, 55.3, 19.6, 19.3, 18.4; m/z (FAB) 567 [M+H]$^+$, 566 [M]$^+$.

EXAMPLE 16

General Procedure for Synthesis of the Phosphoramidite Derivatives 16a–e as Shown in Scheme 2

2-Cyanoethyl N,N'-diisopropylphosphoramidochloridite was added dropwise to a stirred solution of nucleoside 15a–e and N,N'-diisopropylethylamine (DIPEA) in anhydrous CH$_2$Cl$_2$ at room temperature. After stirring the mixture at room temperature for 6 h, methanol (0.2 cm$^3$) was added and the resulting mixture diluted with EtOAc (20 cm$^3$, containing 0.5% Et$_3$N, v/v). The organic phase was washed, successively, with saturated a. NaHCO$_3$ (2×10 cm$^3$) and brine (10 cm$^3$). The separated organic phase was dried (Na$_2$SO$_4$), filtered and evaporated to dryness under reduced pressure. The residue obtained was purified by column chromatography [25–30% (v/v) EtOAc in n-hexane containing 0.5% Et$_3$N] to give the amidites 16a–e.

EXAMPLE 16a

Synthesis of (1R,3S,4R,7S)-7-[2-Cyanoethoxy(diisopropylamino) phosphinoxy]-1-(4,4'-dimethoxytrityloxymethyl)-3-phenyl-2,5-dioxabicyclo[2.2.1]heptane [Compound 16a of Scheme 2]

Treatment of compound 15a (170 mg, 0.32 mmol) with 2-cyanoethyl N,N'-diisopropylphosphoramidochloridite (85 mg, 0.36 mmol) in the presence of DIPEA (0.4cm$^3$) and anhydrous CH$_2$Cl$_2$ (2.0 cm$^3$) followed by the general work-up procedure and column chromatography afforded phosphoramidite 16a as a white solid material (155 mg, 66%); R$^f$ 0.45, 0.41 (CH$_2$Cl$_2$/MeOH 98:2, v/v); $\delta_P$ (CDCl$_3$) 149.3, 148.9.

EXAMPLE 16b (1R,3S,4R,7S)-7-[2-Cyanoethoxy(diisopropylamino) phosphinoxy]-1-(4,4'-dimethoxytrityloxymethyl)-3-(4-fluoro-3-methylphenyl)-2,5-dioxabicyclo[2.2.1] heptane [Compound 16b of Scheme 2]

Treatment of compound 15b (95 mg, 0.17 mmol) with 2-cyanoethyl N,N'-diisopropylphosphoramidochloridite (53 mg, 0.22 mmol) in the presence of DIPEA (0.3cm$^3$) and anhydrous CH$_2$Cl$_2$ (2.0 cm$^3$) followed by the general work-up procedure and column chromatography afforded phosphoramidite 16b as a white solid material (85 mg, 66%); R$_f$ 0.45, 0.41 (CH$_2$Cl$_2$/MeOH 98:2, v/v); $\delta_P$ (CDCl$_3$) 149.3, 148.8.

EXAMPLE 16c

Synthesis of (1R,3S,4R,7S)-7-[2-Cyanoethoxy(diisopropylamino)phosphinoxy]-1-(4,4'-dimethoxytrityloxymethyl)-3-(1-naphthyl)-2,5-dioxabicyclo [2.2.1]heptane [Compound 1 6c of Scheme 2]

Treatment of compound 5c (158 mg, 0.28 mmol) with 2-cyanoethyl N,N'-diisopropylphosphoramidochloridite (75.7 mg, 0.32 mmol) in the presence of DIPEA (0.4 cm$^3$) and anhydrous CH$_2$Cl$_2$ (2.0 cm$^3$) followed by the general work-up procedure and column chromatography afforded phosphoramidite 16c as a white solid material (127 mg, 60%); R$_f$ 0.47, 0.44 (CH$_2$Cl$_2$/MeOH 98:2, v/v); $\delta_P$ (CDCl$_3$) 149.2, 149.1.

EXAMPLE 16d

Synthesis of (1R,3S,4R,7S)-7-[2-Cyanoethoxy(diisopropylamino) phosphinoxy]-1-(4,4'-dimethoxytrityloxymethyl)-3-(1-pyrenyl)-2,5-dioxabicyclo[2.2.1] heptane [Compound 16d of Scheme 2]

Treatment of compound 15d (140 mg, 0.22 mmol) with 2-cyanoethyl N,N'-diisopropylphosphoramidochloridite (64 mg, 0.27 mmol) in the presence of DIPEA (0.3cm$^3$) and anhydrous CH$_2$Cl$_2$ (2.0 cm$^3$) followed by the general work-up procedure and column chromatography afforded phosphoramidite 16d as a white solid material (124 mg, 68%); R$_f$0.51, 0.47 (CH$_2$Cl$_2$/MeOH 98:2, v/v); 4 (CDCl$_3$) 149.4, 149.1.

EXAMPLE 16e

Synthesis of (1R,3S,4R,7S)-7-[2-Cyanoethoxy(diisopropylamino) phosphinoxy]-1-(4,4'-dimethoxytrityloxymethyl)-3-(2,4,5-trimethylphenyl)-2,5-dioxabicyclo[2.2.1]heptane [Compound 16e of Scheme 2]

Treatment of compound 15e (130 mg, 0.23 mmol) with 2-cyanoethyl N,N'-diisopropylphosphoramidochloridite (64 mg, 0.27 mmol) in the presence of DIPEA (0.3cm$^3$) and anhydrous CH$_2$Cl$_2$ (2.0 cm$^3$) followed by the general work-up procedure and column chromatography afforded phosphoramidite 16e as a white solid material (111 mg, 63%); R$_f$ 0.44, 0.42 (CH$_2$Cl2/MeOH 98:2, v/v); $\delta_P$ (CDCl$_3$) 149.0.

EXAMPLE 17

Synthesis, Deprotection and Purification of Oligonucleotides

All oligomers were prepared using the phosphoramidite approach on a Biosearch 8750 DNA synthesizer in 0.2 μmol scale on CPG solid supports (BioGenex). The stepwise coupling efficiencies for phosphoramidites 16a–c (10 min coupling time) and phosphoramidites 16d and 16e (20 min coupling time) were >96% and for unmodified deoxynucleoside and ribonucleoside phosphoramidites (with standard coupling time) generally >99%, in all cases using 1H-tetrazole as activator. After standard deprotection and cleavage from the solid support using 32% aqueous ammonia (12 h, 55° C.), the oligomers were purified by precipitation from ethanol. The composition of the oligomers were verified by MALDI-MS analysis and the purity (>80%) by capillary gel electrophoresis. Selected MALDI-MS data ([M–H]−; found/calcd.: ON3 2731/2733; ON4 2857/2857; ON6 3094/3093).

EXAMPLE 18

Thermal Denaturation Studies

The thermal denaturation experiments were performed on a Perkin-Elmer UV/NIS spectrometer fitted with a PTP-6 Peltier temperature-programming element using a medium salt buffer solution (10 mM sodium phosphate, 100 mM sodium chloride, 0.1 mM EDTA, pH 7.0). Concentrations of 1.5 mM of the two complementary strands were used assuming identical extinction coefficients for modified and unmodified oligonucleotides. The absorbance was monitored at 260 nm while raising the temperature at a rate of 1° C. per min. The melting temperatures ($T_m$ values) of the duplexes were determined as the maximum of the first derivatives of the melting curves obtained.

EXAMPLE 19

Synthesis of Compounds 16a–16e and Oligomers Containing Monomers 17a–17e

LNA containing the derivatives 17a–17e (FIG. 1, Table 1, Scheme 1, Scheme 2), were synthesized, all based on the LNA-type 2'-O,4'-C-methylene-βD-ribofuranosyl moiety which is known to adopt a locked C3'-endo RNA-like furanose conformation [S. Obika, D. Nanbu, Y. Hari, K. Morio, Y. In, T. Ishida, and T. Imanishi, *Tetrahedron Lett.*, 1997, 38, 8735; S. K. Singh, P. Nielsen, A. A. Koshkin and J. Wengel, *Chem. Commun.*, 1998, 455; A. A. Koshkin, S. K. Singh, P. Nielsen, V. K. Rajwanshi, R. Kumar, M. Meldgaard, C. E. Olsen and J. Wengel, *Tetrahedron*, 1998, 54, 3607; S. Obika, D. Nanbu, Y. Hari, J. Andoh, K. Morio, T. Doi and T. Imanishi, *Tetrahedron Lett.*, 1998, 39, 5401]. The syntheses of the phosphoramidite building blocks 16a–16e suitable for incorporation of the LNA-type aryl C-glycosides 17a–17e are shown in Scheme 1 and Scheme 2 and described in details in the experimental section. In the design of an appropriate synthetic route, it was decided to utilize a reaction similar to one described recently in the literature. Thus, stereoselective attack of Grignard reagents of various heterocycles on a carbonyl group of an aldehyde corresponding to aldehyde 11 (Scheme 2) but with two O-benzyl groups instead of the two p-methoxybenzyl groups of aldehyde 11 (Scheme 2) has been reported to furnish locked-C-nucleosides [S. Obika, Y. Hari, K. Morio and T. Imanishi, *Tetrahedron Lett.*, 2000, 41, 215; S. Obika, Y. Hari, K. Morio and T. Imanishi, *Tetrahedron Lett.*, 2000, 41, 221]. The key intermediate in the synthetic route selected herein, namely the novel aldehyde 11 was synthesized from the known furanoside 1 [R. Yamaguchi, T. Imanishi, S. Kohgo, H. Horie and H. Ohrui, *Biosci. Biotechnol. Biochem.*, 1999, 63, 736] following two different routes. In general, O-(p-Methoxy)benzyl protection was desirable instead of O-benzyl protection as removal of the benzyl protection at a later stage (i.e. 13→14) could also likely result in the cleavage of the benzylic O—$C_1$ bond present, e.g., in compounds 13 and 14 (Scheme 2). In one route to give aldehyde 11, regioselective p-methoxybenzylation of the furanoside 1, followed by mesylation and methanolysis yielded the anomeric mixture of the methyl furanosides 9. Base induced cyclization followed by acetyl hydrolysis afforded the aldehyde 11 in approximately 24% overall yield from 1 (Scheme 1 and Scheme 2). This yield was improved to following a different strategy. Thus, di-O-mesylation of 1 followed by methanolysis and base induced intramolecular nucleophilic attack from the 2-OH group afforded the cyclized anomeric mixture of methyl furanoside 4. Substitution of the remaining mesyloxy group of 4 with an acetate group, followed by deacetylation, p-methoxybenzylation and then acetyl hydrolysis afforded the required aldehyde 11 (Scheme 1).

Coupling of the aldehyde 11 with different aryl Grignard reagents yielded selectively one epimer of each of the compounds 12a–e in good yields (see experimental section for further details on this and other synthetic steps). Each of the diols 12a–e was cyclized under Mitsunobu conditions (TMAD, $PBu_3$) to afford the bicyclic β-C-nucleoside derivatives 13a–e. Oxidative removal of the p-methoxybenzyl protections was achieved in satisfactory yields using DDQ. Subsequent, selective 4,4'-dimethoxytritylation (to give compounds 15a–e) followed by phosphorylation afforded the phosphoramidite building blocks 16a–e in satisfactory yields. The configuration of compounds 13, and thus also compounds 11, 12 and 14–17 were assigned based on 1H NMR spectroscopy, including NOE experiments.

All oligomers were prepared in the 0.2 μmol scale using the phosphoramidite approach. The stepwise coupling efficiencies for phosphoramidites 16a-c (10 min coupling time) and phosphoramidites 16d and 16e (20 min coupling time) were >96% and for unmodified deoxynucleoside and ribonucleoside phosphoramidites (with standard coupling time) generally >99%, in all cases using 1H-tetrazole as activator. After standard deprotection and cleavage from the solid support using 32% aqueous ammonia (12 h, 55° C.), the oligomers were purified by precipitation from ethanol. The composition of the oligomers were verified by MALDI-MS analysis and the purity (>80%) by capillary gel electrophoresis.

EXAMPLE 20

Thermal Denaturation Studies to Evaluate Hybridization Properties

The hybridization of the oligonucleotides ON1–ON11 (Table 1 below) toward four 9-mer DNA targets with the central base being each of four natural bases were studied by thermal denaturation experiments ($T_m$ measurements; see the experimental section for details). Compared to the DNA reference ON1, introduction of one abasic LNA monomer $Ab^L$ (ON2) has earlier been reported to prevent the formation of a stable duplex above 0° C. (only evaluated with adenine as the opposite base) [L. Kværnø and J. Wengel, *Chem. Commun.*, 1999, 657]. With the phenyl monomer 17a (ON3), $T_m$ values in the range of 5–12° C. was observed. Thus, the phenyl moiety stabilizes the duplexes compared to $Ab^L$, but universal hybridization is not achieved as a preference for a central adenine base in the complementary target strand is indicated (Table 1). In addition, significant destabilization compared to the ON1:DNA reference duplex was observed. Results similar to those obtained for ON3 were obtained for oligomers isosequential with ON3 but containing 17b, 17c or 17e instead of 17a as the central monomer (Table 1, ON7, ON8 and ON9, respectively).

TABLE 1

Thermal denaturation experiments
($T_m$ values shown)
for ON1–ON11 towards DNA complements with each of
the four natural bases in the central position[a]

| DNA target: 3'-d(CACTYTACG) Y: | A | C | G | T |
|---|---|---|---|---|
| ON1  5'-d(GTGATATGC) | 28 | 11 | 12 | 19 |
| ON2  5'-d(GTGAAb$^L$ATGC) | <3 | n.d. | n.d. | n.d. |
| ON3  5'-d(GTGA17aATGC) | 12 | 5 | 6 | 7 |
| ON4  5'-d(GTGA17dATGC) | 18 | 17 | 18 | 19 |
| ON5  5'-d[2'-OMe(GTGATATGC)] | 35 | 14 | 19 | 21 |
| ON6  5'-d[2'-OMe(GT$^L$GA17dAT$^L$GC)] | 39 | 38 | 37 | 40 |
| ON7  5'-d(GTGA17bATGC) | 15 | 7 | 6 | 8 |
| ON8  5'-d(GTGA17cATGC) | 15 | 7 | 6 | 9 |
| ON9  5'-d(GTGA17eATGC) | 13 | 6 | 6 | 7 |
| ON10 5'd[2'-OMe(GT$^L$GA17bAT$^L$GC)] | 31 | 25 | 26 | 27 |
| ON11 5'd[2'-OMe(GT$^L$GA17cAT$^L$GC)] | 34 | 27 | 27 | 32 |

[a]Melting temperatures ($T_m$ values/° C.) measured as the maximum of the first derivative of the melting curve ($A_{260}$ vs temperature) recorded in medium salt buffer (10 mM sodium phosphate, 100 mM sodium chloride, 0.1 mM EDTA, pH 7.0) using 1.5 μM concentrations of the two strands; A = adenine monomer, C = cytosine monomer, G = guanine monomer, T = thymine monomer; See FIG. 1 and/or Scheme 2 for structures of T$^L$, Ab$^L$ and 17a–17e; DNA sequences are shown as d(sequence) and 2'-OMe-RNA sequences as 2'-OMe (sequence); "n.d." denotes "not determined". The data reported for ON1 have been reported earlier [A. A. Koshkin, S. K. Singh, P. Nielsen, V. K. Rajwanshi, R. Kumar, M. Meldgaard, C. E. Olsen and J. Wengel, Tetrahedron, 1998, 54, 3607]. The data reported for ON2 has been reported earlier [L. Kvaernø and J. Wengel, Chem. Commun., 1999, 657].

The pyrene LNA nucleotide 17d (in ON4) displays more encouraging properties (Table 1). Firstly, the binding affinity towards all four complements is increased compared to ON3 (containing 17a). Secondly, universal hybridization is observed as shown by the four $T_m$ values all being within 17–19° C. With respect to universal hybridization, 17d thus parallels the pyrene DNA derivative Py [T. J. Matray and E. T. Kool, J. Am. Chem. Soc., 1998, 120, 6191], but the decrease in thermal stability compared to the ON1:DNA reference is more pronounced for 17d (~10° C.) than reported for Py (~5° C. in a 12-mer polypyrimidine DNA sequence) [T. J. Matray and E. T. Kool, J. Am. Chem. Soc., 1998, 120, 6191]. It therefore appears that stacking (or intercalation) by the pyrene moiety is not favored by the conformational restriction of the furanose ring of 17d, although comparison of the thermal stabilities of ON2, ON3 and ON4 strongly indicate interaction of the pyrene moiety within the helix.

When measured against an RNA target [3'-r(CACUAUACG)], the $T_m$ values (using identical experimental conditions as for the experiments descried above) of ON3 was 11.9° C. and of ON4 was 12.7° C. For oligomers ON7, ON8 and ON9 (Table 1), the corresponding $T_m$ values were 11.7, 8.8 and 10.2° C., respectively.

EXAMPLE 21

The Effect of Pyrene LNA Units in an RNA-Like Strand

ON5, ON6, ON10 and ON11 (see Table 1 above), were synthesized. The former being composed entirely of 2'-OMe-RNA monomers and the latter three of six 2'-OMe-RNA monomers (see FIG. 1), two LNA thymine monomers T$^L$ (see FIG. 1), and one central LNA pyrene monomer 17d (oligomer ON6), or one central monomer 17b (ON10) or 17c (ON1). A sequence corresponding to ON6 but with three T$^L$ monomers has earlier been shown to form a duplex with complementary DNA of very high thermal stability. ON6 is therefore suitable for evaluation of the effect of introducing high-affinity monomers around a universal base. As seen in Table 1, the 2'-OMe-RNA reference ON5 binds to the DNA complement with slightly increased thermal stability and conserved Watson-Crick discrimination (compared to the DNA reference ON1). Indeed, the LNA/2'-OMe-RNA chimera ON6 displays universal hybridization behavior as revealed from the four $T_m$ values (37, 38, 39 and 40° C.). All four $T_m$ values obtained for ON6 are higher than the $T_m$ values obtained for the two fully complementary reference duplexes ON1:DNA ($T_m$=28° C.) and ON5:DNA ($T_m$=35° C.).

These novel data demonstrate that the pyrene LNA monomer 17d display universal hybridization behavior both in a DNA context (ON4) and in an RNA-like context (ON6), and that the problem of decreased affinity of universal hybridization probes can be solved by the introduction of high-affinity monomers, e.g. 2'-OMe-RNA and/or LNA monomers. Increased affinities compared to ON7 and ON8 were obtained for ON10 and ON11, respectively, but universal hybridization behavior was not obtained as a preference for a central adenine base in the complementary target strand is indicated (Table 1 above).

EXAMPLE 22

Base-Pairing Selectivity in Hybridization Probes

A systematic thermal denaturation study with ON6 (Table 2) was performed to determine base-pairing selectivity. For each of the four DNA complements (DNA target strands; monomer Y=A, C, G or T) used in the study shown in Table 1 above, ON6, containing a central pyrene LNA monomer 17d, was hybridized with all four base combinations in the neighboring position towards the 3'-end of ON6 (DNA target strands; monomer Z=A, C, G or T, monomer X=T) and the same towards the 5'-end of ON6 (DNA target strands; monomer X=A, C, G or T, monomer Z=T). In all eight subsets of four data points, satisfactory to excellent Watson-Crick discrimination was observed between the match and the three mismatches (Table 2 below, $\Delta T_m$ values in the range of 5–25° C.).

TABLE 2

Thermal denaturation experiments ($T_m$ values shown)
to evaluate the base-pairing selectivity of the
bases neighboring the universal pyrene LNA monomer
17d in the 2'-OMe-RNA/LNA chimera ON6.
In the target strand [3'-d(CAC-XYZ-ACG)], the
central three bases XYZ are varied among each of
the four natural bases[a]
5'-[2'-OMe(GT$^L$G-A17dA-T$^L$GC)]
3'-d(CAC-XYZ-ACG)

| XYZ | $T_m$/° C. | XYZ | $T_m$/° C. | XYZ | $T_m$/° C. | XYZ | $T_m$/° C. |
|---|---|---|---|---|---|---|---|
| TAA | 26 | TCA | 22 | TGA | 22 | TTA | 29 |
| TAC | 26 | TCC | 29 | TGC | 26 | TTG | 31 |
| TAG | 24 | TCG | 24 | TGG | 30 | TTC | 32 |
| TAT | 39 | TCT | 38 | TGT | 37 | TTT | 40 |
| AAT | 18 | ACT | 27 | AGT | 22 | ATT | 28 |
| CAT | 30 | CCT | 31 | CGT | 27 | CTT | 35 |

TABLE 2-continued

Thermal denaturation experiments ($T_m$ values shown) to evaluate the base-pairing selectivity of the bases neighboring the universal pyrene LNA monomer 17d in the 2'-OMe-RNA/LNA chimera ON6.
In the target strand [3'-d(CAC-XYZ-ACG)], the central three bases XYZ are varied among each of the four natural bases[a]
5'-[2'-OMe(GT$^L$G-A17dA-T$^L$GC)]
3'-d(CAC-XYZ-ACG)

| XYZ | $T_m$/° C. | XYZ | $T_m$/° C. | XYZ | $T_m$/° C. | XYZ | $T_m$/° C. |
|---|---|---|---|---|---|---|---|
| GAT | 14 | GCT | 28 | GGT | 16 | GTT | 27 |
| TAT | 39 | TCT | 38 | TGT | 37 | TTT | 40 |

[a]See caption below Table 1 for abbreviations and conditions used; The data for matched neighboring bases (X = Z = T) are shown in bold.

The results reported herein have several important implications for the design of probes for universal hybridization: (1) Universal hybridization is possible with a conformationally restricted unit as demonstrated for the pyrene LNA unit; (2) Universal hybridization behavior is feasible in an RNA context; (3) The binding affinity of probes for universal hybridization can be increased by the introduction of high-affinity monomers without compromising the universal hybridization and the base-pairing selectivity of bases neighboring the universal base.

Based on the results reported herein, that chimeric oligonucleotides comprising pyrene and other known universal bases attached at various backbones (e.g. LNA-type units, ribofuranose units, deoxyribose units, or other sugar units such as xylose units in 2'-OMe-RNA/LNA chimeric oligos) likewise will display attractive properties with respect to universal hybridization behavior. For example, an oligomer identical with the 2'-OMe-RNA/LNA oligo ON6 but with the 17d monomer substituted by a pyrenyl-2'-OMe-ribonucleotide monomer.

EXAMPLE 23

Chimeric Oligonucleotides

These chimeric oligonucleotides are comprised of pyrene and other known universal bases attached at various backbones (e.g. LNA-type units, ribofuranose units, or deoxyribose units, or other sugar units such as xylose units in 2'-OMe-RNA/LNA oligos). Experimentation with these chimeric oligonucleotides are for evaluating the possibility of obtaining similar results to the 2'-OMe-RNA/LNA oligo ON6 at a lower cost, for example, by substituting Py$^L$ with a pyrenyl-2'-OMe-ribonucleotide monomer.

EXAMPLE 24

Improved Reverse Transcription Using Pyrene-LNA-Anchored Oligo(T) Priming (T-20VN Anchor Primer)

The isolation of intact mRNA from eukaryotic cells and the subsequent conversion of the poly(A)+ mRNA to double-stranded complementary DNA (cDNA) are essential tools for a number of molecular biological applications including RT-PCR, full-length cDNA cloning and sequencing, expression cloning, EST sequencing, and expression profiling using, e.g., Northern blot analysis or expression microarrays. Most eukaryotic mRNAs carry a tract of polyadenylic acid units forming the so-called poly(A) tails at their 3'-ends. The mRNA isolation relies on the ability of the poly(A) tails to form stable dT-A base pairs with oligo-dT coupled onto a matrix, such as oligo(dT) cellulose, under high salt conditions. The polyadenylated mRNA can be selected from the total RNA preparation by affinity chromatography on oligo(dT) cellulose-packed columns by batch binding and elution or by binding onto oligo(dT)-coated magnetic particles. Following washing of the matrix or particles, the poly(A)+RNAs are eluted using TE buffer or diethylpyrocarbonate-treated water. The first strand cDNA is synthesized by an RNA-dependent DNA polymerase, the so-called reverse transcriptase (RT), using poly(A)+RNA as a template and typically an oligo(dT) oligonucleotide as a primer.

The present method describes the use of Pyrene-LNA anchored oligo(T) oligonucleotide primers in first strand cDNA synthesis resulting in improved reverse transcription of eukaryotic mRNA. The method addresses three problems observed upon the use of standard DNA oligo(dT) primers in reverse transcription: (i) efficient priming on eukaryotic mRNAs with short poly(A) tails, (ii) efficient anchoring of the oligo(T) primer by the Pyrene-LNA and LNA-C/G/T units resulting in an improved T20-VN anchor primer and thus avoiding reverse transcription of long poly(A) tracts, and (iii) improved reverse transcription of eukaryotic poly (A)+RNA directly from total RNA extracts due to increased specificity.

EXAMPLE 24a

Improved Reverse Transcription Using Pyrene-LNA-Anchored Oligo(T)$_{20}$ (T-20-VN Anchor Primer) in the First Strand cDNA Synthesis

TABLE 3

Pyrene-anchored oligo(T) primers for reverse transcription of poly(A) + RNA, in which "17d" refers to compound 17d.

| Oligo Name: | Sequence |
|---|---|
| ON12 | 5'-T$^L$TT$^L$TT$^L$TT$^L$TT$^L$TT$^L$TT$^L$TT$^L$TT$^L$TT$^L$TV$^L$17d-3' |
| ON13 | 5'-TT$^L$TTT$^L$TTT$^L$TTT$^L$TTT$^L$TTT$^L$TTTV$^L$17d-3' |
| ON14 | 5'- d[2'-OMe(T$^L$TT$^L$TT$^L$TT$^L$TT$^L$TT$^L$TT$^L$TT$^L$TT$^L$TT$^L$TV$^L$17d)]-3' |
| ON15 | 5'-TTTTTTTTTTTTTTTTTTTTV$^L$17d-3' |

V = A or C or G

Combine in an RNase-free microcentrifuge tube:

A. Total RNA template

10–20 mg of total RNA 5 mg anchored oligo(T) primer of the invention (ON12 or ON13 or ON14 or ON15, Table 3)

DEPC-water to 12 ml final volume or

B. Poly(A)+RNA template

1–5 mg of poly(A)+ RNA 5 mg anchored oligo(dT) primer of the invention (ON12 or ON13 or ON14 or ON15, Table 3)

DEPC-water to 12 ml final volume

Heat the reaction mixture at 70° C. for 10 minutes, quench on ice for 2–5 minutes, spin 20 seconds (Picofuge), add the following: 1 ml Superasin (RNAse inhibitor, 20 U/ml, Ambion, USA), 4 ml 5×RTase buffer (Invitrogen, USA), 2 ml 0.1 M DTT (Invitrogen, USA), 1 ml dNTP (10 mM dATP, dGTP, dTTP, dCTP, Pharmacia).

Add 1 ml of Superscript II RTase (Invitrogen, USA, 200 U/ml); mix well (no air bubbles). Incubate for 1 hour at 45° C. Add additional 1 ml Superscript II RTase and continue incubation for an additional 1 hour at 45° C., heat at 70° C. for 5 minutes, quench on ice for 2 minutes.

The first-strand cDNA sample can be stored at −20° C. until used.

Place the microcentrifuge tube on ice for 2 minutes, then cleanup the cDNA prep by gel filtration using a MicroSpin S-400 HR column as follows: Pre-spin the column 1 minute at 735×g in a 1.5 ml tube (Ole Dich Eppendorf microcentrifuge program # 30), place the column in a new 1.5 ml tube and slowly apply the mRNA::cDNA sample to the top centre of the resin, spin at 735×g for 2 minutes, collect the eluate and check volume. Continue directly with second strand synthesis.

B. Poly(A)+RNA template

1–5 mg of poly(A)+ RNA 5 mg anchored oligo(dT) primer of the invention (ON12 or ON13 or ON14 or ON15, Table 3)

DEPC-water to 9 ml final volume.

Heat the reaction mixture at +70° C. for 10 minures, quench on ice 5 minutes, spin 20 seconds (Picofuge), then add the following: 1 ml Superasin (RNAse inhibitor, 20 U/ml, Ambion, USA), 10 ml 5×RTase buffer (Invitrogen, USA), 5 ml 0.1 M DTT (Invitrogen, USA), 5 ml 10 mM dNTP (Pharmacia, in DEPC-DDIW), 15 ml 80% trehalose (in DEPC-DDIW, heat to dissolve prior to use).

Add 5 ml of Superscript II RTase (BRL, 200 U/ml), mix well (no air bubbles), then put the tube quickly on a thermal cycler with a hot lid (e.g. MJ Research DNA Engine). Alternatively, use a thermostable reverse transcriptase, such as the Tth polymerase (Roche, USA) or Tfl polymerase (Promega, USA) according to the manufacturers instructions by simultaneously omitting trehalose from the first strand reaction mixture. Synthesize first-strand cDNA using the following program:

Step 1: +45° C. for 2 minutes (hot start)

Step 2: negative ramp: go to 35° C. in 1 minute (gradient annealing)

Step 3: 35° C. for 2 minutes (complete annealing)

Step 4: 45° C. for 5 minutes

Step 5: Positive ramp: +15° C. (until 60° C.) at +0.1° C./sec

Step 6: 55° C. for 2 minutes

Step 7: 60° C. for 2 minutes

Step 8: Go to step 6 for 10 additional times

Step 9: +4° C. identically

Place the PCR tube on ice for 2 minutes, then remove the unincorporated dNTPs by gel filtration using a MicroSpin EXAMPLE 24b Improved trehalose-stimulated first strand cDNA synthesis using Pyrene-LNA-anchored oligo(T)20 primer in the reverse transcription Oligo Name: Sequence ON12    5'-T$^L$TT$^L$TT$^L$TT$^L$TT$^L$TT$^L$TT$^L$TT$^L$TT$^L$TT$^L$TT$^L$TV$^L$17d-3'

ON13    5'-TT$^L$TTT$^L$TTT$^L$TTT$^L$TTT$^L$TTTV$^L$17d-3'

ON14    5'-d[2'OMe(T$^L$TT$^L$TT$^L$TT$^L$TT$^L$TT$^L$TT$^L$TT$^L$TT$^L$TT$^L$TT$^L$TV$^L$17d)]-3'

ON15    5'-TTTTTTTTTTTTTTTTTTTTV$^L$17d-3'

V = A or C or G

Combine in an RNase free, pre-siliconized 0.5 ml PCR tube (Ambion):

A. Total RNA template

10–20 mg of total RNA 5 mg anchored oligo(T) primer of the invention (ON12 or ON13 or ON14 or ON15, Table 3)

DEPC-water to 9 ml final volume or

S-400 HR column (Pharmacia, USA) as follows: Pre-spin the column 1 minute at 735×g in a 1.5 ml tube, place the column in a new 1.5 ml tube and slowly apply the mRNA::cDNA sample to the top centre of the resin, spin at 735×g for 2 minutes, collect the eluate and check volume. Continue directly with second strand synthesis, PCR, or other applications.

EXAMPLE 24c

Improved Fluorochrome-Labelling of First Strand cDNA Using Pyrene-LNA-Anchored Oligo(T)20 Primer

TABLE 4

Pyrene-anchored oligo(T) primers for fluorochrome-labeling of first strand cDNA.

| Oligo Name: | Sequence |
|---|---|
| ON12 | 5'-T$^L$TT$^L$TT$^L$TT$^L$TT$^L$TT$^L$TT$^L$TT$^L$TT$^L$TT$^L$TT$^L$TV$^L$17d-3' |
| ON13 | 5'-TT$^L$TTT$^L$TTT$^L$TTT$^L$TTT$^L$TTT$^L$TTTV$^L$17d-3' |
| ON14 | 5'-d[2'-OMe(T$^L$TT$^L$TT$^L$TT$^L$TT$^L$TT$^L$TT$^L$TT$^L$TT$^L$TT$^L$TT$^L$T17d)]-3' |
| ON15 | 5'-TTTTTTTTTTTTTTTTTTTTV$^L$17d-3' |

V = A or C or G

Combine in an RNase-free microcentrifuge tube:
A. Total RNA template
10–20 mg of total RNA
5 mg anchored oligo(T) primer of the invention (ON12 or ON13 or ON14 or ON15, Table 4)
DEPC-water to 8 ml final volume or
B. Poly(A)+RNA template
1 mg of poly(A)+ RNA
5 mg anchored oligo(T) primer of the invention (ON12 or ON13 or ON14 or ON15, Table 4)
DEPC-water to 8 ml final volume.

Heat the reaction mixture at 70° C. for 10 minutes, quench on ice for 2–5 minutes, spin 20 seconds (Picofuge), add the following: 1 ml Superasin (RNAse inhibitor, 20 U/ml, Ambion, USA), 4 ml 5×RTase buffer (Invitrogen, USA), 2 ml 0.1 M DTT (Invitrogen, USA), 1 ml dNTP (20 mM dATP, dGTP, dTTP; 4 mM dCTP, Pharnacia), 3 ml Cy3-dCTP or Cy5-dCTP (Amersham, USA).

Add 1 ml of Superscript II RTase (Invitrogen, USA, 200 U/ml); mix well (no air bubbles), Incubate for 1 hour at 42° C. Add additional 1 ml Superscript II RTase and continue incubation for an additional 1 hour at 42° C., heat at 70° C. for 5 minutes, quench on ice for 2 minutes. The labelled first-strand cDNA sample can be stored in the dark at −20° C. until used.

Remove the unincorporated Cy-dCTP by gel filtration using a MicroSpin S-400 HR column as follows: Pre-spin the column 1 minute at 1500×g in a 1.5 ml tube, place the column in a new 1.5 ml tube and slowly apply the labelled cDNA sample to the top centre of the resin, spin at 1500×g for 2 minutes, collect the eluate, and continue with RNA hydrolysis.

Degrade RNA by adding 3 ml of 0.5 M NaOH, mix well, and incubate at 70° C. for 15 minutes, neutralize by adding 3 ml of 0.5 M HCl and mix well. Add 450 ml 1×TE, pH 7.5 to the neutralized sample and transfer onto a Microcon-30 concentrator (prior to use, spin 500 ml 1×TE through the column to remove residual glycerol). Spin the samples at 14000×g in a microcentrifuge for 12–14 minutes, and check volume. Continue until volume is reduced to 5 ml. Elute the labeled cDNA probe by inverting the Microcon-30 tube and spinning at 1000×g for 3 minutes, check Microcon filter for proper elution. Combine the Cy3/Cy5-labelled cDNA samples in one tube (ca. 10 ml), then add 3.75 ml 20×SSC (3×SSC final, pass through 0.22 m filter prior to use to remove particulates) yeast tRNA (1 mg/ml final) 0.625 ml 1 M HEPES, pH 7.0 (25 mM final, pass through 0.22 m filter prior to use to remove particulates) 0.75 ml 10% SDS (0.3% final) DEPC-DIW to 25 ml final volume.

Filter the labelled cDNA target sample in Millipore 0.22 micron spin column (Ultrafree-MC, cat. no. UFC30HV25). Wet filter first with 20 ul of DEPC-treated water and spin 1 minute, remove water before adding probe. Incubate reaction at 100° C. for 2–5 minutes. Cool at room temp for 2–5 minutes by spinning at max speed in a microcentrifuge. Apply to prepared microarray under Lifter-Slip (Erie Scientific, USA). Add 20–30 ml of 3×SSC to both ends of the slide chamber. Seal in watertight hybridization chamber (eg. DieTech, USA) and incubate at 65° C. for 16–18 hours.

EXAMPLE 25

Screening and Cloning of Protein and Enzyme Families Using Degenerated Pyrene-LNA-Modified PCR Primers Most proteins and enzymes can be classified on the basis of similarities in their primary sequences into a limited number of families. Proteins or protein domains belonging to a particular family generally share functional attributes and are derived from a common ancestor. It is apparent, when studying protein sequence families, that some regions have been better conserved than others during evolution. These regions are generally important for the function of a protein and/or for the maintenance of its three-dimensional structure. By analyzing the constant and variable properties of such groups of similar sequences, it is possible to derive a signature for a given protein family or domain, which distinguishes its members from all other unrelated proteins. While the signature sequences can be used to assign a newly identified and sequenced protein to a specific protein or enzyme family, these conserved signatures also form a highly useful basis for the design of degenerated oligonucleotide probes that can be used to screen for related proteins or enzymes in a wide variety of different species within prokaryotes, Archae and eukaryotes.

The present method describes the use of degenerated Pyrene-LNA modified oligonucleotide primers in screening by polymerase chain reaction of conserved signature sequences in protein and enzyme families. The identified PCR fragments hereof can be used to obtain the corresponding full-length cDNAs or genes encoding the complete protein and enzyme sequences. An example of the use of the present method for PCR screening of glycohydrolase family 45 genes in bacteria, Archea, and fungi is given below. The present method can be applied to detection of any conserved signature sequences in a given protein or enzyme family for which multiple amino acid sequence alignment data (more than a single sequence entry) is available. The following lists 9 examples for which the available multiple sequence alignment data on the Pfam Protein family database of alignments and Hidden Markov Models published by The Wellcome Trust Sanger Institute, Wellcome Trust Genome Campus, Hinxton, Cambs, CB10 1SA UK (web address: http://www.sanger.ac.uk/Software/Pfam/browse/top_twenty.shtml) demonstrates the presence of conserved signature sequences for the design of Pyrene-LNA modified degenerated oligonucleotide probes or PCR primers:

1. Retroviral aspartyl protease (accession number PF00077)
2. Protein kinase domain, in eg. eukaryotic protein kinases, such as the rat map kinase erk2 (accession number PF00069)
3. Hepatitis C virus non-structural protein E2/NS1 (accession number PF01560)
4. Archaeal ATPase (accession number PF01637)
5. Homeobox-associated leusine zipper (PF02183)
6. Apoptosis-preventing protein (PF02331)
7. DNA repair protein rad10 (PF03834)
8. Glycohydrolase family 11 (PF00457)
9. Glycohydrolase family 12 (PF01670)

taining oligonucleotide primers for screening of the glycohydrolase family 45 genes in biological samples, such as bacteria, Archaea, and fungi.

Signature sequence I (SEQ ID NO: 10) and the corresponding degenerated oligonucleotide sequence (SEQ ID NOs: 1–3):

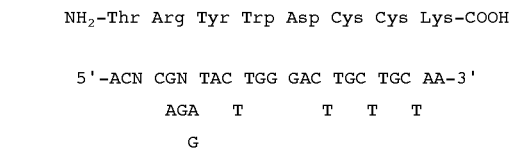

Signature sequence II (SEQ ID NO: 11) and the corresponding degenerated oligonucleotide sequence (SEQ ID NOs: 4–9):

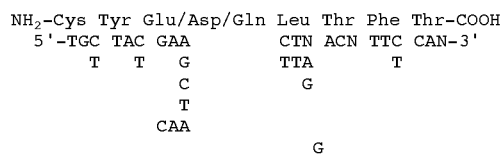

TABLE 5

Pyrene-LNA modified degenerated PCR primers corresponding to conserved signature amino acid sequences in the glycohydrolase family 45.

| Oligo Name: | Sequence |
|---|---|
| ON16 | 5'-AC$^L$17d17dG17dTA$^L$17dTGGGA$^L$17dTG$^L$17dAA-3' |
| ON17 | 5'-d[2'-OMe(AC$^L$17d17dG17dTA$^L$17dTGGGA$^L$17dTG$^L$17dTG$^L$17dAA)]-3' |
| ON18 | 5'-AC17d17dG17dTA$^L$17dTGGGA17dTG$^L$17dTG17dAA-3' |
| ON19REV | 5'-GT$^L$17dAA$^L$17dGT$^L$17dkA$^L$17d17dT$^L$17d17dT$^L$17dCA-3' |
| ON20REV | 5'-d[2'-OMe(GT$^L$17dAA$^L$17dGT$^L$17dA$^L$17d17dT$^L$17d17dTA$^L$17dCA)]-3' |
| ON21REV | 5'-GT17dAA$^L$17dGT$^L$17dA$^L$17d17dT$^L$17d17dTA17dCA-3' |

N = A or C or G or T

EXAMPLE 25a

PCR Screening of Glycohydrolase Family 45 Genes from Bacteria, Archea and Fungi Using Pyrene-LNA Modified Degenerated Oligonucleotide Primers 1A. Design of pyrene-LNA modified degenerated PCR primers corresponding to conserved signature amino acid sequences in the glycohydrolase family 45.

The multiple sequence alignment of the 30 entries representing enzyme sequences belonging to the glycohydrolase family 45 in the Pfam Protein family database of alignments and Hidden Markov Models (web address: http://www.sanger.ac.uk/Software/Pfam/browse/top_twenty.shtml) was used to pinpoint two highly conserved regions within the enzyme family. These signature sequences were used as basis for the design of two degenerated pyrene-LNA con- 1B. Isolation of Genomic DNA Genomic DNA from the biological samples is isolated using the DNeasy Tissue Kit or DNeasy Plant Kit according to the manufacturer's instructions (Qiagen, USA), or using the FastDNA Kit or FastDNA Kit for soil and the FastPrep FP120 instrument according to the manufacturer's instructions (Q-BIOgene, USA).

1C. Generation of First Strand cDNA from Eukaryotic Poly(A)+RNA Using RT-PCR

Combine in an RNase-free microcentrifuge tube (Ambion, USA):

A. Total RNA template
0.1–1 mg of total RNA
5 mg anchored oligo(dT) primer (20TVN)
DEPC-water to 8 mL final volume
Or
B. Poly(A)+RNA template
10–100 ng of poly(A)+ RNA
5 mg anchored oligo(dT) primer (20TVN)

5 mg random pd(N)6 primer
DEPC-water to 8 mL final volume

Heat at 70° C. for 10 minutes, quench on ice for 2–5 minutes, and spin for 20 seconds at max speed.

If desired, 10 ng of HeLa total RNA from Invitrogen's "RT-PCR Primer and Control Set" (cat # 10929–016, Invitrogen, USA) can be included as a positive control. Add to the reaction mixture:

1 µL Superasin (RNAse inhibitor, 20 U/µL, Ambion)
4 µL 5× RT buffer (Invitrogen)
2 µL 0.1 M DTT (Invitrogen)
1 µL dNTP (20 mM dATP, dGTP, dTTP, dCTP, Pharmacia)
1 µL of Superscript II RT (Invitrogen, 200 U/ml), mix well (no air bubbles).

Incubate for 1 hour at 45° C. Add additional 1 µL Superscript II RTase and continue incubation for an additional 1 hour at 45° C. Heat at 70° C. for 5 minutes, and quench on ice for 2 minutes. Remove unincorporated nucleotides, primers, etc. using a spin column, according to supplier's instructions. Sephacryl S-400 (Qiagen, USA) works well for this purpose. Pre-spin the column 1 minute at 735×g in a 1.5 ml tube, place the column in a new 1.5 ml tube and slowly apply the mRNA::cDNA sample to the top centre of the resin, spin at 735×g for 2 minutes, collect the eluate, and check volume. Dilute the eluate to 5×starting volume and use 1 µL and 5 µL as template for the subsequent PCR amplification. The first-strand cDNA sample can be stored at −20° C. until used.

1D. In Vitro Amplification of Genomic DNA and Double-Stranded cDNA

Set-up a standard PCR amplification using the DNA polymerase of choice (the example below is used for the Pfx DNA polymerase from Invitrogen), 1–5 µL template (from RT-PCR reaction above) or 100–200 ng of genomic DNA
5 µL 10×Pfx buffer
1 µL MgSO$_4$
5 µL dNTP mix (2 mM of each dATP, dCTP, dGTP, and dTTP, Pharmacia, USA)
1 µL forward primer (10–20 µM of ON16 or ON17 or ON 18, Table 5)
1 µL reverse primer (10–20 µM of ON19REV or ON20REV or ON21 REV, Table 5)
0.5 µL Pfx
H$_2$O→50 µL final volume If the HeLa RNA was included in the room temperature reaction, set-up separate PCR reactions using the supplied β-actin control primers.

Set-up the PCR machine to run 30–40 cycles where annealing temperature and extension temperature reflect the primers and the polymerase of choice. Adjust extension time according to the estimated length of the PCR product (estimated from the multiple sequence alignment).

The following protocol is given as an example and works well for Invitrogen's (Invitrogen, USA) "RT-PCR Primer and Control Set":

94° C. for 5 minutes
40 cycles of (94° C./1 min, 50° C./1 min, 68° C./2 min)
10° C. indefinitely Analyse a sample (1–5 µL) from each PCR reaction on an agarose gel with, e.g., HaeIII-digested φX174 RF DNA as a size marker. The PCR fragment of interest is excised from the gel and cloned into the pCR cloning vector using the TA Cloning Kit according to the manufacturer's instructions (Invitrogen, USA).

1E. Nucleotide Sequence Analysis

The nucleotide sequences of the cloned PCR fragments are determined by the dideoxy chain-termination method (Sanger, Nicklen, and Coulson, 1977, PNAS, USA 74:5463–5467), using 50–150 ng plasmid template, the Taq deoxy-terminal cycle sequencing kit (Perkin-Elmer, USA), fluorescent labeled terminators, and 5 pmol of the M13 forward or reverse primers (Invitrogen, USA) or synthetic oligonucleotide primers. Analysis of the sequence data is performed according to Devereux et al. (Devereux, J., Haeberli, P., and Smithies, O. (1984) Nucleic Acids Res. 12, 387–395).

The foregoing description of the invention is merely illustrative thereof, and it understood that variations and modifications can be effected without departing from the scope or spirit of the invention as set forth in the following claims.

All publications mentioned in this specification are herein incorporated by reference to the same extent as if each independent publication or patent application was specifically and individually indicated to be incorporated by reference.

What is claimed is:

1. A nucleic acid comprising an LNA unit having a modified base that provides a $T_m$ differential of 10° C. or less, wherein the modified base comprises an optionally substituted pyridyloxazole, optionally substituted pyrenylmethylglycerol, optionally substituted pyrrole, optionally substituted triazole, optionally substituted pyrenyl moiety, or optionally substituted 5-nitroindole.

2. The nucleic acid of claim 1 wherein the LNA unit comprises a carbon or hetero alicyclic ring with four to six ring members, and one or more of the alicyclic ring members form an additional cyclic linkage.

3. The nucleic acid of claim 2 wherein at least one of the alicyclic ring or the cyclic linkage contains at least one hetero atom ring member.

4. The nucleic acid of claim 2 wherein the alicyclic ring has at least one hetero atom ring member.

5. The nucleic acid of claim 2 wherein the alicyclic ring has at least one N, O, S or Se ring atom.

6. The nucleic acid of claim 2 wherein the cyclic linkage has at least one hetero atom in the linkage.

7. The nucleic acid claim 2 wherein the cyclic linkage has at least one N, O, S or Se atom in the linkage.

8. The nucleic acid of claim 2 wherein the linkage comprises two adjacent alicyclic ring members.

9. The nucleic acid of claim 2 wherein the linkage comprises two alicyclic ring members that are not adjacent.

10. The nucleic acid of claim 2 wherein the linkage is a C-1', C-2'; C-2', C-3'; C-2', C-4'; or a C-2', C-5' linkage.

11. The nucleic acid of claim 2 wherein the linkage comprises a total of from 3 to 6 atoms in addition to the alicyclic ring members.

12. The nucleic acid of claim 2 wherein the alicyclic group contains a single cyclic linkage.

13. The nucleic acid of claim 2 wherein the nucleic acid comprises at least one unit of the following formulae Ia or Ib:

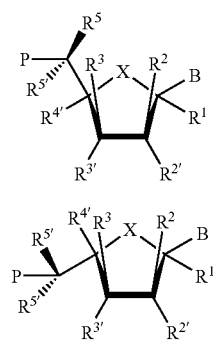

wherein X is oxygen, sulfur and carbon; B is a modified base; $R^1$, $R^2$ in formula Ia, $R^{2'}$ in formula Ib, either $R^3$ or $R^{3'}$, $R^5$, and $R^{5'}$ are hydrogen, methyl, ethyl, propyl, propynyl, aminoalkyl, methoxy, propoxy, methoxyethoxy, fluoro, or chloro, P designates the radical position for an internucleoside linkage to a succeeding monomer, or a 5'-terminal group, either $R^3$ or $R^{3'}$ is an internucleoside linkage to a preceding monomer, or a 3'-terminal group; in formula Ia, $R^{4'}$ and $R^{2'}$ together designate —CH$_2$—O—, —CH$_2$—S—, —CH$_2$—NH—, —CH$_2$—NMe-, —CH$_2$—CH$_2$—O—, —CH$_2$—CH$_2$—S—, —CH$_2$—CH$_2$—NH—, or —CH$_2$—CH$_2$—NMe- where the oxygen, sulfur or nitrogen, respectively, is attached to the 2'-position; in Formula Ib, $R^{4'}$ and $R^2$ together designate —CH$_2$—O—, —CH$_2$—S—, —CH$_2$—NH—, —CH$_2$—NMe-, —CH$_2$—CH$_2$—O—, —CH$_2$—CH$_2$—S—, —CH$_2$—CH$_2$—NH—, or —CH$_2$—CH$_2$—NMe- where the oxygen, sulfur or nitrogen, respectively, is attached to the 2-position ($R^2$ configuration).

14. The nucleic acid of claim 13 wherein B comprises a moiety selected from optionally substituted pyrenyl, optionally substituted pyridyloxazole, optionally substituted pyrenylmethylglycerol, optionally substituted pyrrole, optionally substituted diazole, optionally substituted triazole, or 5-nitroindole.

15. The nucleic acid of claim 1 wherein the LNA unit contains a modification at the 2'-position of a bicyclic group.

16. The nucleic acid of claims 15 comprising a moiety selected from the group consisting of 2'-deoxy-2'-fluoro ribonucleotides, 2'-O-methyl ribonucleotides, 2'-O-methoxyethyl ribonucleotides, peptide nucleic acids, 5-propynyl pyrimidine ribonucleotides, 7-deazapurine ribonucleotides, 2,6-diaminopurine ribonucleotides, and 2-thio-pyrimidine ribonucleotides.

17. The nucleic acid of claim 1 wherein the nucleic acid contains a single nucleic acid unit.

18. The nucleic acid of claim 1 comprising a plurality of nucleic acid units.

19. The nucleic acid of claim 1 comprising one or more natural DNA or RNA nucleotides.

20. The nucleic acid of claim 1 comprising one or more LNA units with natural nucleobases.

21. The nucleic acid of claim 20 wherein the one or more LNA units with natural nucleobases are incorporated into the nucleic acid at a distance of 1 to 6 bases from the LNA unit having a modified base.

22. The nucleic acid of claim 1 wherein the LNA unit provides a $T_m$ differential of 8° C. or less.

23. The nucleic acid of claim 22 wherein the LNA unit provides a $T_m$ differential of 6° C. or less.

24. The nucleic acid of claim 1 wherein greater than 50 percent of the total nucleotides are other than LNA units.

25. The nucleic acid of claim 1 containing from 5 to 100 total residues.

26. The nucleic acid of claim 1 comprising one or more oxy-LNA units, thio-residues, or amino-LNA units.

27. The nucleic acid of claim 1 comprising one or more residues selected from the group consisting of 2'-O,4'-C-methylene-β-D-ribofuranosyls, 2'-deoxy-2'-fluoro ribonucleotides, 2'-O-methyl ribonucleotides, 2'-O-methoxyethyl ribonucleotides, peptide nucleic acids, 5-propynyl pyrimidine ribonucleotides, 7-deazapurine ribonucleotides, 2,6-diaminopurine ribonucleotides, and 2-thio-pyrimidine ribonucleotides.

28. The nucleic acid of claim 1 wherein the nucleic acid is conjugated by forming a covalent or noncovalent bond to a compound selected from proteins, amplicons, enzymes, polysaccharides, antibodies, haptens, and peptides.

29. The nucleic acid of claim 1 wherein the nucleic acid comprises a fluorophore moiety and a quencher moiety, positioned in such a way that the hybridized state of the nucleic acid can be distinguished from the unbound state of the nuceic acid by a change in the fluorescent signal from the nucleotide.

30. The nucleic acid of claim 1 wherein the nucleic acid is adapted for use as a Taqman probe or Molecular Beacon.

31. A method for amplifying a target nucleic acid molecule, said method comprising the steps of:

(a) incubating a first nucleic acid of claim 1 with said target molecule under conditions that allow said first nucleic acid to bind said target molecule; and (b) extending said first nucleic acid with said target molecule as a template.

32. A method for detecting a target nucleic acid molecule, said method comprising the steps of:

(a) incubating a first nucleic acid of claim 1 with said target molecule under conditions that allow said first nucleic acid to hybridize to said target molecule; and (b) detecting said hybridization.

33. A method for nucleic acid manipulation comprising incubating a nucleic acid of claim 1 with an enzyme under conditions that allow said enzyme to bind or chemically modify said nucleic acid.

34. A method for inhibiting the expression of a target nucleic acid in a cell, said method comprising introducing into said cell a nucleic acid of claim 1 in an amount sufficient to specifically attenuate expression of said target nucleic acid.

35. A method for amplifying a target RNA, said method comprising the steps of:

(a) incubating a target RNA with a nucleic acid of claim 1 that comprises at least 2 consecutive thymines; and (b) extending said nucleic acid with said target RNA as a template.

36. A method for amplifying a target nucleic acid molecule, said method comprising the steps of:

(a) incubating a target molecule with a nucleic acid of claim 1 that comprises a region with substantial complementarity to a conserved region of two or more nucleic acids under conditions that allow said nucleic acid to bind said target molecule; and (b) extending said nucleic acid with said target molecule as a template.

37. A method for detecting a target nucleic acid molecule, said method comprising the steps of:

(a) incubating a target molecule with a nucleic acid of claim 1 that comprises a region with substantial complementarity to a conserved region of two or more nucleic acids under conditions that allow said nucleic acid to hybridize to said target molecule; and (b) detecting said hybridization.

38. The nucleic acid of claim 1, wherein said modified base comprises an optionally substituted pyridyloxazole, optionally substituted pyrenylmethylglycerol, optionally substituted pyrrole, optionally substituted triazole, or optionally substituted 5-nitroindole.

39. The method of claim 40, wherein said modified base of said nucleic acid of claim 1 comprises an optionally substituted pyridyloxazole, optionally substituted pyrenylmethylglycerol, optionally substituted pyrrole, optionally substituted triazole, or optionally substituted 5-nitroindole.

40. The nucleic acid of claim 1, wherein said modified base comprises 5-nitroindole.

41. The method of claim 34, wherein said modified base of said nucleic acid of claim 1 comprises 5-nitroindole.

\* \* \* \* \*